United States Patent
Dombret

(10) Patent No.: US 9,795,612 B2
(45) Date of Patent: Oct. 24, 2017

(54) PHARMACEUTICAL FORMULATION CONTAINING THIENOTRIAZOLODIAZEPINE COMPOUNDS

(71) Applicant: ONCOETHIX SA, Lausanne (CH)

(72) Inventor: Hervé Dombret, Lausanne (CH)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/908,626

(22) PCT Filed: Aug. 1, 2014

(86) PCT No.: PCT/EP2014/066629
§ 371 (c)(1),
(2) Date: Jan. 29, 2016

(87) PCT Pub. No.: WO2015/014998
PCT Pub. Date: Feb. 5, 2015

(65) Prior Publication Data
US 2016/0158245 A1 Jun. 9, 2016

Related U.S. Application Data

(60) Provisional application No. 61/863,118, filed on Aug. 7, 2013, provisional application No. 61/861,291, filed on Aug. 1, 2013.

(51) Int. Cl.
*A61K 9/16* (2006.01)
*A61K 31/551* (2006.01)

(52) U.S. Cl.
CPC .......... *A61K 31/551* (2013.01); *A61K 9/1635* (2013.01); *A61K 9/1652* (2013.01); *A61K 9/1676* (2013.01); *A61K 9/1694* (2013.01)

(58) Field of Classification Search
None
See application file for complete search history.

(56) References Cited

FOREIGN PATENT DOCUMENTS

| | | |
|---|---|---|
| EP | 1297836 A1 | 4/2003 |
| EP | 2239264 A1 | 10/2010 |
| WO | 2011143660 A2 | 11/2011 |
| WO | 2012075456 A1 | 6/2012 |
| WO | 2014068402 A2 | 5/2014 |

*Primary Examiner* — Michael Barker
(74) *Attorney, Agent, or Firm* — Catherine D. Fitch; Richard S. Parr; Janet E. Fair

(57) ABSTRACT

A method of treating lymphoblastic leukemia, acute myeloid leukemia, BCR-ABL positive acute lymphoblastic leukemia or CD34 positive acute myeloid leukemia comprising the step of administering to a patient a pharmaceutically acceptable amount of a composition comprising a thienotriazolodiazepine compound according to Formula (1) as a solid dispersion wherein X is a halogen, $R^1$ is $C_1$-$C_4$ alkyl, $R^2$ is $C_1$-$C_4$ alkyl, a is an integer of 1-4, $R^3$ is $C_1$-$C_4$ alkyl, $C_1$-$C_4$ hydroxyalkyl, $C_1$-$C_4$ alkoxy, phenyl optionally having substituent(s), or heteroaryl optionally having substituent(s), a pharmaceutically acceptable salt thereof or a hydrate thereof; and a pharmaceutically acceptable polymer. In one embodiment, the pharmaceutically acceptable polymer is HPMCAS.

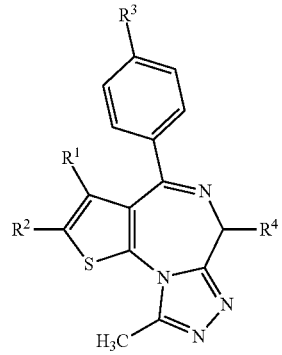

(1)

16 Claims, 64 Drawing Sheets

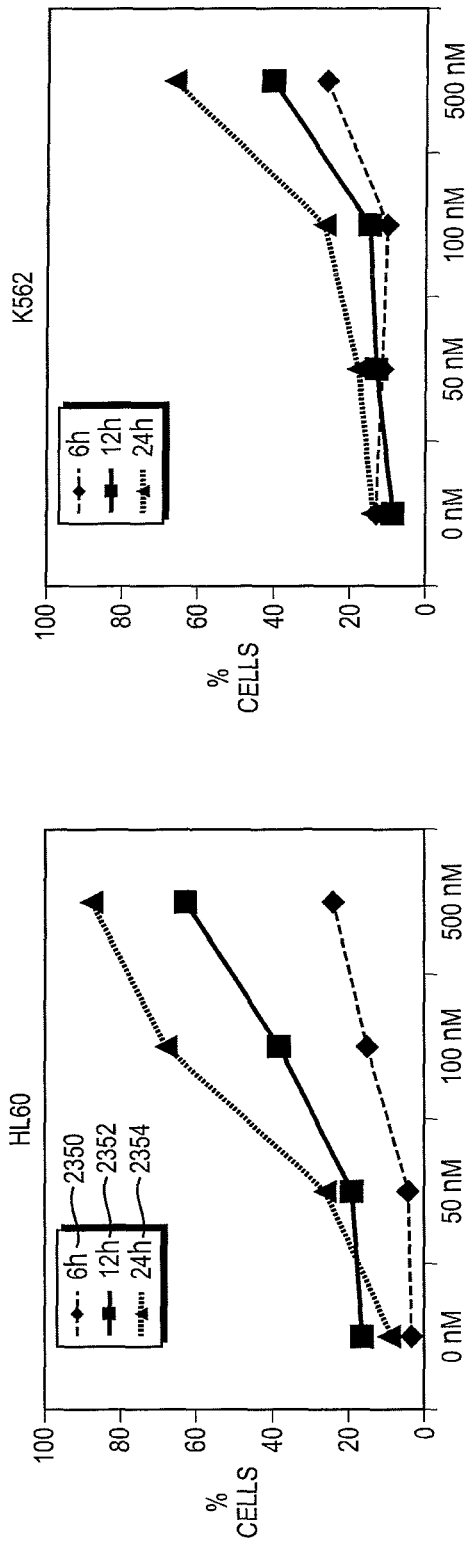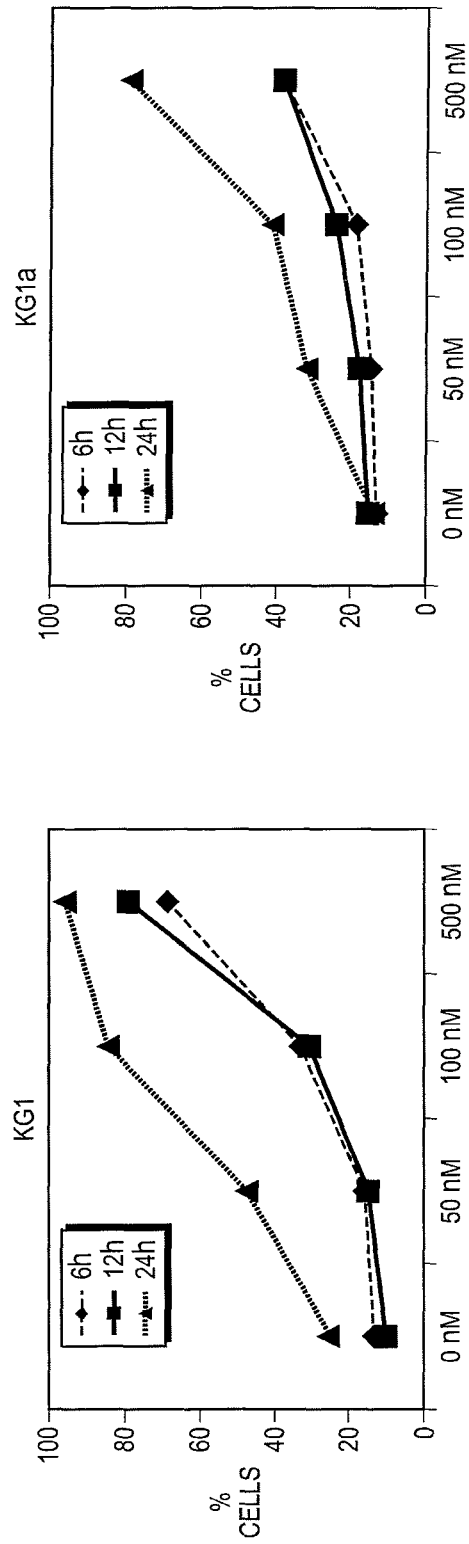
FIG. 14A
FIG. 14B
FIG. 14C
FIG. 14D

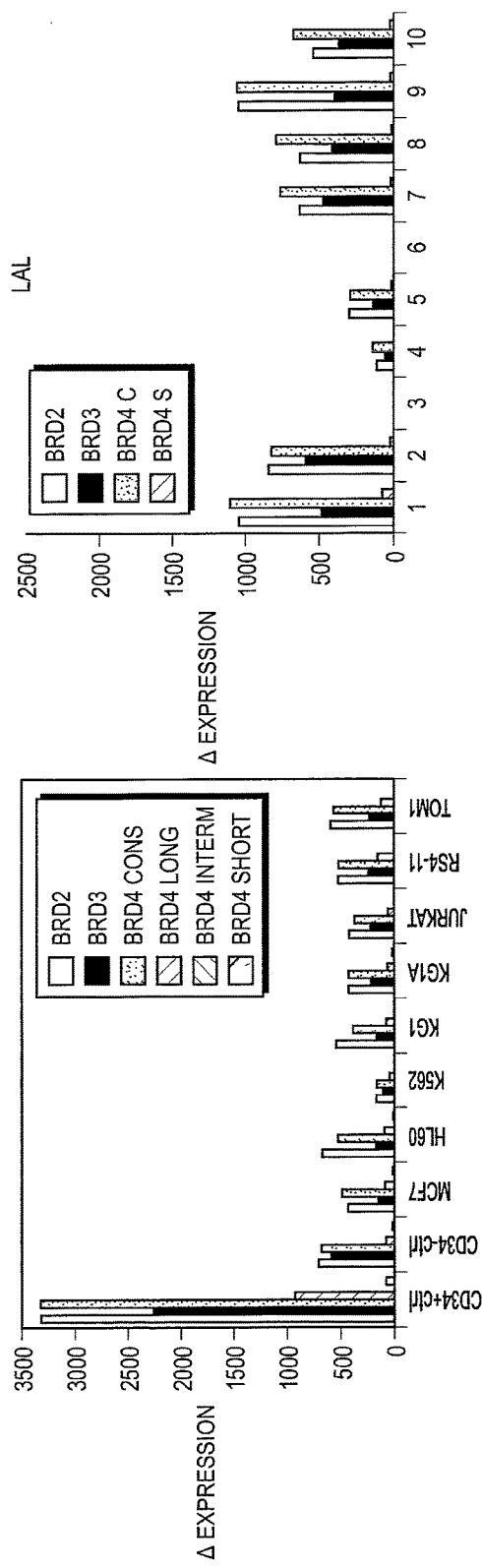
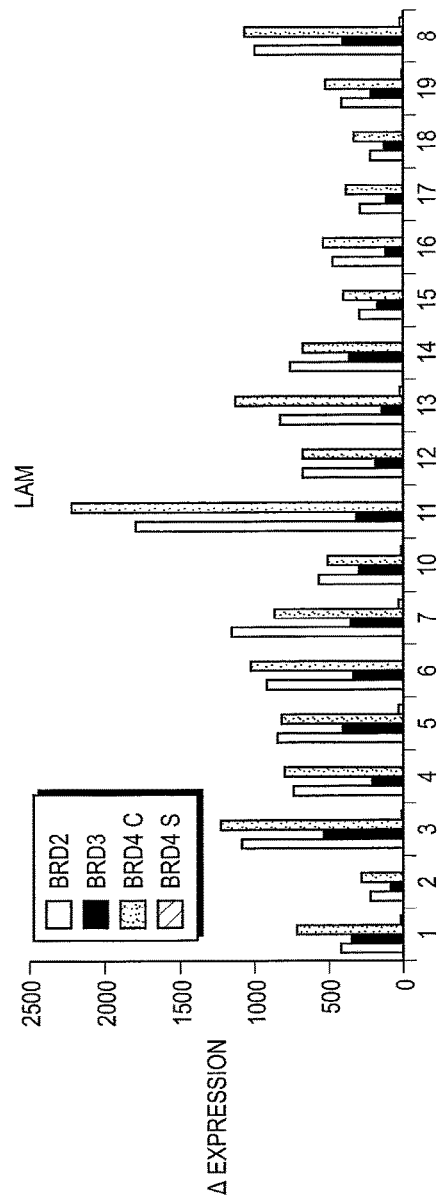
FIG. 17A
FIG. 17B
FIG. 17C

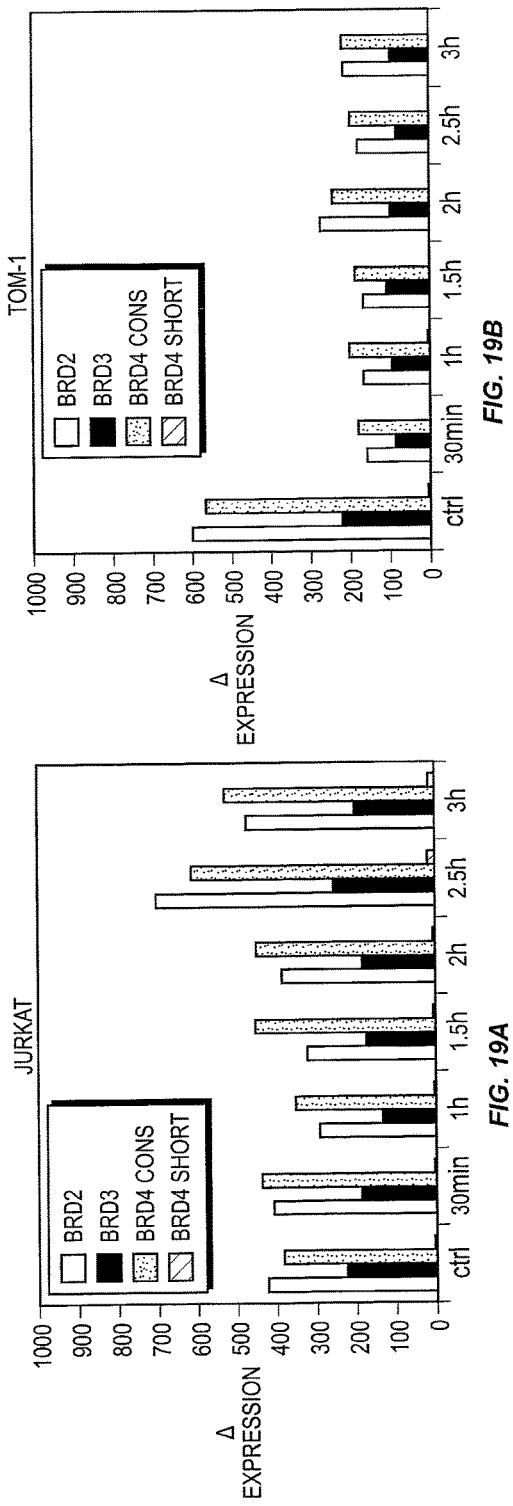
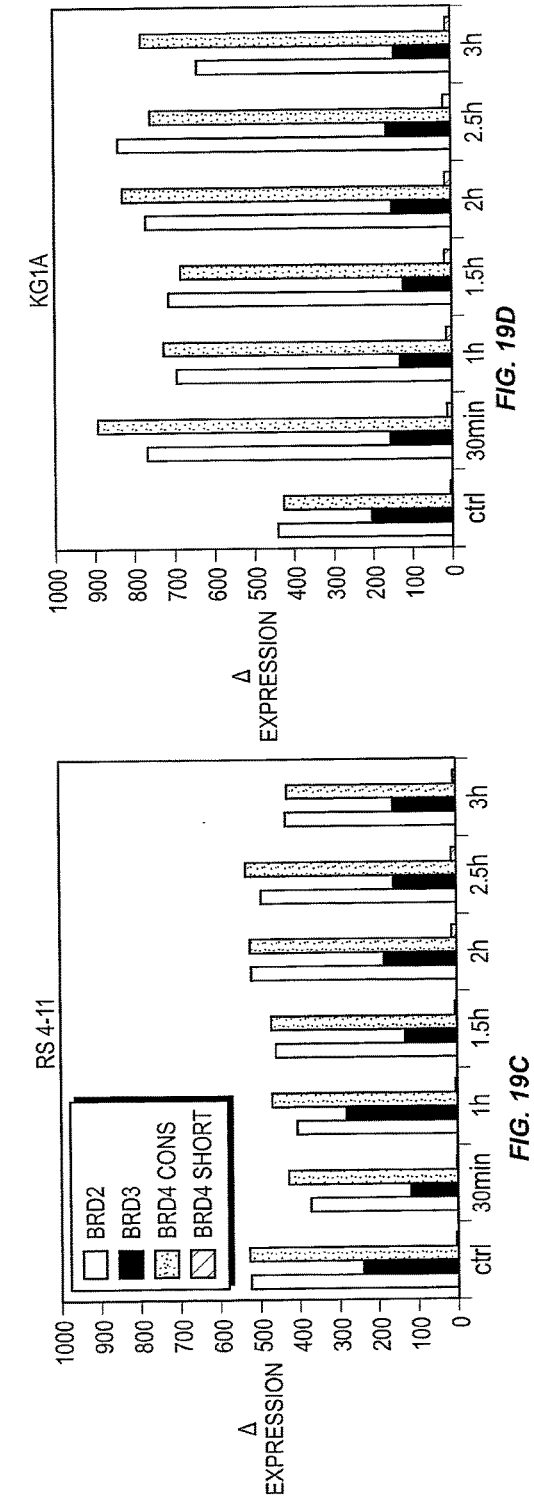
FIG. 19A FIG. 19B FIG. 19C FIG. 19D

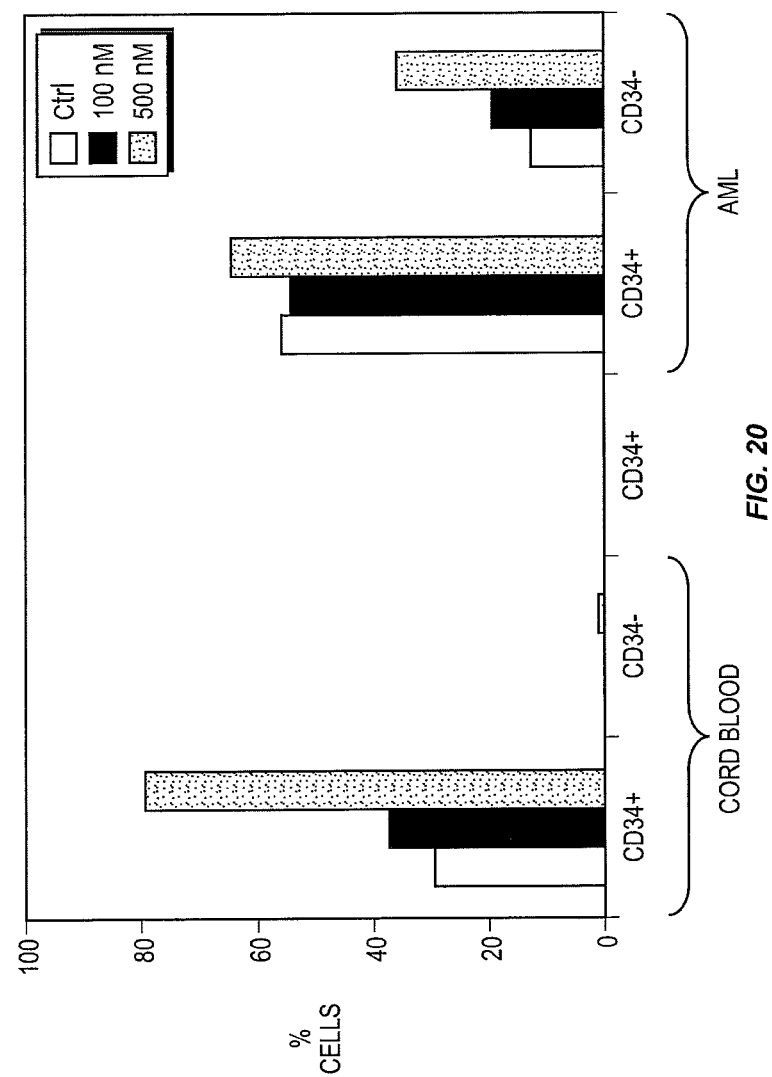

HL60_Ctrl_2
EVENT COUNT: 13836

HL60_Y-803 1nM_2
EVENT COUNT: 14698

HL60_Y-803 10nM_2
EVENT COUNT: 16337

HL60_Ctrl_1
EVENT COUNT: 14407

HL60_Y-803 1nM_1
EVENT COUNT: 23162

HL60_Y-803 10nM_1
EVENT COUNT: 44471

HL60_Ctrl_2
EVENT COUNT: 13369

HL60_Y-803 1nM_2
EVENT COUNT: 46147

HL60_Y-803 10nM_2
EVENT COUNT: 122325

HL60_Ctrl_1
EVENT COUNT: 14273

HL60_Y-803 1nM_1
EVENT COUNT: 72420

HL60_Y-803 10nM_1
EVENT COUNT: 62160

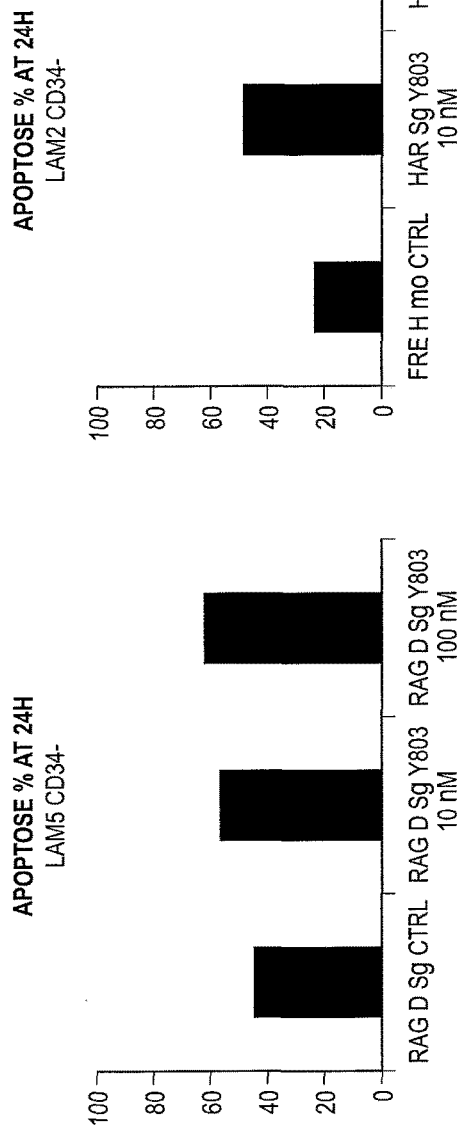
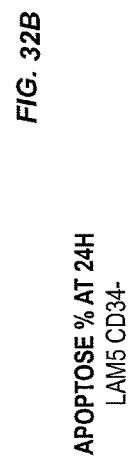
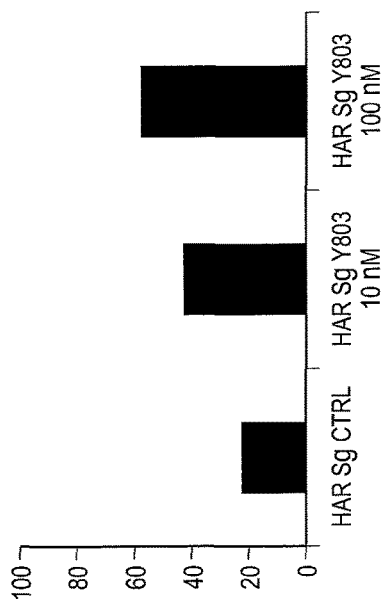
FIG. 32A
FIG. 32B
FIG. 32C

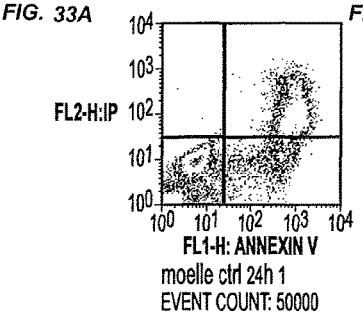
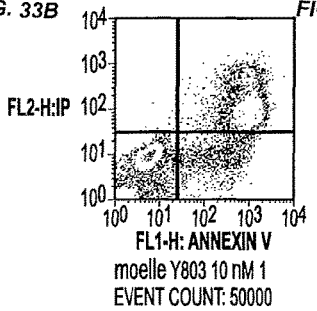
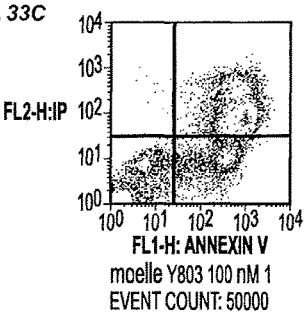
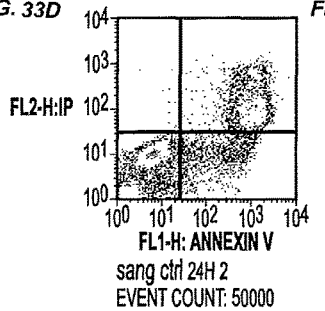
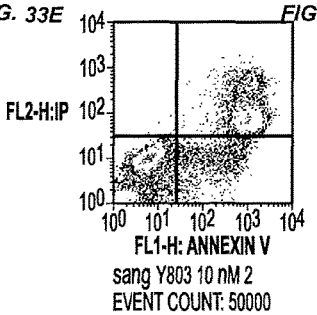
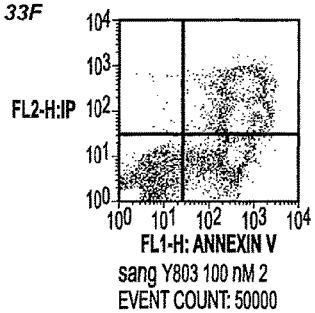
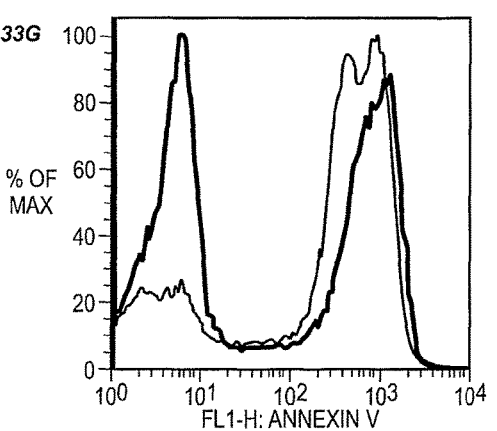

| | CTRL | DMSO1% | 25nM | 100nM | 250nM | 500nM |
|---|---|---|---|---|---|---|
| HL60 | 17,00 | 12,00 | 12,75 | 15,00 | 23,70 | 27,65 |
| K562 | 22,55 | 21,15 | 37,35 | 23,80 | 32,20 | 32,90 |
| KG1 | 9,20 | 16,60 | 14,55 | 19,75 | 23,45 | 37,50 |
| KG1a | 22,70 | 15,70 | 28,00 | 26,10 | 56,70 | 57,10 |
| NOMO | 13,50 | 24,05 | 32,45 | 33,55 | 59,60 | 86,60 |

| | | | | | | |
|---|---|---|---|---|---|---|
| RS4-11 | 10,80 | 13,05 | 15,65 | 20,70 | 37,55 | 60,15 |
| BV-173 | 13,47 | 24,38 | 26,50 | 27,52 | 37,46 | 64,61 |
| Jurkat | 28,40 | 28,60 | 45,80 | 34,90 | 85,55 | 84,53 |
| TOM-1 | 21,95 | 48,20 | 51,80 | 71,00 | 76,60 | 88,20 |

|  | KG1 | | KG1a | | HL60 | | NOMO1 | | K562 | | RS4-11 | | Jurkat | | BV173 | | TOM1 | |
| --- | --- | --- | --- | --- | --- | --- | --- | --- | --- | --- | --- | --- | --- | --- | --- | --- | --- | --- |
|  | G1 | S | G1 | S | G1 | S | G1 | S | G1 | S | G1 | S | G1 | S | G1 | S | G1 | S |
| DMSO 1% | 46,78 | 26,93 | 49,70 | 24,65 | 57,13 | 14,75 | 52,93 | 25,13 | 53,63 | 25,58 | 59,85 | 25,63 | 54,90 | 20,20 | 49,00 | 34,30 | 75,85 | 10,60 |
| OTX015 25nM | 46,78 | 23,38 | 52,10 | 20,80 | 66,30 | 6,66 | 51,78 | 22,30 | 57,45 | 20,95 | 69,48 | 17,43 | 52,35 | 19,40 | 55,90 | 30,95 | 80,85 | 6,13 |
| OTX015 100nM | 43,43 | 23,15 | 48,45 | 15,35 | 67,48 | 4,98 | 55,33 | 20,10 | 61,30 | 17,38 | 84,65 | 5,08 | 48,08 | 23,28 | 66,00 | 22,40 | 70,05 | 5,20 |
| OTX015 250nM | 37,50 | 19,53 | 21,85 | 18,30 | 66,18 | 4,75 | 53,70 | 16,63 | 67,28 | 12,86 | 85,53 | 3,48 | 41,13 | 24,85 | 68,35 | 14,15 | 71,70 | 5,03 |
| OTX015 500nM | 43,23 | 18,58 | 21,70 | 17,20 | 66,80 | 5,16 | 52,13 | 13,85 | 67,40 | 12,83 | 79,08 | 4,00 | 35,28 | 23,18 | 61,65 | 10,31 | 78,35 | 4,51 |

*FIG. 40H*

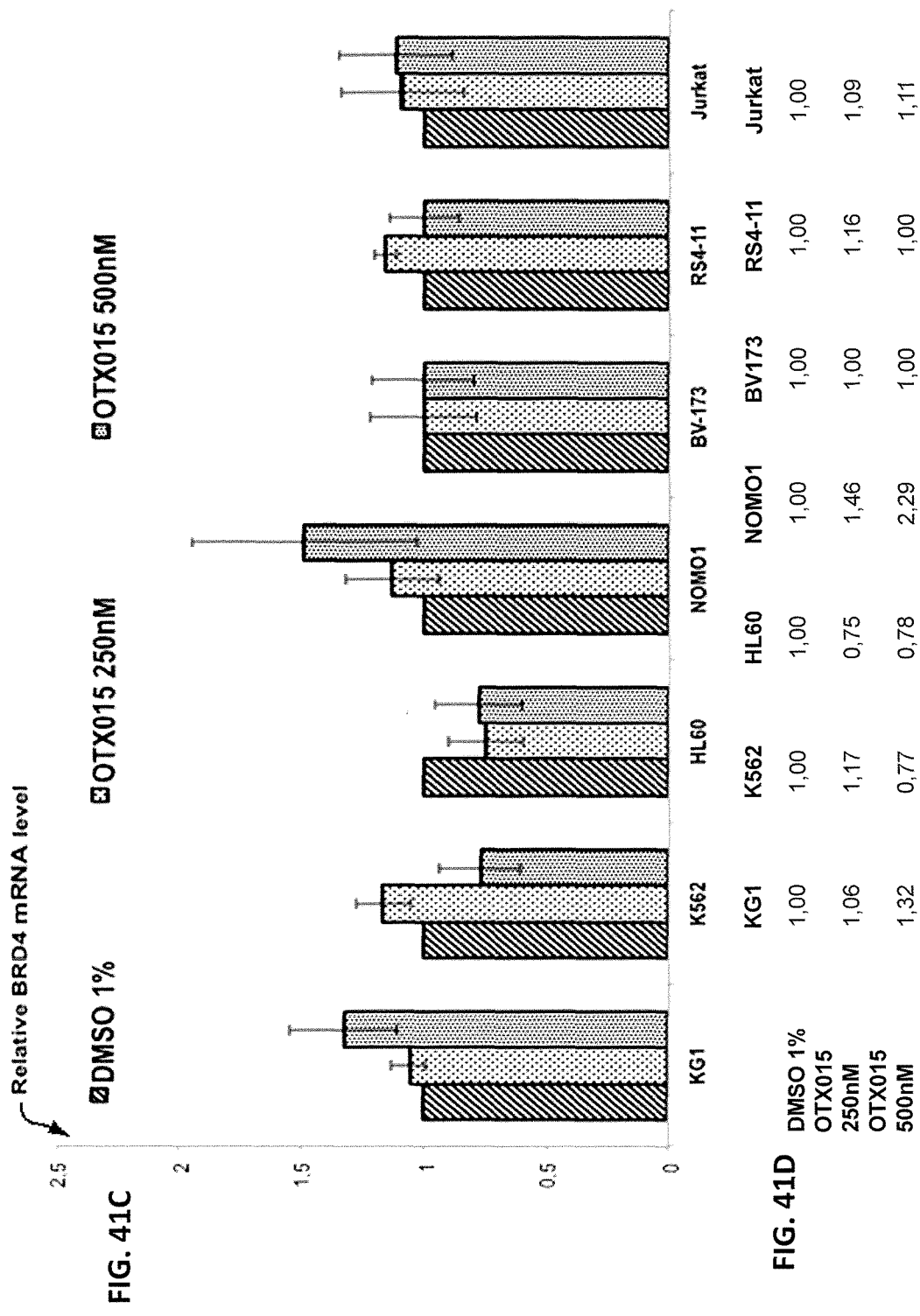

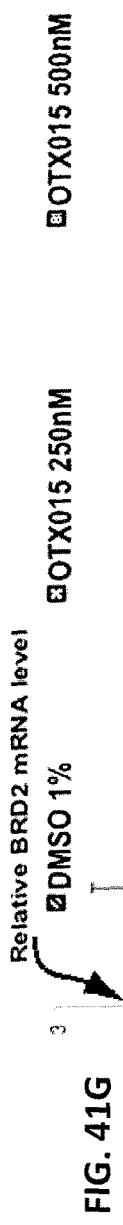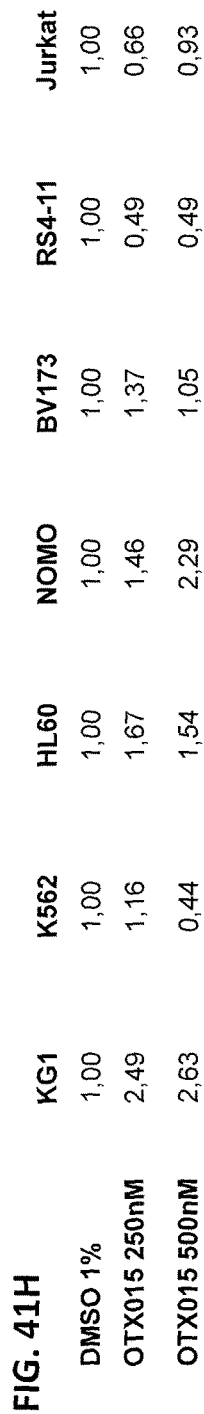
FIG. 41G
FIG. 41H
|  | KG1 | K562 | HL60 | NOMO | BV173 | RS4-11 | Jurkat |
|---|---|---|---|---|---|---|---|
| DMSO 1% | 1,00 | 1,00 | 1,00 | 1,00 | 1,00 | 1,00 | 1,00 |
| OTX015 250nM | 2,49 | 1,16 | 1,67 | 1,46 | 1,37 | 0,49 | 0,66 |
| OTX015 500nM | 2,63 | 0,44 | 1,54 | 2,29 | 1,05 | 0,49 | 0,93 |

| KG1 | HL60 | NOMO | BV173 | Jurkat | RS4-11 | K562 |
|---|---|---|---|---|---|---|
| 4372,80 | 4231,92 | 1607,12 | 2077,82 | 1844,62 | 1619,92 | 449,75 |

|  | KG1 | NOMO1 | K562 | HL60 | RS4-11 | BV173 | Jurkat |
|---|---|---|---|---|---|---|---|
| DMSO 1% | 1,00 | 1,00 | 1,00 | 1,00 | 1,00 | 1,00 | 1,00 |
| OTX015 250nM | 0,76 | 0,28 | 0,33 | 0,08 | 1,01 | 0,51 | 0,35 |
| OTX015 500nM | 0,67 | 0,36 | 0,18 | 0,13 | 0,60 | 0,43 | 0,19 |

FIG. 43A
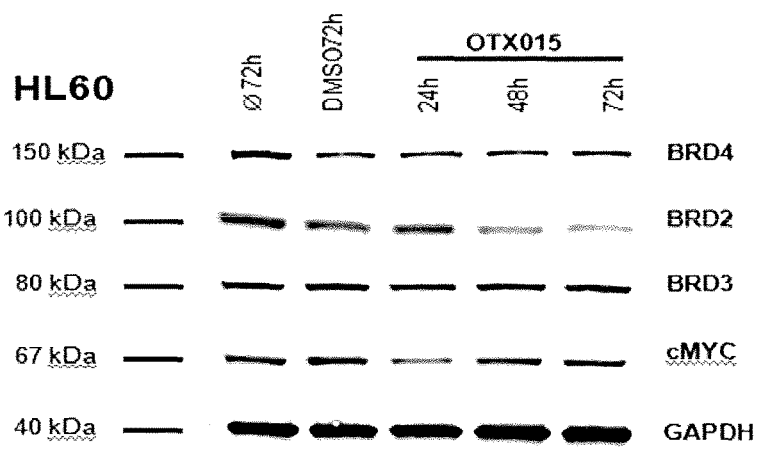
FIG. 43B
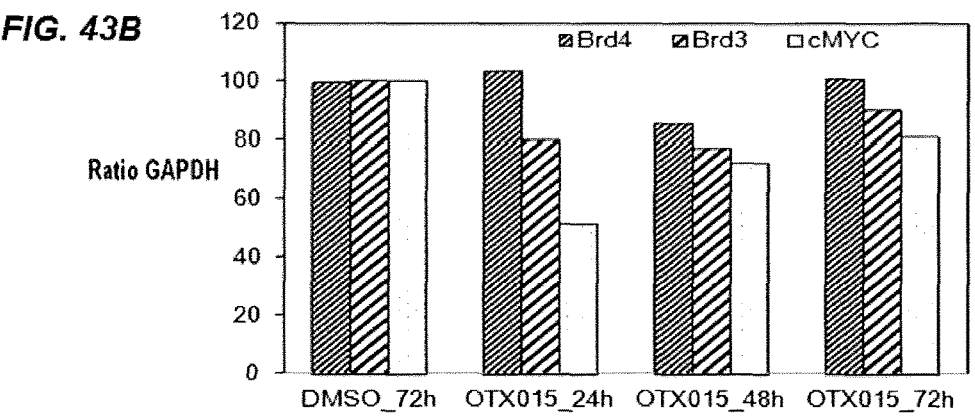
FIG. 43C
|  | DMSO 72h | OTX015 24h | OTX015 48h | OTX015 72h |
|---|---|---|---|---|
| Brd4 | 100 | 104 | 86 | 101 |
| Brd3 | 100 | 80 | 77 | 90 |
| cMYC | 100 | 52 | 72 | 81 |

FIG. 43D K562
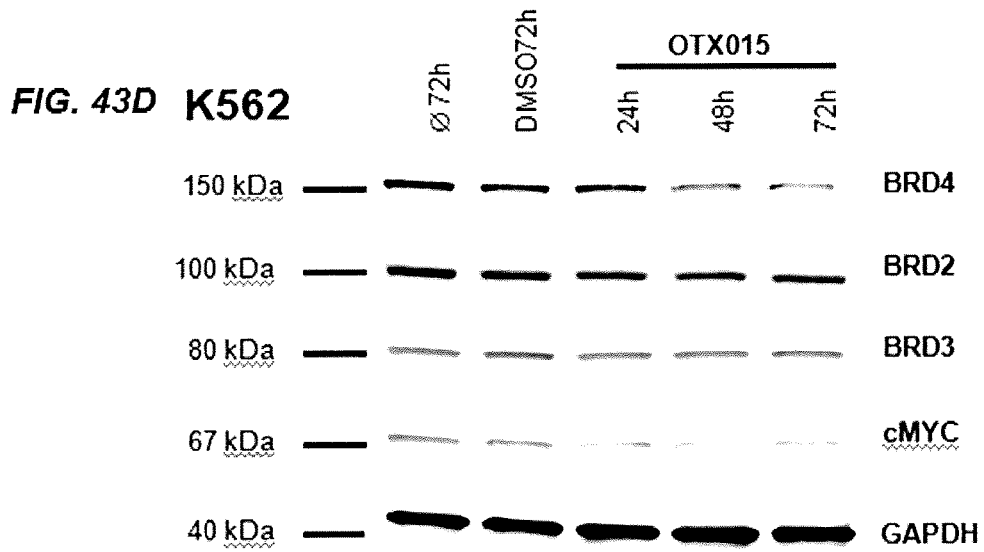
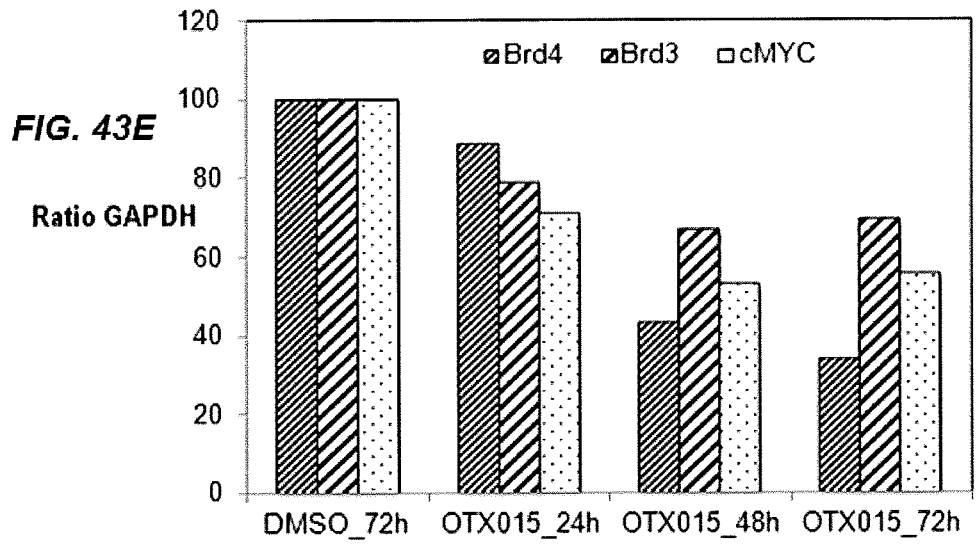
FIG. 43E
FIG. 43F
|  | DMSO 72h | OTX015 24h | OTX015 48h | OTX015 72h |
|---|---|---|---|---|
| Brd4 | 100 | 89 | 43 | 34 |
| Brd3 | 100 | 79 | 67 | 69 |
| cMYC | 100 | 71 | 53 | 56 |

FIG. 43G JURKAT

| | DMSO 72h | OTX015 24h | OTX015 48h | OTX015 72h |
|---|---|---|---|---|
| Brd4 | 100 | 101 | 87 | 86 |
| Brd3 | 100 | 101 | 100 | 101 |
| cMYC | 100 | 94 | 69 | 71 |

FIG. 43J
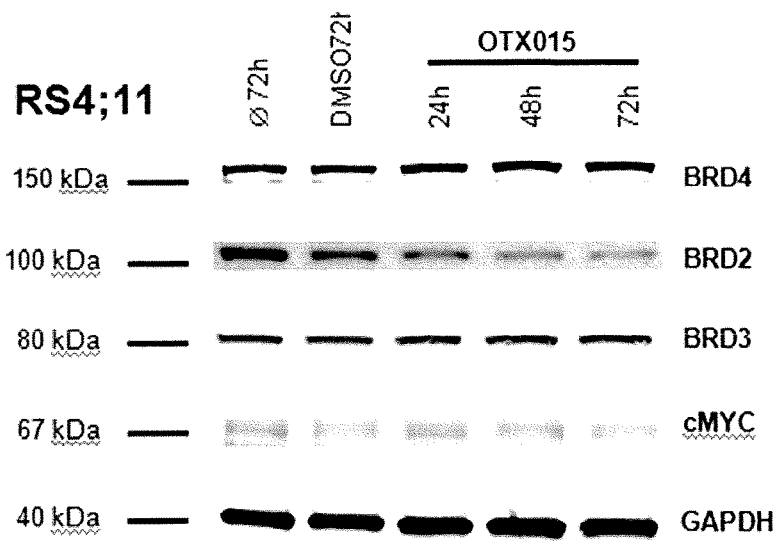
FIG. 43K
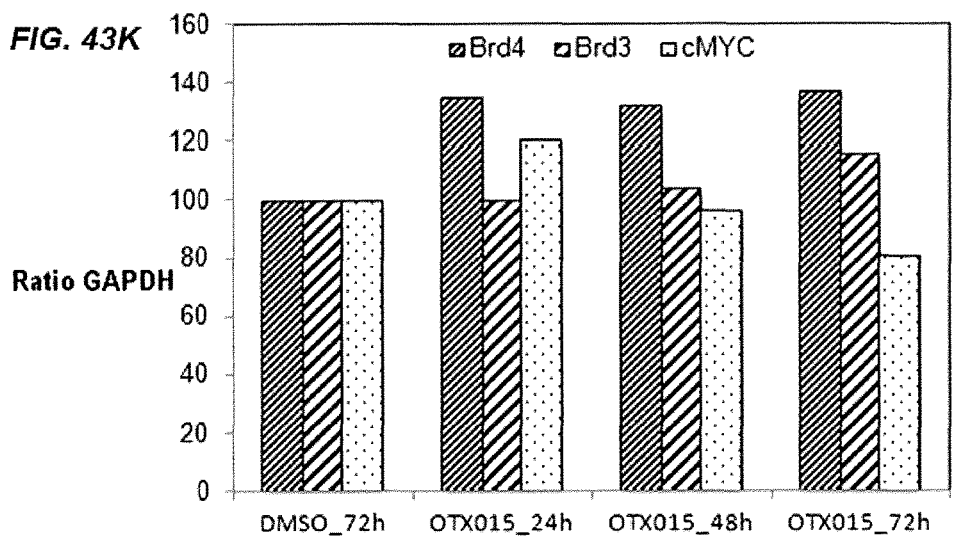
FIG. 43L
|        | DMSO 72h | OTX015 24h | OTX015 48h | OTX015 72h |
|--------|----------|------------|------------|------------|
| Brd4   | 100      | 135        | 132        | 137        |
| Brd3   | 100      | 100        | 104        | 116        |
| cMYC   | 100      | 121        | 96         | 81         |

Table 10: Characteristics of the 7 patients tested for OTX015 effect on fresh AML and ALL blast cells.

| Patient | Gender | FAB | Karyotype | Genotype | BM blast % |
|---|---|---|---|---|---|
| 1 | F | sAML | 46;XX | FLT3-ITD+/NPM+ | 87 |
| 2 | M | AML4 | 46;XY | FLT3-ITD+/NPM+ | 80 |
| 3 | F | AML2 | 46;XX;t8;21 | AML-ETO+ | 25 |
| 4 | M | AML5 | 46;XY | FLT3-+/NPM+ | 90 |
| 5 | M | AML5 | 46;XY | FLT3 ITD+ | 95 |
| 6 | M | B-ALL | 46;XY;t9;22 | bcr-abl+ / Ikaros del | 96 |
| 7 | F | B-ALL | 46;XX; complex | Ikaros del | 67 |

FIG. 44D

FIG. 45A
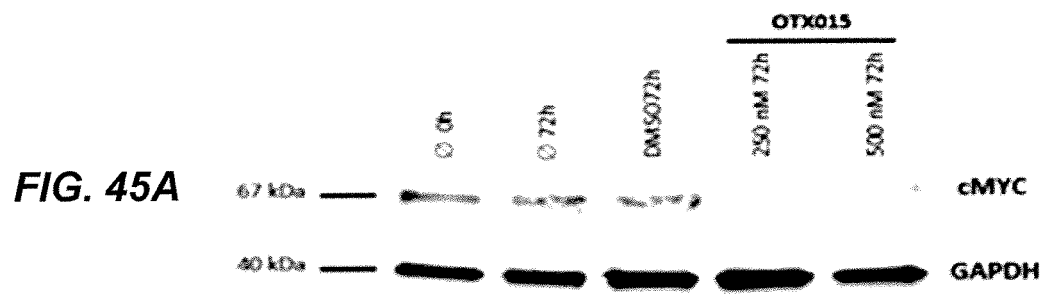
FIG. 45B
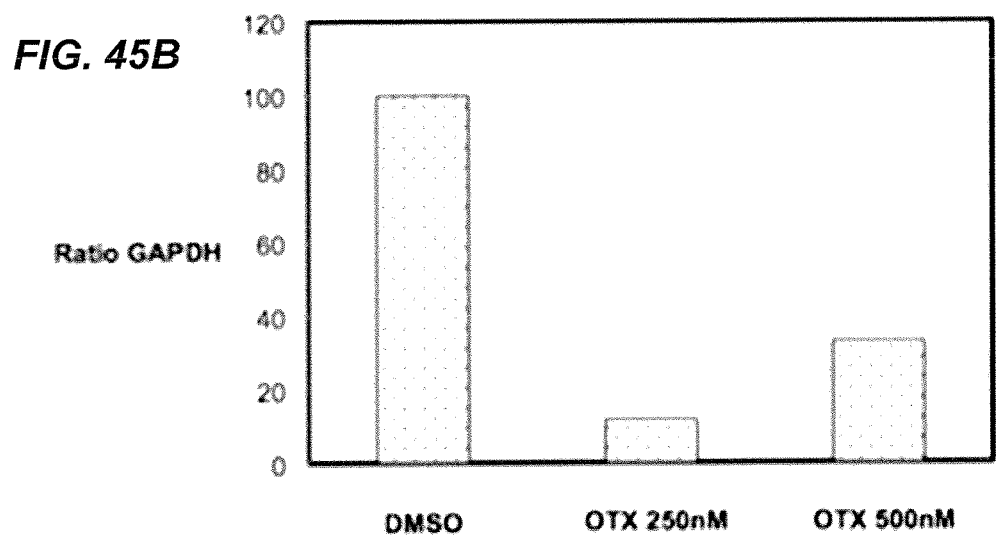
FIG. 45C
|  | DMSO | OTX015 250nM | OTX015 500nM |
|---|---|---|---|
| cMYC | 100 | 12 | 33 |

|  | 24h | 48h | 72h |
|---|---|---|---|
| DMSO 1% | 100 | 100 | 100 |
| OTX015 250nM | 29,02 | 46,95 | 38,37 |
| OTX015 500nM | 19,94 | 34,86 | 30,92 |

| Cancer Type | Cell Line | BRD2 mRNA* | BRD3 mRNA* | BRD4 mRNA* | BRD3 protein# | BRD4 protein# | GI50 (nM)** | Apoptosis (% baseline/ % treated) | Change in BRD3 protein (DMSO/ treated) | Change in BRD4 protein (DMSO/ treated) | Change in BRD2 mRNA (DMSO/ treated) | Change in BRD3 mRNA (DMSO/ treated) | Change in BRD4 mRNA (DMSO/ treated) | G1 Arrest (DMSO/ % treated) | Change in cMYC protein (DMSO/ treated) | Change in cMYC mRNA (DMSO/ treated) |
|---|---|---|---|---|---|---|---|---|---|---|---|---|---|---|---|---|
| AML | HL60 | 4 | 2 | 5 | 0.6 | 0.6 | 1 307 | 12/23.7 | 0.75/0.67 | 0.23/0.23 | 1/1.5 | 1/0.7 | 1/0.7 | 57/65.7 | 1.28/1.04 | 1/0.1 |
|  | K562 | 1 | 0.2 | 1.5 | 0.26 | 0.5 | 11 342 | 21.2/31.7 | 0.28/0.19 | 0.29/0.1 | 1/1.1 | 1/1.5 | 1/1.1 | 53.6/67.3 | 0.67/0.37 | 1/0.3 |
|  | KG1 | 5 | 2 | 5.5 | ND | ND | 198 | 16.6/23.5 | ND | ND | 1/2.5 | 1/1.5 | 1/1 | 55.1/54.5 | ND | 1/1.7 |
|  | KG1a | ND | ND | ND | ND | ND | 1 343 | 15.7/56.7 | ND | ND | ND | ND | ND | 49.7/48.5 | ND | ND |
|  | NOMO1 | 4.5 | 2 | 5 | ND | ND | 229 | 24.1/59.6 | ND | ND | 1/1.1 | 1/1 | 1/1.1 | 52.7/54 | ND | 1/1.3 |
| ALL | RS4-11 | 2 | 1 | 3 | 0.82 | 0.45 | 34 | 13.1/37.5 | 0.87/1.01 | 0.52/0.71 | 1/0.5 | 1/0.8 | 1/1.1 | 59.9/85.5 | 0.37/0.3 | 1/1 |
|  | BV-173 | 2 | 1 | 2.2 | ND | ND | 161 | 24.4/37.5 | ND | ND | 1/1.2 | 1/0.8 | 1/1 | 49/68.4 | ND | 1/0.5 |
|  | Jurkat | 3 | 1.5 | 4 | 6.68 | 2.39 | 250 | 28.6/85.6 | 4.91/4.93 | 1.36/1.17 | 1/1/0.6 | 1/1.5 | 1/1.1 | 63.5/61.5 | 3.48/2.47 | 1/0.3 |
|  | TOM-1 | ND | ND | ND | ND | ND | 133 | 48.2/76.6 | ND | ND | ND | ND | ND | 75.9/76.1 | ND | ND |

\* Results from real-time quantitative RT-PCR, expressed as n-fold target gene expression relative to ABL \# Results from Western blotting, expressed as n-fold protein expression relative to GADPH \*\*MTT assay

FIG. 46

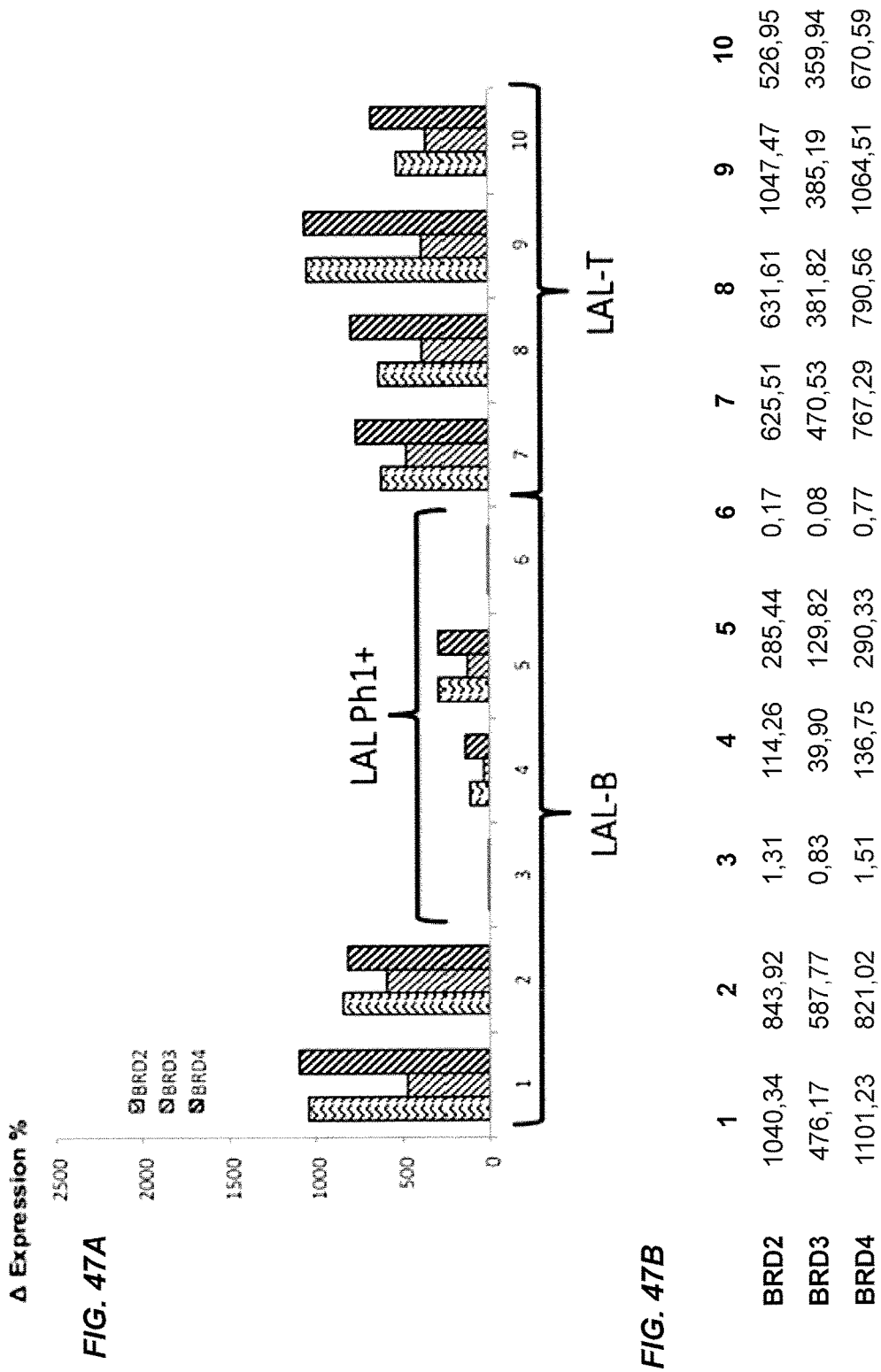

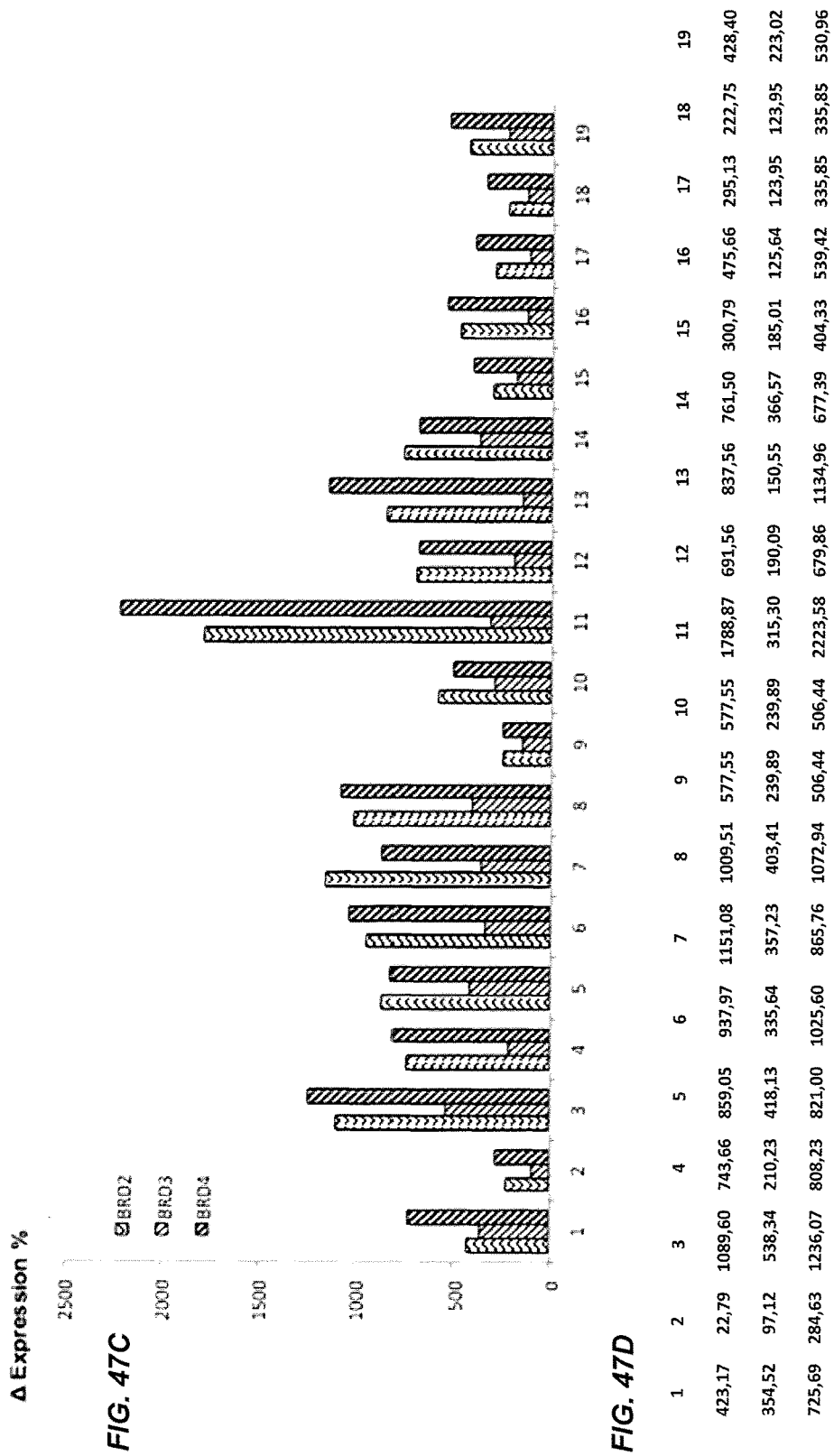

| N° | Gender | Disease | Karyotype | Molecular Biology |
|---|---|---|---|---|
| 1 | M | B-ALL | Normal | - |
| 2 | F | B-ALL | Normal | - |
| 3 | M | B-ALL | PH1+ | bcr/abl |
| 4 | F | B-ALL | PH1+ | bcr/abl |
| 5 | M | B-ALL | PH1+ | bcr/abl |
| 6 | M | B-ALL | PH1+ | bcr/abl |
| 7 | M | T-ALL | UK | - |
| 8 | F | T-ALL | UK | - |
| 9 | M | T-ALL | UK | - |
| 10 | M | T-ALL | Normal | CalmAf10 |
| 1 | M | AML | Normal | CEBP alpha |
| 2 | M | AML | Normal | dup MLL |
| 3 | F | AML | Normal | dup MLL |
| 4 | F | AML | Normal | FLT3 ITD |
| 5 | M | AML | Normal | FLT3 ITD |
| 6 | F | AML | Normal | FLT3 ITD |
| 7 | M | AML | Normal | FLT3 ITD + Dup MLL |
| 8 | M | AML | inv 16 | CBF MYH |
| 9 | M | AML | inv 16 | CBF MYH |
| 10 | F | AML | Complex | - |
| 11 | M | AML | Complex | - |
| 12 | F | AML | Normal | NPM1 |
| 13 | M | AML | Normal | NPM1 |
| 14 | F | AML | Normal | NPM1 |
| 15 | M | AML | Normal | NPM1 |
| 16 | M | AML | Normal | NPM1 |
| 17 | F | AML | Normal | NPM1 + FLT3 ITD |
| 18 | M | AML | t(8;21) | AML ETO |
| 19 | M | AML | t(8;21) | AML ETO |

*FIG. 47E*

SEQUENCE LISTING

<160> NUMBER OF SEQ ID NOS: 15

<210> SEQ ID NO 1
<211> LENGTH: 22
<212> TYPE: DNA
<213> ORGANISM: Artificial Sequence
<220> FEATURE:
<223> OTHER INFORMATION: c-MYC Forward Primer for PCR

<400> SEQUENCE: 1 ggatttttt cgggtagtgg aa                                      22

<210> SEQ ID NO 2
<211> LENGTH: 23
<212> TYPE: DNA
<213> ORGANISM: Artificial Sequence
<220> FEATURE:
<223> OTHER INFORMATION: c-MYC Reverse Primer for PCR

<400> SEQUENCE: 2
ttcctgttgg tgaagctaac gtt                                    23

<210> SEQ ID NO 3
<211> LENGTH: 19
<212> TYPE: DNA
<213> ORGANISM: Artificial Sequence
<220> FEATURE:
<223> OTHER INFORMATION: c-MYC Probe

<400> SEQUENCE: 3
ctcccgcgac gatgcccct                                         19

<210> SEQ ID NO 4
<211> LENGTH: 19
<212> TYPE: DNA
<213> ORGANISM: Artificial Sequence
<220> FEATURE:
<223> OTHER INFORMATION: BRD4 Forward Primer for PCR

<400> SEQUENCE: 4
ccctgaagcc gtccacact                                         19

<210> SEQ ID NO 5
<211> LENGTH: 24
<212> TYPE: DNA
<213> ORGANISM: Artificial Sequence
<220> FEATURE:
<223> OTHER INFORMATION: BRD4 Reverse Primer for PCR

<400> SEQUENCE: 5
ttctcagctt gaggtttcct tttc                                   24

<210> SEQ ID NO 6
<211> LENGTH: 25
<212> TYPE: DNA
<213> ORGANISM: Artificial Sequence
<220> FEATURE:
<223> OTHER INFORMATION: BRD4 Probe

<400> SEQUENCE: 6
cgctatgtca cctcctgttt gcgga                                  25

<210> SEQ ID NO 7
<211> LENGTH: 22
<212> TYPE: DNA
<213> ORGANISM: Artificial Sequence

```
<220> FEATURE:
<223> OTHER INFORMATION: BRD3 Forward Primer

<400> SEQUENCE: 7
acatgcagaa tgtggtggtg aa                                                  22

<210> SEQ ID NO 8
<211> LENGTH: 18
<212> TYPE: DNA
<213> ORGANISM: Artificial Sequence
<220> FEATURE:
<223> OTHER INFORMATION: BRD3 Reverse Primer for PCR

<400> SEQUENCE: 8
cgtccacggg ctggtaga                                                       18

<210> SEQ ID NO 9
<211> LENGTH: 25
<212> TYPE: DNA
<213> ORGANISM: Artificial Sequence
<220> FEATURE:
<223> OTHER INFORMATION: BRD3 Probe

<400> SEQUENCE: 9
acgctctgga aacaccagtt cgcct                                               25

<210> SEQ ID NO 10
<211> LENGTH: 20
<212> TYPE: DNA
<213> ORGANISM: Artificial Sequence
<220> FEATURE:
<223> OTHER INFORMATION: BRD2 Forward Primer for PCR

<400> SEQUENCE: 10
cccgacgaga ttgaaatcga                                                     20

<210> SEQ ID NO 11
<211> LENGTH: 21
<212> TYPE: DNA
<213> ORGANISM: Artificial Sequence
<220> FEATURE:
<223> OTHER INFORMATION: BRD2 Reverse Primer for PCR

<400> SEQUENCE: 11
ccgcaaacag gaggtgacat a                                                   21

<210> SEQ ID NO 12
<211> LENGTH: 26
<212> TYPE: DNA
<213> ORGANISM: Artificial Sequence
<220> FEATURE:
<223> OTHER INFORMATION: BRD2 Probe

<400> SEQUENCE: 12
ttgagaccct gaagccgtcc acactg                                              26

<210> SEQ ID NO 13
<211> LENGTH: 31
<212> TYPE: DNA
<213> ORGANISM: Artificial Sequence
<220> FEATURE:
<223> OTHER INFORMATION: ABL Forward Primer for PCR

<400> SEQUENCE: 13
tggagataac actctaagca taactaaagg t                                        31
```

```
<210> SEQ ID NO 14
<211> LENGTH: 21
<212> TYPE: DNA
<213> ORGANISM: Artificial Sequence
<220> FEATURE:
<223> OTHER INFORMATION: ABL Reverse Primer for PCR

<400> SEQUENCE: 14
gatgtagttg cttgggaccc a                                     21

<210> SEQ ID NO 15
<211> LENGTH: 28
<212> TYPE: DNA
<213> ORGANISM: Artificial Sequence
<220> FEATURE:
<223> OTHER INFORMATION: ABL Probe

<400> SEQUENCE: 15
ccatttttgg tttgggcttc acaccatt                              28
```

PHARMACEUTICAL FORMULATION CONTAINING THIENOTRIAZOLODIAZEPINE COMPOUNDS

CROSS-REFERENCE TO RELATED APPLICATIONS

This application is a National Stage application of PCT/EP2014/066629, filed Aug. 1, 2014, which claims the benefit of U.S. Provisional Application Ser. No. 61/863,118, filed Aug. 7, 2013, and U.S. Provisional Application Ser. No. 61/861,291, filed Aug. 1, 2013, each of which is incorporated herein by reference in its entirety.

REFERENCE TO SEQUENCE LISTING SUBMITTED ELECTRONICALLY

The sequence listing of the present application is submitted electronically via EFS-Web as an ASCII formatted sequence listing with a file name "24218USPCT-SEQTXT-14JAN2016", creation date of Jan. 14, 2016, and a size of 4 KB. The sequence listing submitted via EFS-Web is part of the specification and is herein incorporated by reference in its entirety.

SEQUENCE LISTING

Incorporated by reference in its entirety herein is a computer-readable nucleotide/amino acid sequence listing submitted concurrently herewith and identified as follows: one xxx Bytes ASCII (Text) file named "filename.txt," created on Jul. 22, 2014.

FIELD OF INVENTION

In some aspects, the present invention relates to pharmaceutical compositions and methods of using the same to treat leukemia. More particularly, the present invention relates to compositions comprising dispersions of thienotriazolodiazepine compounds which have improved solubility and bioavailability and methods for treating a BCR-ABL positive acute lymphoblastic leukemia and/or a CD34 positive acute myeloid leukemia.

BACKGROUND OF THE INVENTION

The compound of Formula (1), described herein below, has been shown to inhibit the binding of acetylated histone H4 to the tandem bromodomain (BRD)-containing family of transcriptional regulators known as the BET (bromodomains and extraterminal) proteins, which include BRD2, BRD3, and BRD4. See U.S. Patent Application Publication No. 2010/0286127 A1, which is incorporated herein by reference in its entirety. The BET proteins have emerged as major epigenetic regulators of proliferation and differentiation and also have been associated with predisposition to dyslipidemia or improper regulation of adipogenesis, elevated inflammatory profile and risk for cardiovascular disease and type 2 diabetes, and increased susceptibility to autoimmune diseases such as rheumatoid arthritis and systemic lupus erythematosus as reported by Denis, G. V. "Bromodomain coactivators in cancer, obesity, type 2 diabetes, and inflammation," *Discov Med* 2010; 10:489-499, which is incorporated herein by reference in its entirety. Accordingly, the compound of formula (II) may be useful for treatment of various cancers, cardiovascular disease, type 2 diabetes, and autoimmune disorders such as rheumatoid arthritis and systemic lupus erythematosus.

The thienotriazolodiazepine compound of Formula (1), described herein below, presents highly specific difficulties in relation to administration generally and the preparation of galenic compositions in particular, including the particular problems of drug bioavailability and variability in inter- and intra-patient dose response, necessitating development of a non-conventional dosage form with respect to the practically water-insoluble properties of the thienotriazolodiazepine.

Previously, it had been found that thienotriazolodiazepine compound of Formula (1) could be formulated with the carrier ethyl acrylate-methyl methacrylate-trimethylammonioethyl methacrylate chloride copolymer (Eudragit RS, manufactured by Rohm) to provide an oral formulation that preferentially released the pharmaceutical ingredient in the lower intestine for treatment of inflammatory bowel diseases such as ulcerative colitis and Crohn's disease as reported in U.S. Patent Application Publication No. 20090012064 A1, which is incorporated herein by reference in its entirety. Through various experiments including animal tests, it was found that that for inflammatory bowel diseases, the thienotriazolodiazepine compound of Formula (1) release in a lesion and a direct action thereof on the inflammatory lesion were more important than the absorption of thienotriazolodiazepine compound of Formula (1) into circulation from the gastrointestinal tract. However, for many other disease conditions high absorption of thienotriazolodiazepine compound of Formula (1) into the circulation from gastrointestinal tract is required. Accordingly, a need exists for formulations of thienotriazolodiazepine compound of Formula (1) that can provide high absorption of thienotriazolodiazepine compound of Formula (1) into the circulation from gastrointestinal tract.

BRIEF SUMMARY OF THE INVENTION

In one embodiment, the present invention provides for a method of treating an acute lymphoblastic leukemia comprising administering to a patient a pharmaceutically acceptable amount of a composition comprising a thienotriazolodiazepine compound, said thienotriazolodiazepine compound being represented by the following Formula (1):

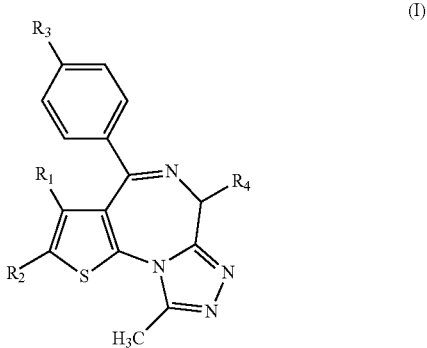

(I)

wherein $R_1$ is alkyl having a carbon number of 1-4, $R_2$ is a hydrogen atom; a halogen atom; or alkyl having a carbon number of 1-4 optionally substituted by a halogen atom or a hydroxyl group, $R_3$ is a halogen atom; phenyl optionally substituted by a halogen atom, alkyl having a carbon number of 1-4, alkoxy having a carbon number of 1-4 or cyano; —$NR_5$—$(CH_2)_m$—$R_6$ wherein $R_5$ is a hydrogen atom or alkyl having a carbon number of 1-4, m is an integer of 0-4, and $R_6$ is phenyl or pyridyl optionally substituted by a halogen atom; or —$NR_7$—CO—$(CH_2)_n$—$R_8$ wherein $R_7$ is a hydrogen atom or alkyl having a carbon number of 1-4, n is an integer of 0-2, and $R_8$ is phenyl or pyridyl optionally substituted by a halogen atom, and $R_4$ is —$(CH_2)_a$—CO—

NH—R$_9$ wherein a is an integer of 1-4, and R$_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —(CH$_2$)$_b$—COOR$_{10}$ wherein b is an integer of 1-4, and R$_{10}$ is alkyl having a carbon number of 1-4, or a pharmaceutically acceptable salt thereof or a hydrate or solvate thereof, wherein the thienotriazolodiazepine compound is formed as a solid dispersion comprising an amorphous thienotriazolodiazepine compound wherein the solid dispersion exhibits an X-ray powder diffraction pattern substantially free of diffraction lines associated with crystalline thienotriazolodiazepine compound of Formula (1) and a pharmaceutically acceptable polymer. In one such embodiment, the pharmaceutically acceptable polymer is hydroxypropylmethylcellulose acetate succinate having a thienotriazolodiazepine compound to hydroxypropylmethylcellulose acetate succinate (HPMCAS), weight ratio of 1:3 to 1:1.

In one embodiment, the thienotriazolodiazepine compound represented by Formula 1 is independently selected from the group consisting of: (i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, (ii) methyl (S)-{4-(3'-cyanobiphenyl-4-yl)-2,3,9-trimethyl-6H-thieno[3,2-f][1,2,4]tri-azolo[4,3-a][1,4]diazepin-6-yl}acetate, (iii) methyl (S)-{2,3,9-trimethyl-4-(4-phenylaminophenyl)-6H-thieno[3,2-f][1,2,4]triaz-olo[4,3-a][1,4]diazepin-6-yl}acetate; and (iv) methyl (S)-{2,3,9-trimethyl-4-[4-(3-phenylpropionylamino)phenyl]-6H-thieno[3,2-f-][1,2,4]triazolo[4,3-a][1,4]diazepin-6-yl}acetate.

In another embodiment, the thienotriazolodiazepine compound is (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl)acetamide dihydrate.

In still yet another embodiment, the solid dispersion exhibits a single glass transition temperature (Tg) inflection point ranging from about 130° C. to about 140° C.

The present disclosure further provides for an embodiment providing for a method of treating an acute myeloid leukemia comprising the step of administering to a patient a pharmaceutically acceptable amount of a composition comprising a thienotriazolodiazepine compound, said thienotriazolodiazepine compound being represented by the following Formula (1):

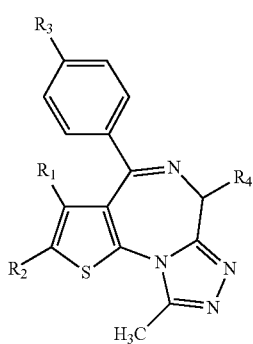

(I)

wherein R$_1$ is alkyl having a carbon number of 1-4, R$_2$ is a hydrogen atom; a halogen atom; or alkyl having a carbon number of 1-4 optionally substituted by a halogen atom or a hydroxyl group, R$_3$ is a halogen atom; phenyl optionally substituted by a halogen atom, alkyl having a carbon number of 1-4, alkoxy having a carbon number of 1-4 or cyano; —NR$_5$—(CH$_2$)$_m$—R$_6$ wherein R$_5$ is a hydrogen atom or alkyl having a carbon number of 1-4, m is an integer of 0-4, and R$_6$ is phenyl or pyridyl optionally substituted by a halogen atom; or —NR$_7$—CO—(CH$_2$)$_n$—R$_8$ wherein R$_7$ is a hydrogen atom or alkyl having a carbon number of 1-4, n is an integer of 0-2, and R$_8$ is phenyl or pyridyl optionally substituted by a halogen atom, and R$_4$ is —(CH$_2$)$_a$—CO—NH—R$_9$ wherein a is an integer of 1-4, and R$_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —(CH$_2$)$_b$—COOR$_{10}$ wherein b is an integer of 1-4, and R$_{10}$ is alkyl having a carbon number of 1-4, or a pharmaceutically acceptable salt thereof or a hydrate or solvate thereof, wherein the thienotriazolodiazepine compound is formed as a solid dispersion comprising an amorphous thienotriazolodiazepine compound wherein the solid dispersion exhibits an X-ray powder diffraction pattern substantially free of diffraction lines associated with crystalline thienotriazolodiazepine compound of Formula (1) and a pharmaceutically acceptable polymer. In one such embodiment, the pharmaceutically acceptable polymer is hydroxypropylmethylcellulose acetate succinate having a thienotriazolodiazepine compound to hydroxypropylmethylcellulose acetate succinate (HPMCAS), weight ratio of 1:3 to 1:1.

In one embodiment, the thienotriazolodiazepine compound represented by Formula 1 is independently selected from the group consisting of: (i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, (ii) methyl (S)-{4-(3'-cyanobiphenyl-4-yl)-2,3,9-trimethyl-6H-thieno[3,2-f][1,2,4]tri-azolo[4,3-a][1,4]diazepin-6-yl}acetate, (iii) methyl (S)-{2,3,9-trimethyl-4-(4-phenylaminophenyl)-6H-thieno[3,2-f][1,2,4]triaz-olo[4,3-a][1,4]diazepin-6-yl}acetate; and (iv) methyl (S)-{2,3,9-trimethyl-4-[4-(3-phenylpropionylamino)phenyl]-6H-thieno[3,2-f-][1,2,4]triazolo[4,3-a][1,4]diazepin-6-yl}acetate.

In another embodiment, the thienotriazolodiazepine compound is (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl)acetamide dihydrate.

In one embodiment, the solid dispersion exhibits an X-ray powder diffraction pattern substantially free of diffraction lines associated with crystalline thienotriazolodiazepine compound of Formula (1). In still yet another embodiment, the solid dispersion exhibits a single glass transition temperature (Tg) inflection point ranging from about 130° C. to about 140° C.

In one aspect, the present invention provides a method of treating a BCR-ABL positive acute lymphoblastic leukemia comprises the step of administering to a patient a pharmaceutically acceptable amount of a composition comprising a thienotriazolodiazepine compound. In some preferred embodiments of the method of treating a BCR-ABL positive acute lymphoblastic leukemia, the thienotriazolodiazepine compound is represented by the structure of Formula (1):

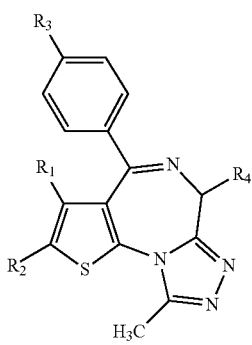

(I)

wherein R$_1$ is alkyl having a carbon number of 1-4; R$_2$ is a hydrogen atom; a halogen atom; or alkyl having a carbon number of 1-4 optionally substituted by a halogen atom or a hydroxyl group; R$_3$ is a halogen atom; a phenyl optionally substituted by a halogen atom, alkyl having a carbon number of 1-4, alkoxy having a carbon number of 1-4 or cyano; —NR$_5$—(CH$_2$)$_m$—R$_6$ wherein R$_5$ is a hydrogen atom or alkyl having a carbon number of 1-4, m is an integer of 0-4, and R$_6$ is phenyl or pyridyl optionally substituted by a halogen atom; or —NR$_7$—CO—(CH$_2$)$_n$—R$_8$ wherein R$_7$ is a hydrogen atom or alkyl having a carbon number of 1-4, n is an integer of 0-2, and R$_8$ is phenyl or pyridyl optionally substituted by a halogen atom, and R$_4$ is —(CH$_2$)$_a$—CO—NH—R$_9$ wherein a is an integer of 1-4, and R$_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —(CH$_2$)$_b$—COOR$_{10}$ wherein b is an integer of 1-4, and R$_{10}$ is alkyl having a carbon number of 1-4, or a pharmaceutically acceptable salt thereof or a hydrate or solvate thereof.

In some preferred embodiments of the method of treating a BCR-ABL positive acute lymphoblastic leukemia, the thienotriazolodiazepine compound represented by Formula 1 is independently selected from the group consisting of:

(i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, (ii) methyl (S)-{4-(3'-cyanobiphenyl-4-yl)-2,3,9-trimethyl-6H-thieno[3,2-f][1,2,4]triazolo[4,3-a][1,4]diazepin-6-yl}acetate, (iii) methyl (S)-{2,3,9-trimethyl-4-(4-phenylaminophenyl)-6H-thieno[3,2-f][1,2,4]triazolo[4,3-a][1,4]diazepin-6-yl}acetate; and (iv) methyl (S)-{2,3,9-trimethyl-4-[4-(3-phenylpropionylamino)phenyl]-6H-thieno[3,2-f-][1,2,4]triazolo[4,3-a][1,4]diazepin-6-yl}acetate.

In some preferred embodiments of the method of treating a BCR-ABL positive acute lymphoblastic leukemia, the thienotriazolodiazepine compound represented by Formula 1 is (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl)acetamide dihydrate.

In some preferred embodiments of the method of treating a BCR-ABL positive acute lymphoblastic leukemia, the thienotriazolodiazepine compound represented by Formula 1 is formed as a solid dispersion comprising an amorphous thienotriazolodiazepine compound of the Formula (1) and a pharmaceutically acceptable salt thereof or a hydrate thereof; and a pharmaceutically acceptable polymer.

In some preferred embodiments of the method of treating a BCR-ABL positive acute lymphoblastic leukemia, the thienotriazolodiazepine compound represented by Formula 1 is formed as a solid dispersion comprising an amorphous thienotriazolodiazepine compound of the Formula (1) and a pharmaceutically acceptable salt thereof or a hydrate thereof; and a pharmaceutically acceptable polymer, wherein the pharmaceutically acceptable polymer is hydroxypropylmethylcellulose acetate succinate having a thienotriazolodiazepine compound to hydroxypropylmethylcellulose acetate succinate (HPMCAS), weight ratio of 1:3 to 1:1.

In some preferred embodiments of the method of treating a BCR-ABL positive acute lymphoblastic leukemia, the solid dispersion comprising the thienotriazolodiazepine compound represented by Formula 1, exhibits a single glass transition temperature (Tg) inflection point ranging from about 130° C. to about 140° C. In one embodiment, the solid dispersion exhibits an X-ray powder diffraction pattern substantially free of diffraction lines associated with crystalline thienotriazolodiazepine compound of Formula (1).

In another aspect, the present invention provides a method of treating a CD34 positive acute myeloid leukemia. In some exemplary embodiments of the method of treating a CD34 positive acute myeloid leukemia, the method comprises administering to a patient a pharmaceutically acceptable amount of a composition comprising a thienotriazolodiazepine compound. In some preferred embodiments of the method of treating a CD34 positive acute myeloid leukemia, the method comprises administering to a patient a pharmaceutically acceptable amount of a composition comprising a thienotriazolodiazepine compound having the structure of Formula (1):

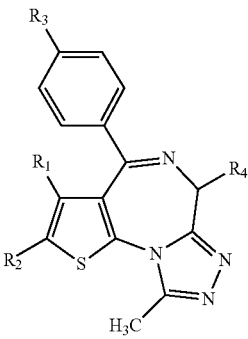

(I)

wherein R$_1$ is alkyl having a carbon number of 1-4, R$_2$ is a hydrogen atom; a halogen atom; or alkyl having a carbon number of 1-4 optionally substituted by a halogen atom or a hydroxyl group, R$_3$ is a halogen atom; phenyl optionally substituted by a halogen atom, alkyl having a carbon number of 1-4, alkoxy having a carbon number of 1-4 or cyano; —NR$_5$—(CH$_2$)$_m$—R$_6$ wherein R$_5$ is a hydrogen atom or alkyl having a carbon number of 1-4, m is an integer of 0-4, and R$_6$ is phenyl or pyridyl optionally substituted by a halogen atom; or —NR$_7$—CO—(CH$_2$)$_n$—R$_8$ wherein R$_7$ is a hydrogen atom or alkyl having a carbon number of 1-4, n is an integer of 0-2, and R$_8$ is phenyl or pyridyl optionally substituted by a halogen atom, and R$_4$ is —(CH$_2$)$_a$—CO—NH—R$_9$ wherein a is an integer of 1-4, and R$_9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —($CH_2$)$_b$—COOR$_{10}$ wherein b is an integer of 1-4, and R$_{10}$ is alkyl having a carbon number of 1-4, or a pharmaceutically acceptable salt thereof or a hydrate or solvate thereof.

In some preferred embodiments of the method of treating a CD34 positive acute myeloid leukemia, the thienotriazolodiazepine compound represented by Formula 1 is independently selected from the group consisting of:

(i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, (ii) methyl (S)-{4-(3'-cyanobiphenyl-4-yl)-2,3,9-trimethyl-6H-thieno[3,2-f][1,2,4]triazolo[4,3-a][1,4]diazepin-6-yl}acetate, (iii) methyl (S)-{2,3,9-trimethyl-4-(4-phenylaminophenyl)-6H-thieno[3,2-f][1,2,4]triazolo[4,3-a][1,4]diazepin-6-yl}acetate; and (iv) methyl (S)-{2,3,9-trimethyl-4-[4-(3-phenylpropionylamino)phenyl]-6H-thieno[3,2-f-][1,2,4]triazolo[4,3-a][1,4]diazepin-6-yl}acetate.

In some preferred embodiments of the method of treating a CD34 positive acute myeloid leukemia, the thienotriazolodiazepine compound represented by Formula 1 is (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl) acetamide dihydrate.

In some preferred embodiments of the method of treating a CD34 positive acute myeloid leukemia, the thienotriazolodiazepine compound represented by Formula 1 is formed as a solid dispersion comprising an amorphous thienotriazolodiazepine compound of the Formula (1) and a pharmaceutically acceptable salt thereof or a hydrate thereof; and a pharmaceutically acceptable polymer. In one embodiment, the solid dispersion exhibits an X-ray powder diffraction pattern substantially free of diffraction lines associated with crystalline thienotriazolodiazepine compound of Formula (1).

In some preferred embodiments, the method of treating a CD34 positive acute myeloid leukemia comprises administering to a patient a pharmaceutically acceptable amount of an amorphous thienotriazolodiazepine compound of the Formula (1) and a pharmaceutically acceptable salt thereof or a hydrate thereof, wherein thienotriazolodiazepine compound of the Formula (1) is formed as a solid dispersion comprising an amorphous thienotriazolodiazepine compound of the Formula (1) and a pharmaceutically acceptable salt thereof or a hydrate thereof; and a pharmaceutically acceptable polymer, and wherein the pharmaceutically acceptable polymer is hydroxypropylmethylcellulose acetate succinate having a thienotriazolodiazepine compound to hydroxypropylmethylcellulose acetate succinate (HPMCAS), weight ratio of 1:3 to 1:1.

In some preferred embodiments, the method of treating a CD34 positive acute myeloid leukemia comprises administering to a patient a pharmaceutically acceptable amount of an amorphous thienotriazolodiazepine compound of the Formula (1) and a pharmaceutically acceptable salt thereof or a hydrate thereof formed in a solid dispersion in a pharmaceutically acceptable polymer, wherein the solid dispersion exhibits a single glass transition temperature (Tg) inflection point ranging from about 130° C. to about 140° C. In one embodiment, the solid dispersion exhibits an X-ray powder diffraction pattern substantially free of diffraction lines associated with crystalline thienotriazolodiazepine compound of Formula (1).

BRIEF DESCRIPTION OF THE DRAWINGS

The foregoing summary, as well as the following detailed description of embodiments of the pharmaceutical compositions including thienotriazolodiazepine formulations and methods of the present invention, will be better understood when read in conjunction with the appended drawings of exemplary embodiments. It should be understood, however, that the invention is not limited to the precise arrangements and instrumentalities shown.

In the drawings:

FIGS. 14A-14D illustrate kinetics of apoptosis induced by compound (1-1) in AML cell lines: HL60, K562, KG1 and KG1a cells, which were harvested at different time points after treatment. Apoptotic cells were defined as annexin V+ with or without PI uptake. X-axis, indicates doses of compound (1-1) and Y-axis indicates percentage of apoptotic cells. One representative experiment of two is shown.

FIGS. 17A-17C illustrate BRD gene expression in leukemia cell lines and patient samples. Expression levels of BRD2, BRD3 and BRD4 in leukemia cell lines (FIG. 17A) and patient samples from ALL (FIG. 17B) and AML (FIG. 17C). X-axis indicates cell lines and Y-axis, indicates cDNA quantities, relative to ABL. CD34+ cells were obtained by positive selection with magnetic beads.

FIGS. 19A-19D illustrate cDNA kinetics of BRD2, BRD3, BRD4 after treatment with Compound (1-1). cDNA extractions were obtained from different ALL and AML cell lines. Expression levels were studied by QT-PCR.

FIG. 20 illustrates Compound (1-1) effects on primary cells. CD34+ and CD34− cord blood cells and AML cells were obtained by positive selection with magnetic antibody-labeled beads. Cells were treated with different doses of Compound (1-1) and harvested after 24 hours. The Y-axis depicts annexin V with or without PI uptake.

FIGS. 32A-32C show apoptosis patterns in AML patients after treatment with Compound (1-1).

FIGS. 33A-33G show apoptosis patterns in AML patients.

FIGS. 40A-40H illustrate cell cycle alterations induced by with Compound (1-1) (OTX015) in leukemia cell lines. Representative histograms of flow cytometry profiles of RS4-11 cells treated with increasing doses of OTX015 for 48 h are shown FIGS. 40A-40F. Cells were incubated 1 h with PI prior to cell cycle analysis. Cell cycle alterations for all AML and ALL cell lines were analyzed at 48 h in FIG. 40G. X-axis indicates cell lines and Y-axis indicates percentage of cells in G1 and S-phase. Results are shown with mean±SD from duplicates of three independent experiments.

FIGS. 41C-41H illustrate modulation of BRD4, BRD2 and BRD3 at the cDNA level by OTX015 treatment at 250 nM and 500 nM respectively at 48 h. Significant upregulation of BRD3 and BRD2 in KG1, K562 and Jurkat and increase of BRD2 in KG1 and HL60 were detected. Gene expression levels of BRD4, BRD2, and BRD3 in leukemia cell lines at baseline levels are shown in FIGS. 41A and 41B. Gene expression levels after 48 h exposure to OTX015 at 250 nM and 500 nM: of BRD4 (FIGS. 41C and 41D), of BRD3 (FIGS. 41E and 41F), and of BRD2 (FIGS. 41G and 41H). X-axis indicates cell lines and Y-axis indicates cDNA quantities, relative to ABL. Results are shown with mean±SD from duplicates of two independent experiments.

FIGS. 43A-43L illustrate effects of OTX015 at the protein level for BRD 4, BRD2 and BRD 3 as well as c-MYC. In the selected AML cell line HL60 BRD4 and BRD3 remained unaffected after 72 h OTX015 exposure at 500 nM with a transient downregulation of c-MYC observed after 24 h-treatment (FIG. 43A-43C) while the almost resistant AML cell line K562 displayed downregulation of BRD4, BRD3 and c-MYC starting after 24 h exposure (FIG. 43D-43F). For the sensitive ALL cell lines, Jurkat displayed c-MYC downregulation at 48 h and 72 h (FIG. 43G-43I) while BRD4, BRD3 and c-MYC remained unaffected in RS4-11 (FIG. 4JD-43L). AML cell lines HL60, K562 (FIGS. 43A-43C; FIG. 43D-43F) and ALL cell lines Jurkat and RS4-11 (FIG. 43G-43I; FIG. 4JD-43L) were treated with OTX015 at 500 nM and compared to controls exposed to according DMSO. At indicated time-points proteins were extracted and immunoblotted with BRD4, BRD3, BRD2 or c-MYC antibodies after gel electrophoresis. Blots were revealed for BRD4, BRD3, c-MYC and GAPDH either with the ODYSSEY (LiCor) technique which allows exact quantification of proteins related to GAPDH or BRD2 which was revealed by chemiluminescence. This technique did not allow protein quantification. One representative experiment out of three is shown.

FIGS. 44A-44D show effects of OTX015 on primary patient cells. 5 samples from AML patients and 2 ALL, including 1 ALL Ph+ patient, were treated ex vivo with OTX015. Patient characteristics are shown in FIG. 44D. OTX015 induced apoptosis in primary AML patient samples at various degrees ranging from 35-85% (FIG. 6). The Ph+ ALL patient appeared to be resistant. OTX015 induced apoptosis in primary cells of the AML and ALL patients. Mononuclear cells were obtained from bone marrow (BM) or peripheral blood (PB) from AML and ALL patients. Cells were exposed 72 h with 250 and 500 nM of OTX015 and apoptosis was assessed by annexin V and PI staining. Results are shown with means±SD from duplicates of one experiment.

FIGS. 45A-45E illustrate modulation of c-MYC at the protein level in a patient sample. Protein extracts were obtained from bone marrow (BM) cells of patient 5 (FIG. 44D; FIGS. 45A-45D) upon ex vivo treatment with 250 and 500 nM of OTX015 respectively. The BM cells displayed downregulation of c-MYC after 72 h exposure to OTX015. Bone marrow cells from patient 5 were treated with OTX015 at 250 nM and 500 nM and compared to controls exposed to according concentrations with DMSO. Proteins were extracted at 72 h and immunoblotted with appropriate c-MYC antibodies after gel electrophoresis. Blots were revealed with the ODYSSEY (LiCor) technique which allowed exact quantification of proteins related to GAPDH (FIG. 45A). Expression level of cMYC relative to ABL were realised by RQ-PCR at three time points 24, 48 and 72 h (FIG. 45B). Results in FIG. 45B are shown with means±SD from duplicates.

FIG. 46 illustrates a summary of biological effects of OTX015.

FIGS. 47A-47D illustrate basal gene expression of BRD2, BRD3 and BRD4 in patient samples as assessed by RQ-PCR analysis. Among ALL patients, Ph+ ALL showed lower BRD expression levels (FIGS. 47A and 47B; patients 3 to 6 in FIG. 47E) while BRD expression levels among AML patients were more heterogeneous (FIGS. 47C and 47D).

FIG. 47E provides a summary of characteristics of the patients whose samples were assessed to give the results in FIGS. 47A-47D.

DETAILED DESCRIPTION OF THE INVENTION

Figure 1A:
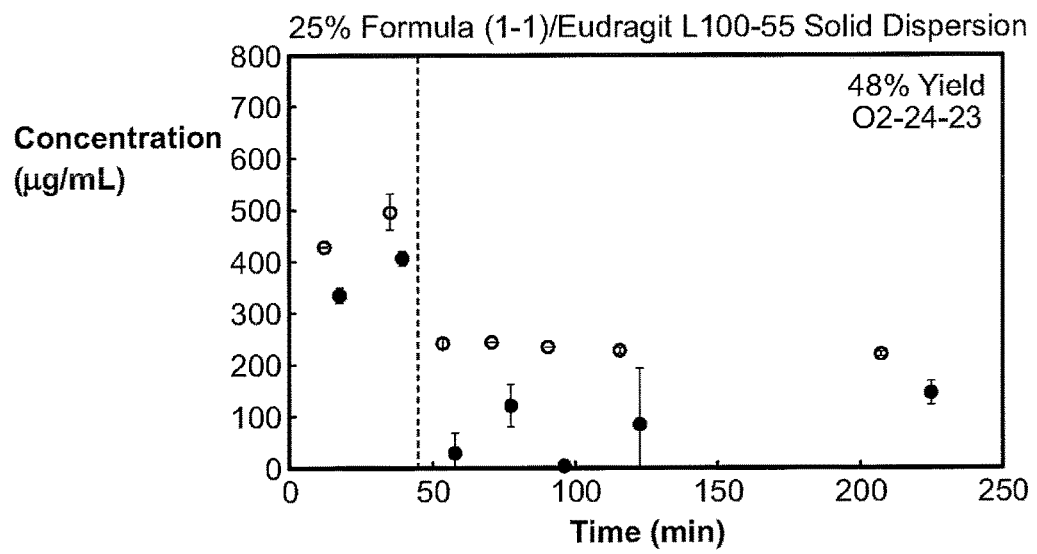
FIG. 1A illustrates dissolution profile of a comparator formulation comprising a solid dispersion comprising 25% compound (1-1) and Eudragit L100-55.
Figure 1B:
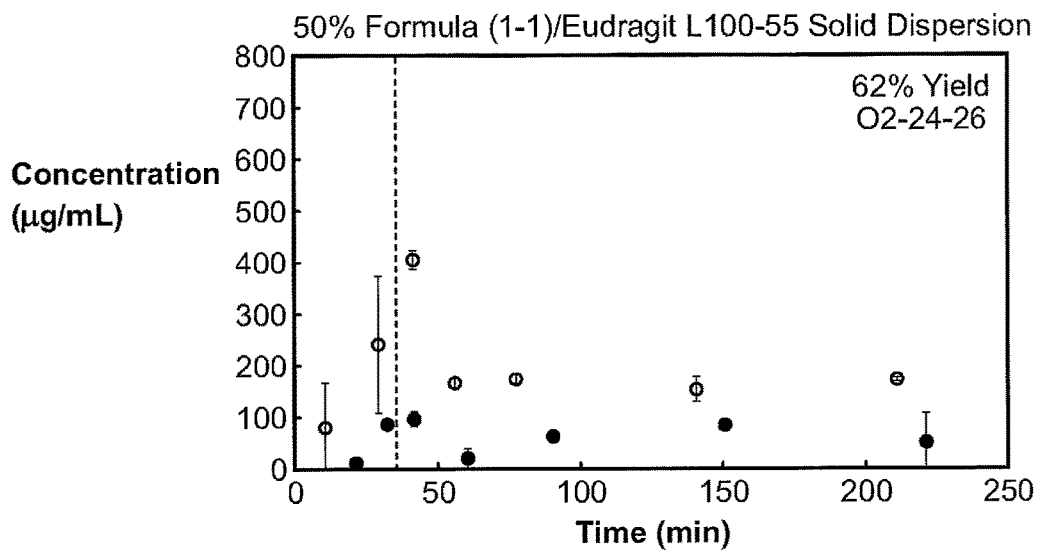
FIG. 1B illustrates dissolution profile of a comparator formulation comprising a solid dispersion comprising 50% compound (1-1) and Eudragit L100-55.
Figure 1C:
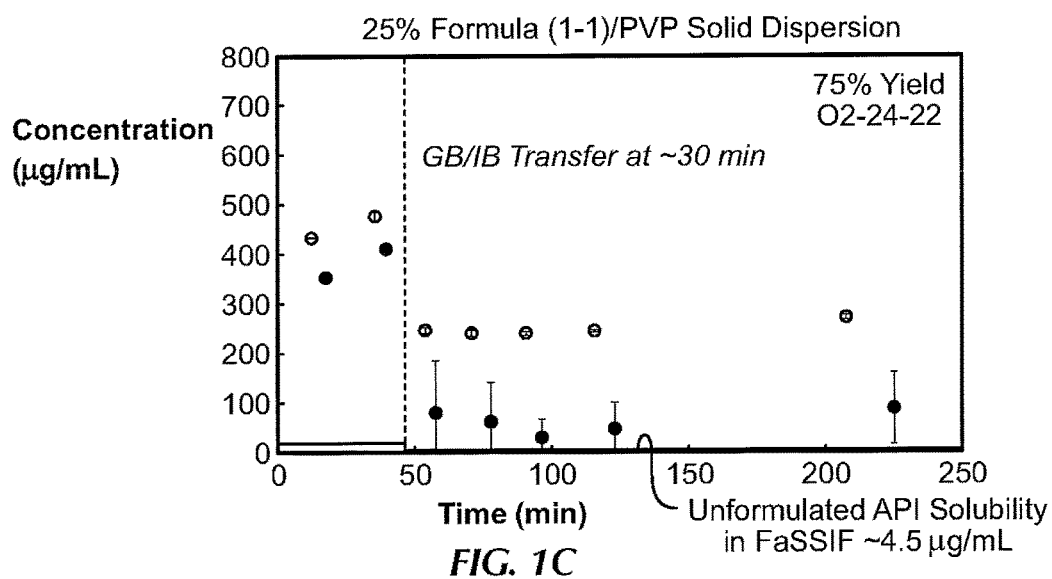
FIG. 1C illustrates dissolution profile of an exemplary formulation comprising a solid dispersion comprising 25% compound (1-1) and polyvinylpyrrolidone (PVP).
Figure 1D:
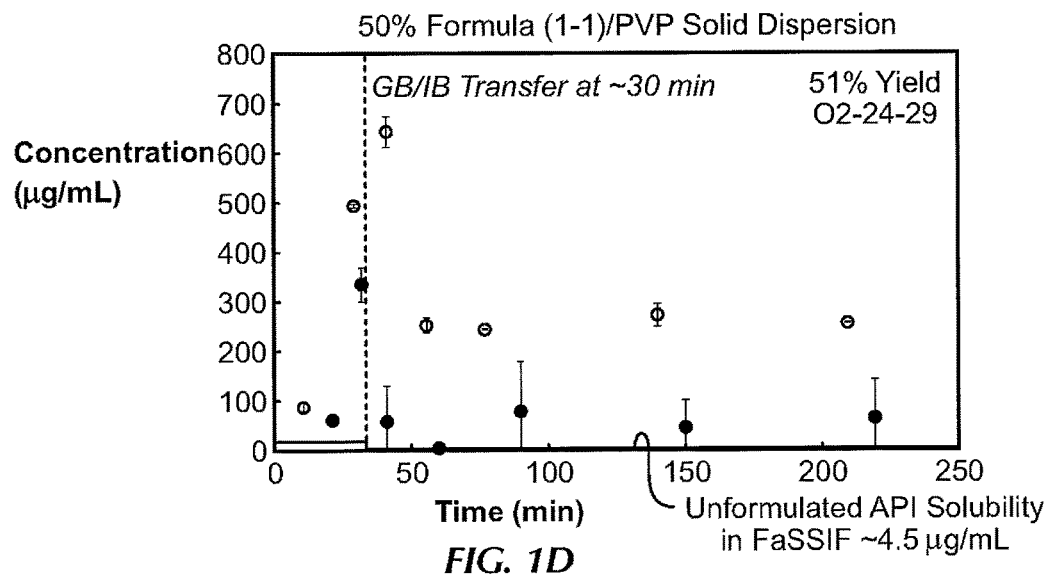
FIG. 1D illustrates dissolution profile of an exemplary formulation comprising a solid dispersion comprising 50% compound (1-1) and PVP.
Figure 1E:
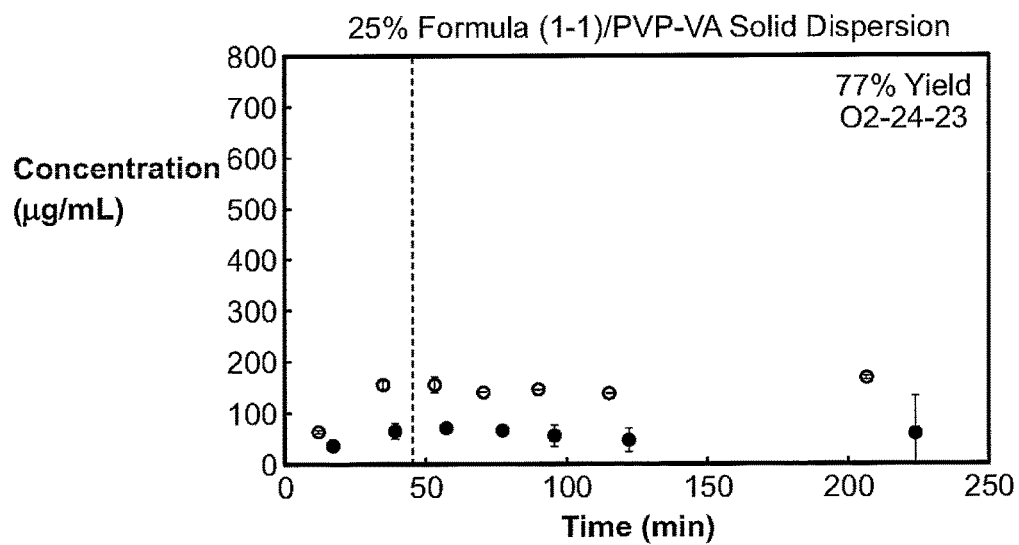
FIG. 1E illustrates dissolution profile of an exemplary formulation comprising a solid dispersion comprising 25% compound (1-1) and PVP-vinyl acetate (PVP-VA).
Figure 1F:
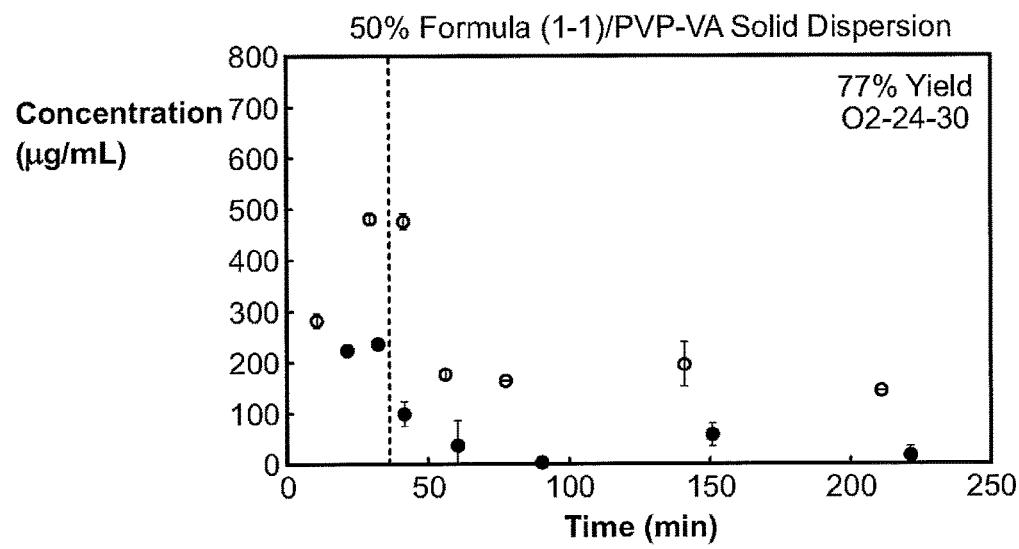
FIG. 1F illustrates dissolution profile of an exemplary formulation comprising a solid dispersion comprising 50% compound (1-1) and PVP-VA.
Figure 1G:
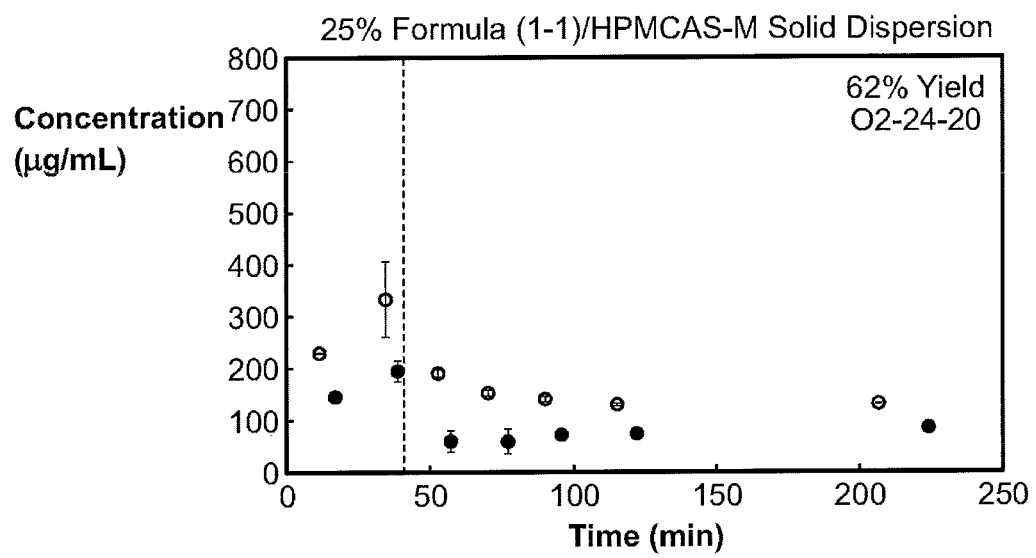
FIG. 1G illustrates dissolution profile of an exemplary formulation comprising a solid dispersion comprising 25% compound (1-1) and hypromellose acetate succinate (HPMCAS-M).
Figure 1H:
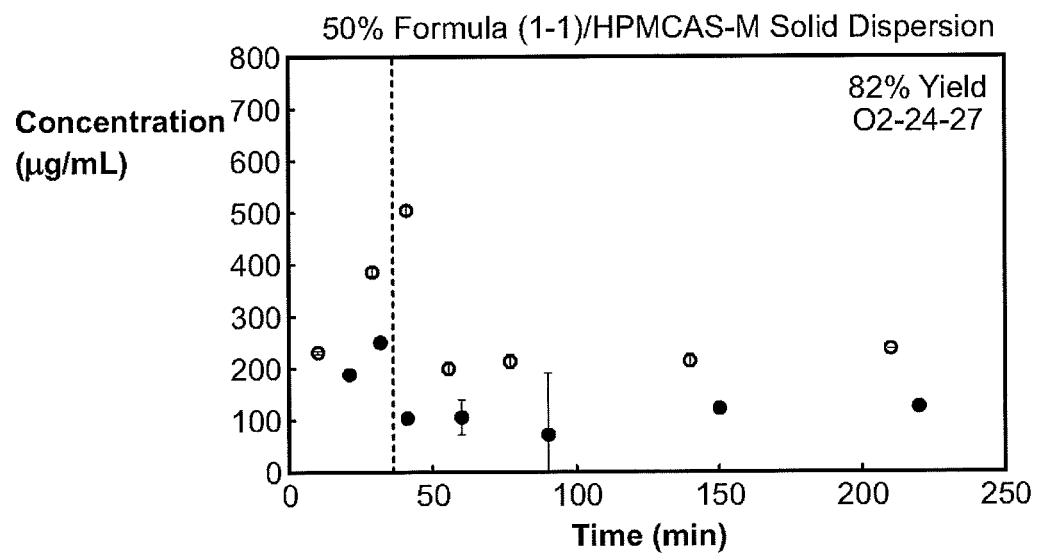
FIG. 1H illustrates dissolution profile of an exemplary formulation comprising a solid dispersion comprising 50% compound (1-1) and HPMCAS-M.
Figure 1I:
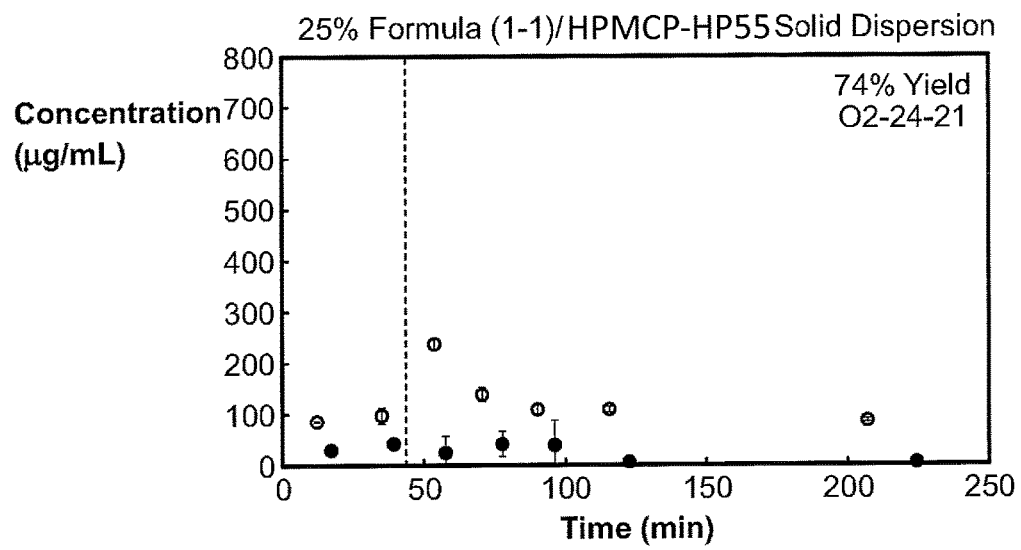
FIG. 1I illustrates dissolution profile of an exemplary formulation comprising a solid dispersion comprising 25% compound (1-1) and hypromellose phthalate (HPMCP-HP55).
Figure 1J:
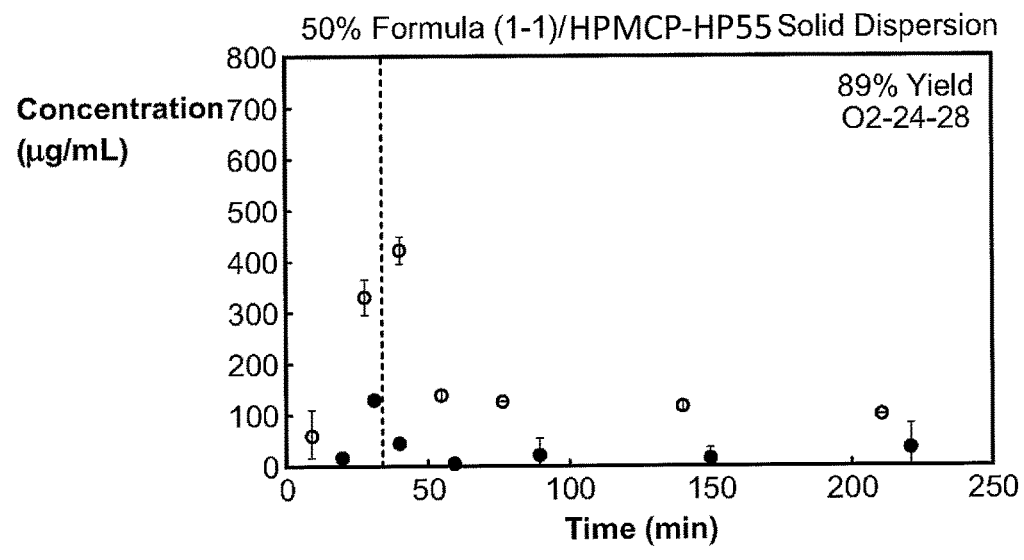
FIG. 1J illustrates dissolution profile of an exemplary formulation comprising a solid dispersion comprising 50% compound (1-1) and HMCP-HP55.

The present subject matter will now be described more fully hereinafter with reference to the accompanying Figures and Examples, in which representative embodiments are shown. The present subject matter can, however, be embodied in different forms and should not be construed as limited to the embodiments set forth herein. Rather, these embodiments are provided to describe and enable one of skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entireties.

The present inventions described herein provide for methods of treating acute lymphoblastic leukemia, acute myeloid leukemia, BCR-ABL positive acute lymphoblastic leukemia and CD34 positive acute myeloid leukemia. The detailed description sets forth the disclosure in various parts: I. Thienotriazolodiazepine Compounds; II. Formulations; III. Dosage Forms; IV. Dosage; V. Process; and VI. Examples. One of skill in the art would understand that each of the various embodiments of methods of treatment include the various embodiments of thienotriazolodiazepine compounds, formulations, dosage forms, dosage and processes described herein.

In one aspect, the present invention provides a method of treating acute lymphoblastic leukemia comprising the step of administering to a patient a pharmaceutically acceptable amount of a composition comprising a thienotriazolodiazepine compound, as described herein, formed as a solid dispersion comprising an amorphous thienotriazolodiazepine compound and a pharmaceutically acceptable salt thereof or a hydrate thereof; and a pharmaceutically acceptable polymer. Various embodiments of such a solid dispersion are described herein and can be used accordingly.

In one aspect, the present invention provides a method of treating acute myeloid leukemia comprising the step of administering to a patient a pharmaceutically acceptable amount of a composition comprising a thienotriazolodiazepine compound, as described herein, formed as a solid dispersion comprising an amorphous thienotriazolodiazepine compound and a pharmaceutically acceptable salt thereof or a hydrate thereof; and a pharmaceutically acceptable polymer. Various embodiments of such a solid dispersion are described herein and can be used accordingly.

In one aspect, the present invention provides a method of treating a BCR-ABL positive acute lymphoblastic leukemia comprising the step of administering to a patient a pharmaceutically acceptable amount of a composition comprising a thienotriazolodiazepine compound according to the various embodiments described herein. In some embodiments of the method of treating a BCR-ABL positive acute lymphoblastic leukemia, the thienotriazolodiazepine compound, as described herein, is formed as a solid dispersion comprising an amorphous thienotriazolodiazepine compound and a pharmaceutically acceptable salt thereof or a hydrate thereof; and a pharmaceutically acceptable polymer. Various embodiments of such a solid dispersion are described herein and can be used accordingly.

In one aspect, the present invention provides a method of treating a CD34 positive acute myeloid leukemia comprising the step of administering to a patient a pharmaceutically acceptable amount of a composition comprising a thienotriazolodiazepine compound according to the various embodiments described herein. In some embodiments of the method of treating a CD34 positive acute myeloid leukemia, the thienotriazolodiazepine compound, as described herein, is formed as a solid dispersion comprising an amorphous thienotriazolodiazepine compound and a pharmaceutically acceptable salt thereof or a hydrate thereof; and a pharmaceutically acceptable polymer. Various embodiments of such a solid dispersion are described herein and can be used accordingly.

I. THIENOTRIAZOLODIAZEPINE COMPOUNDS

In one embodiment, the thienotriazolodiazepine compounds, used in the formulations of the present invention, are represented by Formula (1):

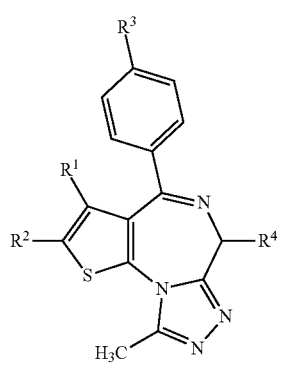

(1)

wherein $R^1$ is alkyl having a carbon number of 1-4, $R^2$ is a hydrogen atom; a halogen atom; or alkyl having a carbon number of 1-4 optionally substituted by a halogen atom or a hydroxyl group, $R^3$ is a halogen atom; phenyl optionally substituted by a halogen atom, alkyl having a carbon number of 1-4, alkoxy having a carbon number of 1-4 or cyano; —$NR^5$—$(CH_2)_m$—$R^6$ wherein $R^5$ is a hydrogen atom or alkyl having a carbon number of 1-4, m is an integer of 0-4, and $R^6$ is phenyl or pyridyl optionally substituted by a halogen atom; or —$NR^7$—CO—$(CH_2)_n$—$R^8$ wherein $R^7$ is a hydrogen atom or alkyl having a carbon number of 1-4, n is an integer of 0-2, and $R^8$ is phenyl or pyridyl optionally substituted by a halogen atom, and $R^4$ is —$(CH_2)_a$—CO—NH—$R^9$ wherein a is an integer of 1-4, and $R^9$ is alkyl having a carbon number of 1-4; hydroxyalkyl having a carbon number of 1-4; alkoxy having a carbon number of 1-4; or phenyl or pyridyl optionally substituted by alkyl having a carbon number of 1-4, alkoxy having a carbon number of 1-4, amino or a hydroxyl group or —$(CH_2)_b$—$COOR^{10}$ wherein b is an integer of 1-4, and $R^{10}$ is alkyl having a carbon number of 1-4, including any salts, isomers, enantiomers, racemates, hydrates, solvates, metabolites, and polymorphs thereof.

In one embodiment, a suitable alkyl group includes linear or branched alkyl radicals including from 1 carbon atom up to 4 carbon atoms. In one embodiment, a suitable alkyl group includes linear or branched alkyl radicals including from 1 carbon atom up to 3 carbon atoms. In one embodiment, a suitable alkyl group includes linear or branched alkyl radicals include from 1 carbon atom up to 2 carbon atoms. In one embodiment, exemplary alkyl radicals include, but are not limited to, methyl, ethyl, propyl, isopropyl, n-butyl, isobutyl, sec-butyl, tert-butyl. In one embodiment, exemplary alkyl groups include, but are not limited to, methyl, ethyl, propyl, isopropyl, 2-methyl-1-propyl, and 2-methyl-2-propyl.

In some embodiments, the present invention provides pharmaceutically acceptable salts, solvates, including hydrates, and isotopically-labeled forms of the thienotriazolodiazepine compounds described herein. In one embodiment, pharmaceutically acceptable salts of the thienotriazolodiazepine compounds include acid addition salts formed with inorganic acids. In one embodiment, pharmaceutically acceptable inorganic acid addition salts of the thienotriazolodiazepine include salts of hydrochloric, hydrobromic, hydroiodic, phosphoric, metaphosphoric, nitric and sulfuric acids. In one embodiment, pharmaceutically acceptable salts of the thienotriazolodiazepine compounds include acid addition salts formed with organic acids. In one embodiment, pharmaceutically acceptable organic acid addition salts of the thienotriazolodiazepine include salts of tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and 4-methyl benzenesulfonic acids.

Representative thienotriazolodiazepine compounds of Formula (1) include, but are not limited to, the thienotriazolodiazepine compounds (1-1) to (1-18), which are listed in the following Table A.

Compound (1-1), of Table A, will be referred to herein as OTX-015 or Y803.

TABLE A
Exemplary compounds of the invention:
(1-1)
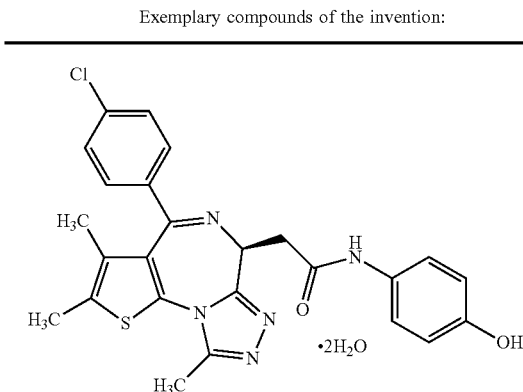
(1-2)
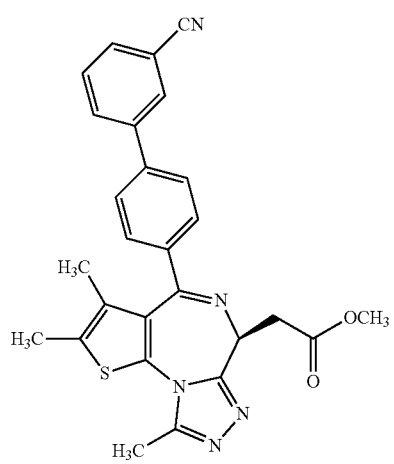 [SMILES: COC(=O)C[C@@H]1N=C(c2ccc(-c3cccc(C#N)c3)cc2)c2c(sc(C)c2C)-n2c(C)nnc21]
(1-3)
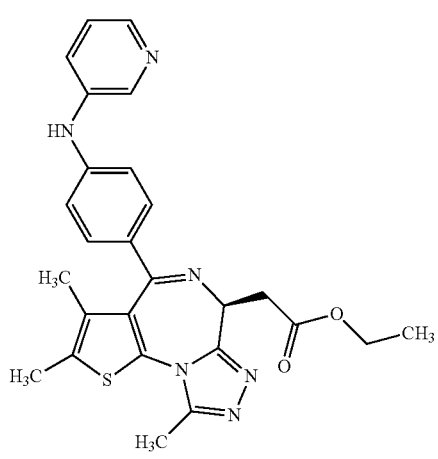 [SMILES: CCOC(=O)C[C@@H]1N=C(c2ccc(Nc3cccnc3)cc2)c2c(sc(C)c2C)-n2c(C)nnc21]
TABLE A-continued
Exemplary compounds of the invention:
(1-4)
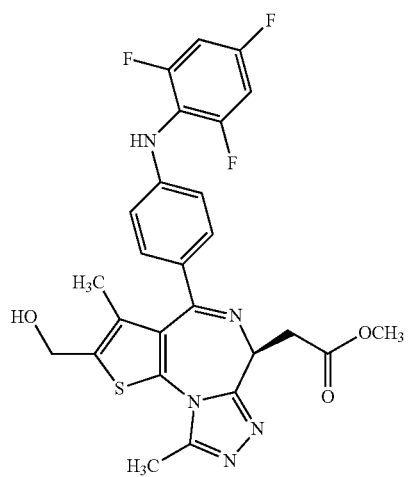 [SMILES: COC(=O)C[C@@H]1N=C(c2ccc(Nc3c(F)cc(F)cc3F)cc2)c2c(sc(CO)c2C)-n2c(C)nnc21]
(1-5)
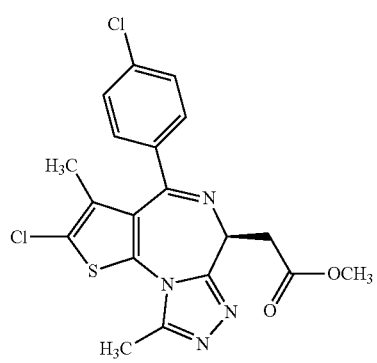 [SMILES: COC(=O)C[C@@H]1N=C(c2ccc(Cl)cc2)c2c(sc(Cl)c2C)-n2c(C)nnc21]
(1-6)
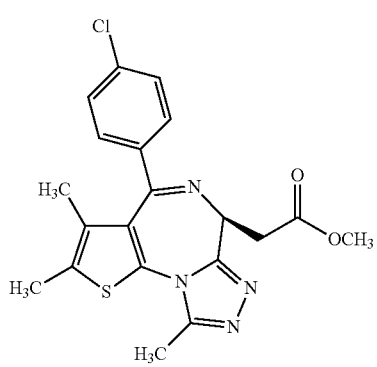 [SMILES: COC(=O)C[C@@H]1N=C(c2ccc(Cl)cc2)c2c(sc(C)c2C)-n2c(C)nnc21]

TABLE A-continued
Exemplary compounds of the invention:
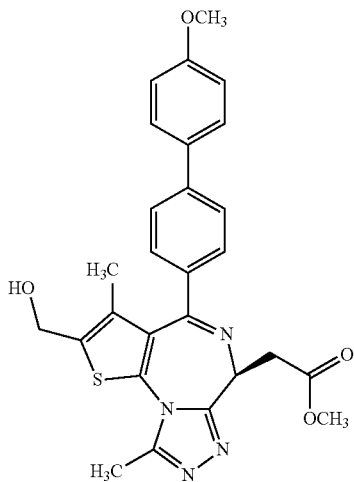 [SMILES: COC(=O)C[C@@H]1N=C(c2ccc(-c3ccc(OC)cc3)cc2)c2c(sc(CO)c2C)-n2c(C)nnc21] (1-7)
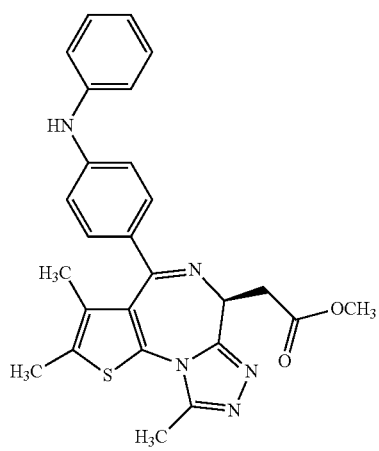 [SMILES: COC(=O)C[C@@H]1N=C(c2ccc(Nc3ccccc3)cc2)c2c(sc(C)c2C)-n2c(C)nnc21] (1-8)
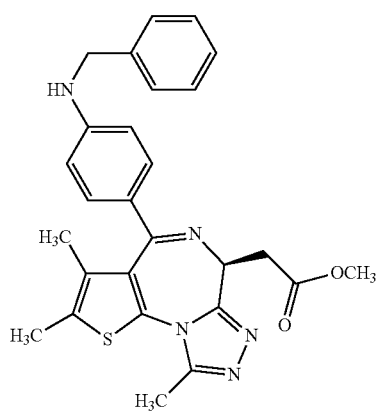 [SMILES: COC(=O)C[C@@H]1N=C(c2ccc(NCc3ccccc3)cc2)c2c(sc(C)c2C)-n2c(C)nnc21] (1-9)
TABLE A-continued
Exemplary compounds of the invention:
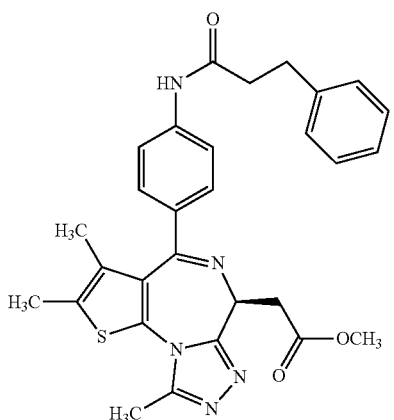 (1-10)
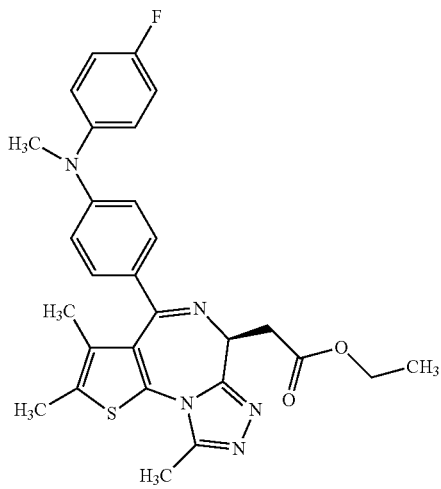 [SMILES: CCOC(=O)C[C@@H]1N=C(c2ccc(N(C)c3ccc(F)cc3)cc2)c2c(sc(C)c2C)-n2c(C)nnc21] (1-11)
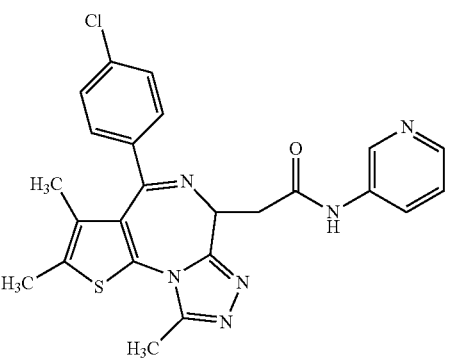 [SMILES: Cc1sc2c(c1C)C(c1ccc(Cl)cc1)=NC(CC(=O)Nc1cccnc1)c1nnc(C)n1-2] (1-12)

TABLE A-continued

Exemplary compounds of the invention:

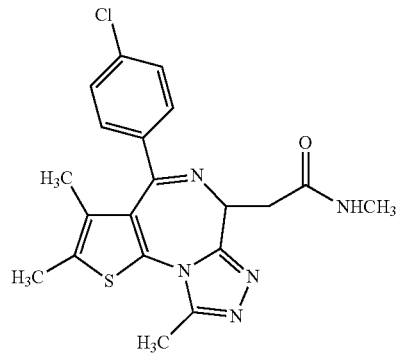 [SMILES: CNC(=O)CC1N=C(c2ccc(Cl)cc2)c2c(sc(C)c2C)-n2c(C)nnc21] (1-13)

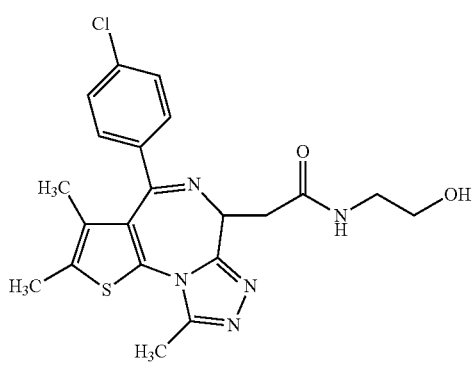 [SMILES: Cc1sc2c(c1C)C(c1ccc(Cl)cc1)=NC(CC(=O)NCCO)c1nnc(C)n1-2] (1-14)

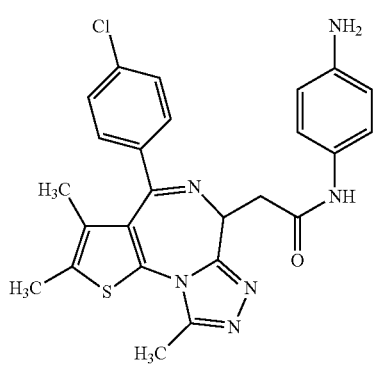 [SMILES: Cc1sc2c(c1C)C(c1ccc(Cl)cc1)=NC(CC(=O)Nc1ccc(N)cc1)c1nnc(C)n1-2] (1-15)

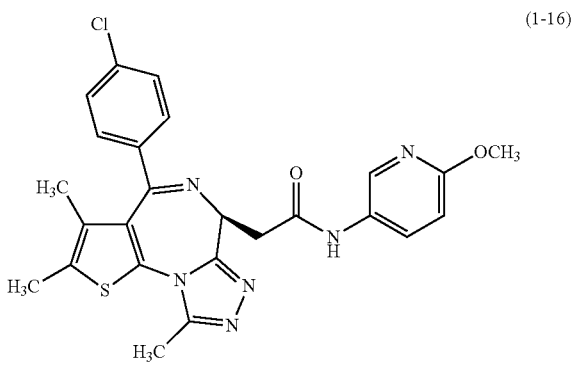 (1-16)

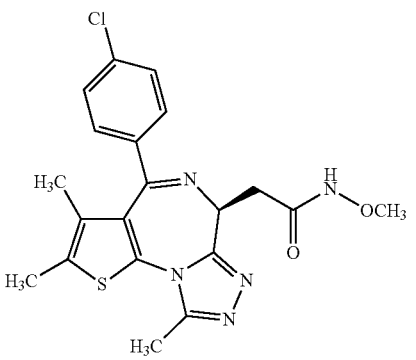 [SMILES: CONC(=O)C[C@@H]1N=C(c2ccc(Cl)cc2)c2c(sc(C)c2C)-n2c(C)nnc21] (1-17)

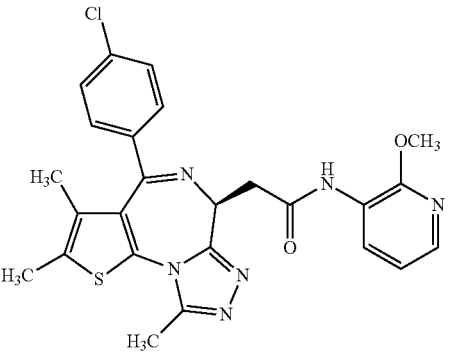 [SMILES: COc1ncccc1NC(=O)C[C@@H]1N=C(c2ccc(Cl)cc2)c2c(sc(C)c2C)-n2c(C)nnc21] (1-18)

In some embodiments, thienotriazolodiazepine compounds of Formula (1) include (i) (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, (ii) methyl (S)-{4-(3'-cyanobiphenyl-4-yl)-2,3,9-trimethyl-6H-thieno[3,2-f][1,2,4]tri-azolo[4,3-a][1,4]diazepin-6-yl}acetate, (iii) methyl (S)-{2,3,9-trimethyl-4-(4-phenylaminophenyl)-6H-thieno[3,2-f][1,2,4]triaz-olo[4,3-a][1,4]diazepin-6-yl}acetate; and (iv) methyl (S)-{2,3,9-trimethyl-4-[4-(3-phenylpropionylamino)phenyl]-6H-thieno[3,2-f-][1,2,4]triazolo[4,3-a][1,4]diazepin-6-yl}acetate.

In some embodiments, thienotriazolodiazepine compounds of Formula (1) include (S)-2-[4-(4-chlorophenyl)-2,3,9-trimethyl-6H-thieno[3,2-f][1,2,-4]triazolo[4,3-a][1,4]diazepin-6-yl]-N-(4-hydroxyphenyl)acetamide dihydrate.

In some embodiments, thienotriazolodiazepine compounds of Formula (1) include (S)-2-[4-(4-chlorophenyl)-2,3,9-trimethyl-6H-thieno[3,2-f][1,2,-4]triazolo[4,3-a][1,4]diazepin-6-yl]-N-(4-hydroxyphenyl)acetamide.

II. FORMULATIONS

The compound of Formula (1) presents highly specific difficulties in relation to administration generally and the preparation of galenic compositions in particular, including the particular problems of drug bioavailability and variability in inter- and intra-patient dose response, necessitating development of a non-conventional dosage form with respect to the practically water-insoluble properties of the compound.

Previously, it had been found that the compound of Formula (1) could be formulated as a solid dispersion with the carrier ethyl acrylate-methyl methacrylate-trimethylammonioethyl methacrylate chloride copolymer (Eudragit RS, manufactured by Rohm) to provide an oral formulation that preferentially released the pharmaceutical ingredient in the lower intestine for treatment of inflammatory bowel diseases such as ulcerative colitis and Crohn's disease (US Patent Application 20090012064 A1, published Jan. 8, 2009). It was found, through various experiments, including animal tests, that in inflammatory bowel diseases drug release in a lesion and a direct action thereof on the inflammatory lesion were more important than the absorption of the drug into circulation from the gastrointestinal tract.

It has now been unexpectedly found that thienotriazolodiazepine compounds, according to Formula (1), pharmaceutically acceptable salts, solvates, including hydrates, racemates, enantiomers isomers, and isotopically-labeled forms thereof, can be formulated as a solid dispersion with pharmaceutically acceptable polymers to provide an oral formulation that provides high absorption of the pharmaceutical ingredient into the circulation from the gastrointestinal tract for treatment of diseases other than inflammatory bowel diseases. Studies in both dogs and humans have confirmed high oral bioavailability of these solid dispersions compared with the Eudragit solid dispersion formulation previously developed for the treatment of inflammatory bowel disease.

Solid dispersions are a strategy to improve the oral bioavailability of poorly water soluble drugs.

The term "solid dispersion" as used herein refers to a group of solid products including at least two different components, generally a hydrophilic carrier and a hydrophobic drug, the thienotriazolodiazepine compounds, according to Formula (1). Based on the drug's molecular arrangement within the dispersion, six different types of solid dispersions can be distinguished. Commonly, solid dispersions are classified as simple eutectic mixtures, solid solutions, glass solution and suspension, and amorphous precipitations in a crystalline carrier. Moreover, certain combinations can be encountered, for example, in the same sample some molecules may be present in clusters while some are molecularly dispersed.

In one embodiment, the thienotriazolodiazepine compounds, according to Formula (1) can be dispersed molecularly, in amorphous particles (clusters). In another embodiment, the thienotriazolodiazepine compounds, according to Formula (1) can be dispersed as crystalline particles. In one embodiment, the carrier can be crystalline. In another embodiment, the carrier can be amorphous.

In one embodiment, the present invention provides a pharmaceutical composition comprising a solid dispersion of a thienotriazolodiazepine compound, in accordance with Formula (1), or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is hypromellose acetate succinate (also called hydroxypropylmethylcellulose acetate succinate or HPMCAS). In one embodiment, the dispersion has a thienotriazolodiazepine compound to hydroxypropylmethylcellulose acetate succinate (HPMCAS) weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1). In some embodiments, the hydroxypropylmethyl cellulose acetate succinates (HPMCAS), may include M grade having 9% acetyl/11% succinoyl (e.g., HPMCAS having a mean particle size of 5 μm (i.e., HPMCAS-MF, fine powder grade) or having a mean particle size of 1 mm (i.e., HPMCAS-MG, granular grade)), H grade having 12% acetyl/6% succinoyl (e.g., HPMCAS having a mean particle size of 5 μm (i.e., HPMCAS-HF, fine powder grade) or having a mean particle size of 1 mm (i.e., HPMCAS-HG, granular grade)), and L grade having 8% acetyl/15% succinoyl (e.g., HPMCAS having a mean particle size of 5 μm (i.e., HPMCAS-LF, fine powder grade) or having a mean particle size of 1 mm (i.e., HPMCAS-LG, granular grade).

In one embodiment, the present invention provides a pharmaceutical composition comprising a solid dispersion of a thienotriazolodiazepine compound of Formula (1) or a pharmaceutically acceptable salt, a solvate, including a hydrate, a racemate, an enantiomer, an isomer, or an isotopically-labeled form thereof in a pharmaceutically acceptable polymer. In one embodiment, the pharmaceutically acceptable polymer is polyvinylpyrrolidone (also called povidone or PVP). In one embodiment, the dispersion has a thienotriazolodiazepine compound to PVP weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to about 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1). In some embodiments, the polyvinyl pyrrolidones may have molecular weights of about 2,500 (Kollidon®12 PF, weight-average molecular weight between 2,000 to 3,000), about 9,000 (Kollidon® 17 PF, weight-average molecular weight between 7,000 to 11,000), about 25,000 (Kollidon® 25, weight-average molecular weight between 28,000 to 34,000), about 50,000 (Kollidon® 30, weight-average molecular weight between 44,000 to 54,000), and about 1,250,000 (Kollidon® 90 or Kollidon® 90F, weight-average molecular weight between 1,000,000 to 1,500,000).

In one embodiment, a pharmaceutical composition of the present invention comprises a solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to about 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1.

In one embodiment, a pharmaceutical composition of the present invention comprises a solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1.

In some embodiments, a pharmaceutical composition comprising a solid dispersion is prepared by spray drying.

In one embodiment, a pharmaceutical composition of the present invention comprises a spray dried solid dispersion of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of compound (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of compound (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 130° C. to 140° C. In some such embodiments, the solid dispersion was exposed to a relative humidity of 75% at 40° C. for at least one month. In other such embodiments, the single Tg occurs at about 135° C. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of an amorphous form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In some embodiments, the solid dispersion exhibits a single inflection for the glass transition temperature (Tg). In some embodiments, the single Tg occurs between 175° C. to 185° C. In some such embodiments, the solid dispersion was exposed to a relative humidity of 75% at 40° C. for at least one month. In other such embodiments, the single Tg occurs at about 179° C. In some embodiments, the solid dispersion exhibits an X-ray powder diffraction pattern substantially free of diffraction lines associated with crystalline thienotriazolodiazepine compound of Formula (1). For the purpose of this application "substantially free" shall mean the absence of a diffraction line, above the amorphous halo, at about 21° 2-theta associated with crystalline thienotriazolodiazepine compound of Formula (1).

In one embodiment, a pharmaceutical composition of the present invention comprises a spray dried solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is hypromellose acetate succinate. In one embodiment, the weight ratio of thienotriazolodiazepine compound of Formula (1) to hypromellose acetate succinate ranges from 1:3 to 1:1.

In one embodiment, a pharmaceutical composition of the present invention comprises a spray dried solid dispersion of a crystalline form of a thienotriazolodiazepine compound of Formula (1) or a pharmaceutically acceptable salt, a solvate, including a hydrate, a racemate, an enantiomer, an isomer, or an isotopically-labeled form thereof and a pharmaceutically acceptable polymer. In one embodiment, the pharmaceutically acceptable polymer is polyvinylpyrrolidone. In one embodiment, the weight ratio of thienotriazolodiazepine compound of Formula (1) to polyvinylpyrrolidone ranges from 1:3 to 1:1.

In one preferred embodiment, the present invention provides a pharmaceutical composition comprising a solid dispersion of 2-[(6S)-4-(4-chlorophenyl)-2,3,9-trimethyl-6H-thienol[3,2-f]-[1,2,4]triazolo[4,3-a][1,4]diazepin-6-yl]-N-(4-hydroxyphenyl)acetamide dihydrate, compound (1-1):

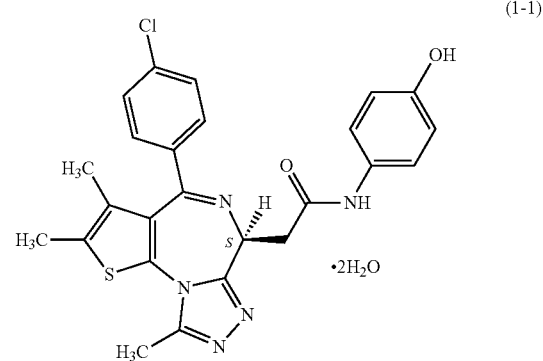

(1-1)

or a pharmaceutically acceptable salt, a solvate, including a hydrate, a racemate, an enantiomer, an isomer, or an isotopically-labeled form and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In another embodiment, the pharmaceutical composition comprises a solid dispersion compound (1-1) or a pharmaceutically acceptable salt, a solvate, including a hydrate, a racemate, an enantiomer, an isomer, or an isotopically-labeled form; and a pharmaceutically acceptable polymer. In one embodiment, the pharmaceutically acceptable polymer is PVP. In one embodiment, the dispersion has compound (1-1) and PVP in a weight ratio 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 175° C. to 185° C. In other such embodiments, the single Tg occurs at about 179° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of an amorphous form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 130° C. to 140° C. In other such embodiments, the single Tg occurs at about 135° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of an amorphous form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is PVP. In one embodiment, the dispersion has compound (1-1) and PVP in a weight ratio 1:3 to 1:1. In one embodiment, at least some portion of the thienotriazolodiazepine compound is homogeneously dispersed throughout the solid dispersion. In another embodiment, the thienotriazolodiazepine compound is homogeneously dispersed throughout the solid dispersion. In one embodiment, the solid dispersion is spray dried. In some embodiments, the solid dispersion exhibits a single inflection for the glass transition temperature (Tg). In some embodiments, the single Tg occurs between 175° C. to 185° C. In other such embodiments, the single Tg occurs at about 189° C. In some such embodiments, the solid dispersion was exposed to a relative humidity of 75% at 40° C. for at least one month. In some embodiments, the solid dispersion exhibits an X-ray powder diffraction pattern substantially free of diffraction lines associated with crystalline thienotriazolodiazepine compound (1-1). For the purpose of this application "substantially free" shall mean the absence of a diffraction line, above the amorphous halo, at about 21° 2-theta associated with crystalline thienotriazolodiazepine compound (1-1).

In one embodiment, a pharmaceutical composition of the present invention comprises a solid dispersion of a crystalline form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is HPMCAS. In one embodiment, the dispersion has compound (1-1) and HPMCAS in a weight ratio of 1:3 to 1:1. In one embodiment, the solid dispersion is spray dried.

In one embodiment, a pharmaceutical composition of the present invention comprises a solid dispersion of a crystalline form of a thienotriazolodiazepine compound (1-1) or a pharmaceutically acceptable salt, a solvate, including a hydrate, a racemate, an enantiomer, an isomer, or an isotopically-labeled form thereof; and a pharmaceutically acceptable polymer. In one embodiment, the pharmaceutically acceptable polymer is PVP. In one embodiment, the dispersion has compound (1-1) and PVP in a weight ratio 1:3 to 1:1. In one embodiment, the solid dispersion is spray dried.

The solid dispersions of the invention, described herein, exhibit especially advantageous properties when administered orally. Examples of advantageous properties of the solid dispersions include, but are not limited to, consistent and high level of bioavailability when administered in standard bioavailability trials in animals or humans. The solid dispersions of the invention can include a solid dispersion comprising thienotriazolodiazepine compound of Formula (1) and a polymer and additives. In some embodiments, the solid dispersions can achieve absorption of the thienotriazolodiazepine compound of Formula (1) into the bloodstream that cannot be obtained by merely admixing the thienotriazolodiazepine compound of Formula (1) with additives since the thienotriazolodiazepine compound of Formula (1) drug has negligible solubility in water and most aqueous media. The bioavailability, of thienotriazolodiazepine compound of Formula (1) or of thienotriazolodiazepine compound (1-1) may be measured using a variety of in vitro and/or in vivo studies. The in vivo studies may be performed, for example, using rats, dogs or humans.

The bioavailability may be measured by the area under the curve (AUC) value obtained by plotting a serum or plasma concentration, of the thienotriazolodiazepine compound of Formula (1) or thienotriazolodiazepine compound (1-1), along the ordinate (Y-axis) against time along the abscissa (X-axis). The AUC value of the thienotriazolodiazepine compound of Formula (1) or thienotriazolodiazepine compound (1-1) from the solid dispersion, is then compared to the AUC value of an equivalent concentration of crystalline thienotriazolodiazepine compound of Formula (1) or crystalline thienotriazolodiazepine compound (1-1) without polymer. In some embodiments, the solid dispersion provides an area under the curve (AUC) value, when administered orally to a dog, that is selected from: at least 0.4 times, 0.5 times, 0.6 time, 0.8 time, 1.0 times, a corresponding AUC value provided by a control composition administered intravenously to a dog, wherein the control composition comprises an equivalent quantity of a crystalline thienotriazolodiazepine compound of Formula I.

The bioavailability may be measured by in vitro tests simulating the pH values of a gastric environment and an intestine environment. The measurements may be made by suspending a solid dispersion of the thienotriazolodiazepine compound of Formula (1) or thienotriazolodiazepine compound (1-1), in an aqueous in vitro test medium having a pH between 1.0 to 2.0, and the pH is then adjusted to a pH between 5.0 and 7.0, in a control in vitro test medium. The concentration of the amorphous thienotriazolodiazepine compound of Formula (1) or amorphous thienotriazolodiazepine compound (1-1) may be measured at any time during the first two hours following the pH adjustment. In some embodiments, the solid dispersion provides a concentration, of the amorphous thienotriazolodiazepine compound of Formula (1) or amorphous thienotriazolodiazepine compound (1-1), in an aqueous in vitro test medium at pH between 5.0 to 7.0 that is selected from: at least 5-fold greater, at least 6 fold greater, at least 7 fold greater, at least 8 fold greater, at least 9 fold greater or at least 10 fold greater, compared to a concentration of a crystalline thienotriazolodiazepine compound of Formula (1) or crystalline thienotriazolodiazepine compound (1-1), without polymer.

In other embodiments, the concentration of the amorphous thienotriazolodiazepine compound of Formula (1) or amorphous thienotriazolodiazepine compound (1-1), from the solid dispersion placed in an aqueous in vitro test medium having a pH of 1.0 to 2.0, is: at least 40%, at least 50% higher, at least 60%, at least 70%; at least 80%, than a concentration of a crystalline thienotriazolodiazepine compound of Formula (1) without polymer. In some such embodiments, the polymer of the solid dispersion is HPMCAS. In some such embodiments, the polymer of the solid dispersion is PVP.

In other embodiments, a concentration of the amorphous thienotriazolodiazepine compound of Formula (1) or amorphous thienotriazolodiazepine compound (1-1), from the solid dispersion, is: at least 40%, at least 50% higher, at least 60%, at least 70%; at least 80%, compared to a concentration of thienotriazolodiazepine compound of Formula (1), from a solid dispersion of thienotriazolodiazepine compound of the Formula (1) and a pharmaceutically acceptable polymer selected from the group consisting of: hypromellose phthalate and ethyl acrylate-methyl methacrylate-trimethylammonioethyl methacrylate chloride copolymer, wherein each solid dispersion was placed in an aqueous in vitro test medium having a pH of 1.0 to 2.0. In some such embodiments, the polymer of the solid dispersion is HPMCAS. In some such embodiments, the polymer of the solid dispersion is PVP.

In some embodiments, the solid dispersions, described herein, exhibit stability against recrystallization of the thienotriazolodiazepine compound of the Formula (1) or the thienotriazolodiazepine compound (1-1) when exposed to humidity and temperature over time. In one embodiment, the concentration of the amorphous thienotriazolodiazepine compound of the Formula (1) or the thienotriazolodiazepine compound (1-1) which remains amorphous is selected from: at least 90%, at least 91%, at least 92%, at least 93%, at least 94%, at least 95%, at least 96%, at least 97%, at least 98% and at least 99%.

III. DOSAGE FORMS

Suitable dosage forms that can be used with the solid dispersions of the present invention include, but are not limited to, capsules, tablets, mini-tablets, beads, beadlets, pellets, granules, granulates, and powder. Suitable dosage forms may be coated, for example using an enteric coating. Suitable coatings may comprise but are not limited to cellulose acetate phthalate, hydroxypropylmethylcellulose (HPMC), hydroxypropylmethylcellulose phthalate, a polymethylacrylic acid copolymer, or hydroxylpropylmethylcellulose acetate succinate (HPMCAS). In some embodiments, certain combinations can be encountered, for example, in the same sample some molecules of the thienotriazolodiazepine of the present invention may be present in clusters while some are molecularly dispersed with a carrier.

In some embodiments, the solid dispersions of the invention may be formulated as tablets, caplets, or capsules. In one some embodiments, the solid dispersions of the invention may be formulated as mini-tablets or pour-into-mouth granules, or oral powders for constitution. In some embodiments, the solid dispersions of the invention are dispersed in a suitable diluent in combination with other excipients (e.g., re-crystallization/precipitation inhibiting polymers, taste-masking components, etc) to give a ready-to-use suspension formulation. In some embodiments, the solid dispersions of the invention may be formulated for pediatric treatment.

In one embodiment, the pharmaceutical composition of the present invention is formulated for oral administration. In one embodiment, the pharmaceutical composition comprises a solid dispersion, according to the various embodiments described herein, comprising a thienotriazolodiazepine compound of Formula (1) or a pharmaceutically acceptable salt, a solvate, including a hydrate, a racemate, an enantiomer, an isomer, or an isotopically-labeled form thereof; and a polymer carrier. In one embodiment, the pharmaceutical composition further includes one or more additives such as disintegrants, lubricants, glidants, binders, and fillers.

Examples of suitable pharmaceutically acceptable lubricants and pharmaceutically acceptable glidants for use with the pharmaceutical composition include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose, glyceryl behenate, stearic acid, hydrogenated castor oil, glyceryl monostearate, and sodium stearyl fumarate.

Examples of suitable pharmaceutically acceptable binders for use with the pharmaceutical composition include, but are not limited to starches; celluloses and derivatives thereof, e.g., microcrystalline cellulose (e.g., AVICEL PH from FMC), hydroxypropyl cellulose, hydroxyethyl cellulose, and hydroxylpropylmethylcellulose (HPMC, e.g., METHOCEL from Dow Chemical); sucrose, dextrose, corn syrup; polysaccharides; and gelatin.

Examples of suitable pharmaceutically acceptable fillers and pharmaceutically acceptable diluents for use with the pharmaceutical composition include, but are not limited to, confectioner's sugar, compressible sugar, dextrates, dextrin, dextrose, lactose, mannitol, microcrystalline cellulose (MCC), powdered cellulose, sorbitol, sucrose, and talc.

In some embodiments, excipients may serve more than one function in the pharmaceutical composition. For example, fillers or binders may also be disintegrants, glidants, anti-adherents, lubricants, sweeteners and the like.

In some embodiments, the pharmaceutical compositions of the present invention may further include additives or ingredients, such as antioxidants (e.g., ascorbyl palmitate, butylated hydroxylanisole (BHA), butylated hydroxytoluene (BHT), α-tocopherols, propyl gallate, and fumaric acid), antimicrobial agents, enzyme inhibitors, stabilizers (e.g., malonic acid), and/or preserving agents.

Generally, the pharmaceutical compositions of the present invention may be formulated into any suitable solid dosage form. In some embodiments, the solid dispersions of the invention are compounded in unit dosage form, e.g., as a capsule, or tablet, or a multi-particulate system such as granules or granulates or a powder, for administration.

In one embodiment, a pharmaceutical compositions includes a solid dispersion of a thienotriazolodiazepine compound of Formula (1), according to the various embodiments of solid dispersions described herein, and hydroxypropylmethylcellulose acetate succinate (HPMCAS), wherein the thienotriazolodiazepine compound is amorphous in the solid dispersion and has a thienotriazolodiazepine compound to hydroxypropylmethylcellulose acetate succinate (HPMCAS), weight ratio of 1:3 to 1:1; 45-50 wt. % of lactose monohydrate; 35-40 wt. % of microcrystalline cellulose; 4-6 wt. % of croscarmellose sodium; 0.8-1.5 wt. % of colloidal silicon dioxide; and 0.8-1.5 wt. % of magnesium stearate.

IV. DOSAGE

In one embodiment, the present invention provides a pharmaceutical composition that maybe formulated into any suitable solid dosage form. In one embodiment, a pharmaceutical composition in accordance with the present invention comprises one or more of the various embodiments of the thienotriazolodiazepine of Formula (1) as described herein in a dosage amount ranging from about 10 mg to about 100 mg. In one embodiment, the pharmaceutical composition of the present invention includes one or more of the various embodiments of the thienotriazolodiazepine of Formula (1) as described herein in a dosage amount selected from the group consisting of from about 10 mg to about 100 mg, about 10 mg to about 90 mg, about 10 mg to about 80 mg, about 10 mg to about 70 mg, about 10 mg to about 60 mg, about 10 mg to about 50 mg, about 10 mg to about 40 mg, about 10 mg to about 30 mg, and about 10 mg to about 20 mg. In one embodiment, the pharmaceutical composition of the present invention includes one or more of the various embodiments of the thienotriazolodiazepine of Formula (1) as described herein in a dosage amount selected from the group consisting of about 10 mg, about 50 mg, about 75 mg, about 100 mg.

In some embodiments, the methods of the present invention includes administering to a subject in need thereof one or more of the various embodiments of the thienotriazolodiazepine of Formula (I) as described herein in a dosage amount selected from the group consisting of about 1 mg, about 2 mg, about 2.5 mg, about 3 mg, about 4 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, and about 150 mg, and in a dosage form selected from the group consisting of once weekly, once daily every sixth day, once daily every fifth day, once daily every fourth day, once daily every third day, once daily every other day, once daily, twice daily, three times daily, four times daily, and five times daily. In another embodiment, any of the foregoing dosage amounts or dosage forms is decreased periodically or increased periodically.

In some embodiments, the methods of the present invention includes administering to a subject in need thereof a thienotriazolodiazepine selected from the group consisting of compounds (1-1), (1-2), (1-3), (1-4), (1-5), (1-6), (1-7), (1-8), (1-9), (1-10), (1-11), (1- 12), (1-13), (1-14), (1-15), (1-16), (1-17), and (1-18), in a dosage amount selected from the group consisting of about 1 mg, about 2 mg, about 2.5 mg, about 3 mg, about 4 mg, about 5 mg, about 7.5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, and about 150 mg, and in a dosage form selected from the group consisting of once weekly, once daily every sixth day, once daily every fifth day, once daily every fourth day, once daily every third day, once daily every other day, once daily, twice daily, three times daily, four times daily, and five times daily. In another embodiment, any of the foregoing dosage amounts or dosage forms is decreased periodically or increased periodically.

Such unit dosage forms are suitable for administration 1 to 5 times daily depending on the particular purpose of therapy, the phase of therapy, and the like. In one embodiment, the dosage form may be administered to a subject in need thereof at least once daily for at least two successive days. In one embodiment, the dosage form may be administered to a subject in need thereof at least once daily on alternative days. In one embodiment, the dosage form may be administered to a subject in need thereof at least weekly and divided into equal and/or unequal doses. In one embodiment, the dosage form may be administered to a subject in need thereof weekly, given either on three alternate days and/or 6 times per week. In one embodiment, the dosage form may be administered to a subject in need thereof in divided doses on alternate days, every third day, every fourth day, every fifth day, every sixth day and/or weekly. In one embodiment, the dosage form may be administered to a subject in need thereof two or more equally or unequally divided doses per month.

The dosage form used, e.g., in a capsule, tablet, minitablet, beads, beadlets, pellets, granules, granulates, or powder may be coated, for example using an enteric coating. Suitable coatings may comprise but are not limited to cellulose acetate phthalate, hydroxypropylmethylcellulose (HPMC), hydroxypropylmethylcellulose phthalate, a polymethylacrylic acid copolymer, or hydroxylpropylmethylcellulose acetate succinate (HPMCAS).

V. PROCESS

The thienotriazolodiazepine compounds disclosed herein can exist as free base or as acid addition salt can be obtained according to the procedures described in US Patent Application Publication No. 2010/0286127, incorporated by reference in its entirety herein, or in the present application. Individual enantiomers and diastereomers of the thienotriazolodiazepine compounds of the present invention can be prepared synthetically from commercially available starting materials that contain asymmetric or stereogenic centers, or by preparation of racemic mixtures followed by resolution methods well known to those of ordinary skill in the art.

In some embodiments, a one or more of the various embodiments for the formulation of the thienotriazolodiazepine, according to Formula (1), is prepared by a solvent evaporation method. In one embodiment, the solvent evaporation method comprises solubilization of a thienotriazolodiazepine compound, according to Formula (1), carrier in a volatile solvent that is subsequently evaporated. In one embodiment, the volatile solvent may one or more excipients. In one embodiment, the one or more excipients include, but are not limited to anti-sticking agents, inert fillers, surfactants wetting agents, pH modifiers and additives. In one embodiment, the excipients may dissolved or in suspended or swollen state in the volatile solvent.

In one embodiment, preparation of solid dispersions in accordance with the present invention includes drying one or more excipients suspended in a volatile solvent. In one embodiment, the drying includes vacuum drying, slow evaporation of the volatile solvent at low temperature, use of a rotary evaporator, spray-drying, spray granulation, freeze-drying, or use of supercritical fluids.

In one embodiment, spray drying preparation of a formulation for the thienotriazolodiazepine composition, according to Formula (1), is used which involves atomization of a suspension or a solution of the composition into small droplets, followed by rapid removal solvent from the formulation. In one embodiment, preparation of a formulation in accordance with the present invention involves spray granulation in which a solution or a suspension of the composition in a solvent is sprayed onto a suitable chemically and/or physically inert filler, such as lactose or mannitol. In one embodiment, spray granulation of the solution or the suspension of the composition is achieved via two-way or three-way nozzles.

The invention is illustrated in the following non-limiting examples.

VI. EXAMPLES

The invention is illustrated in the following non-limiting examples.

Example 1: In Vitro Screening of Solid Dispersions of Compound (1-1)

Ten solid dispersions were prepared using compound (1-1) and one of five polymers, including hypromellose acetate succinate (HPMCAS-M), hypromellose phthalate (HPMCP-HP55), polyvinylpyrrolidone (PVP), PVP-vinyl acetate (PVP-VA), and Euragit L100-55, at both 25% and 50% of compound (1-1) loading, for each polymer. Solid dispersions were prepared by a solvent evaporation method, using spray-drying followed by secondary drying in a low-temperature convection oven. The performance of each solid dispersion was assessed via a non-sink dissolution performance test which measured both the total amount of drug and the amount of free drug present in solution over time. Non-sink dissolution was chosen because it best represents the in vivo situation for low soluble compounds. This test included a "gastric transfer" of dispersion from gastric pH (0.1N NaCl, pH 1.0) to intestinal pH (FaFSSIF, pH 6.5) approximately 30 to 40 minutes after the introduction of dispersion to the test medium, simulating in vivo conditions. [FaFSSIF is Fasted State Simulated Intestinal Fluid, comprised of 3 mM sodium taurocholate, 0.75 mM lechithin, 0.174 g NaOH pellets, 1.977 g $NaH_2PO_4.H_2O$, 3.093 g NaCl, and purified water qs 500 mL.] The amount of dissolved drug was quantified using a high-performance liquid chromatrography (HPLC) method and an Agilent 1100 series HPLC. The dissolution profiles of the formulations (FIGS. 1A-1J) showed large increases in drug solubility in all dispersion candidates relative to the unformulated compound in the same media. Of the solid dispersions, the 25% compound (1-1) in PVP, 25% compound (1-1) in HPMCAS-M, and 50% compound (1-1) in HPMCAS-M dispersions were the most promising candidates for enhanced oral absorption as compared to the unformulated compound, based on finding higher levels of free drug released at intestinal pH.

Example 2: In Vivo Screening of Solid Dispersions of Compound (1-1)

The three most promising solid dispersions of compound (1-1), namely the 25% compound (1-1) in PVP, 25% compound (1-1) in HPMCAS-MG, and 50% compound (1-1) in HPMCAS-M dispersions, were prepared at larger scale for in vivo studies. Each formulation was assessed in the in vitro dissolution test described in Example 1. To ensure that these dispersions were both amorphous and homogeneous, each dispersion was assessed by powder x-ray diffraction (PXRD) and modulated differential scanning calorimetry (mDSC). Additionally, to understand the effect of water on the glass transition temperature (Tg) for each dispersion, mDSC was performed on samples first equilibrated at a set relative humidity (i.e., 25%, 50%, and 75% RH) for at least 18 hours. [Water can act as a plasticizer for solid dispersions and the hygroscopicity of the system due to the active compound or polymer can affect the amount of water uptake by these systems.]

Figure 2A:
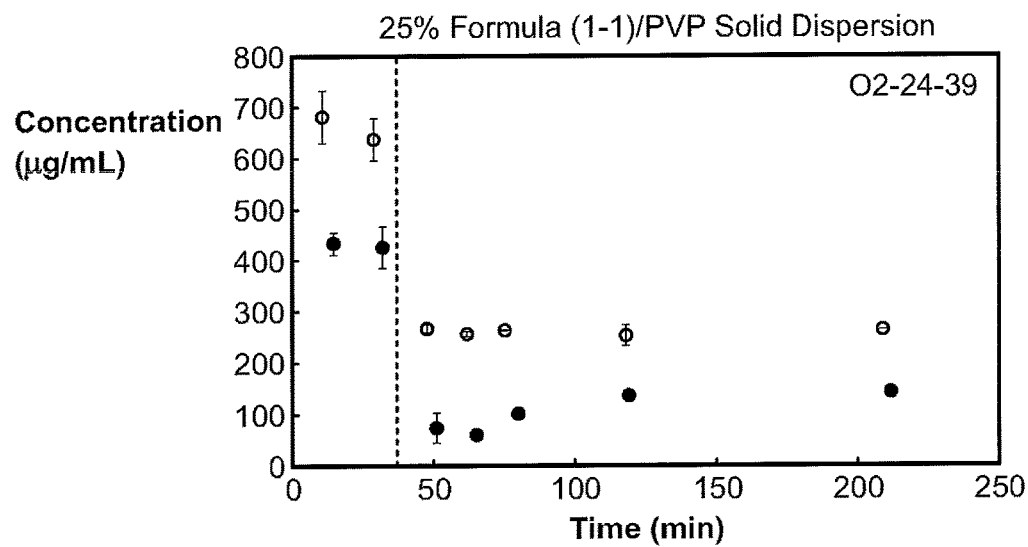
FIG. 2A illustrates results of in vivo screening of an exemplary formulation comprising a solid dispersion of 25% compound (1-1) and PVP.
Figure 2B:
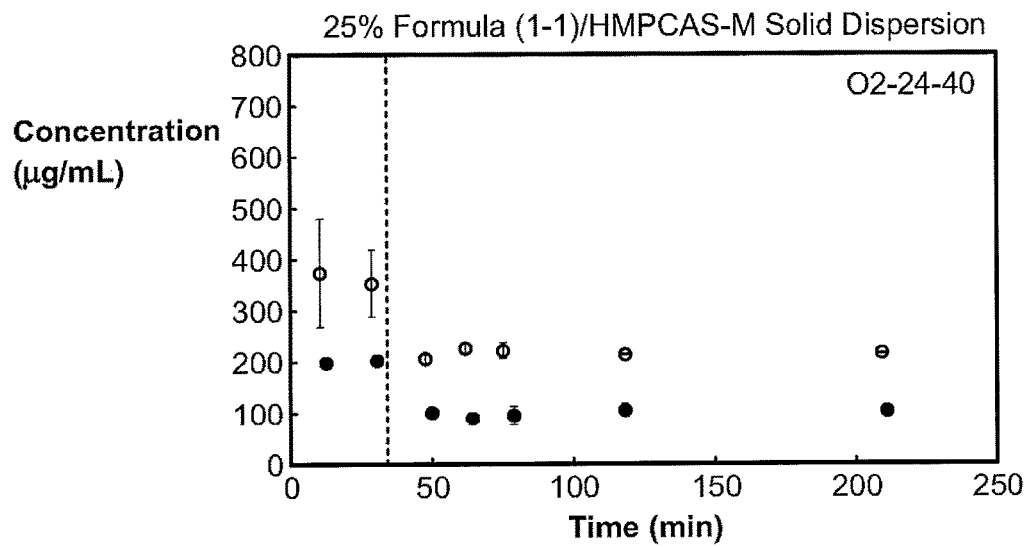
FIG. 2B illustrates results of an in vivo screening of an exemplary formulation comprising a solid dispersion of 25% compound (1-1) and HPMCAS-M.
Figure 2C:
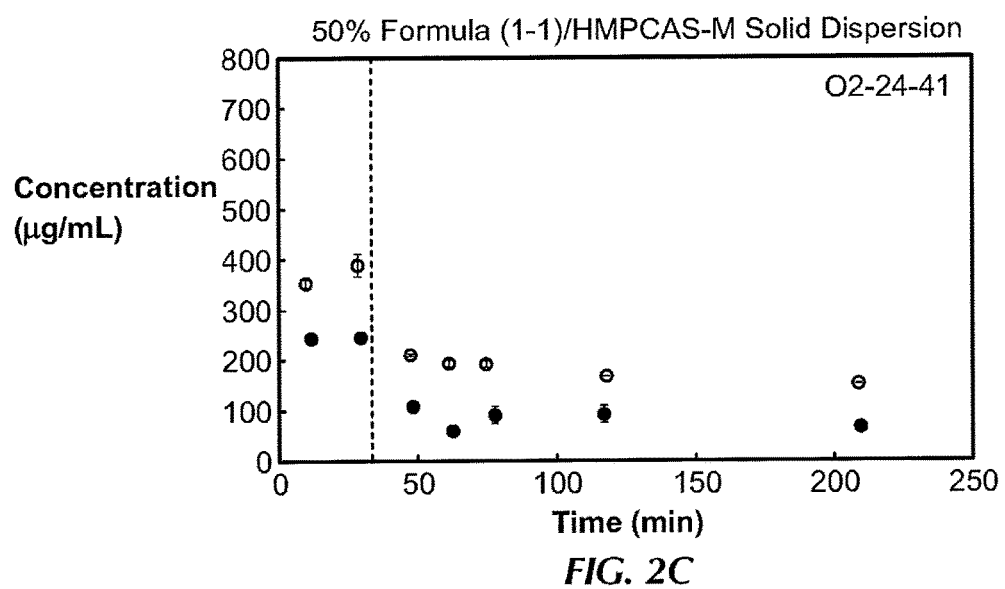
FIG. 2C illustrates results of an in vivo screening of an exemplary formulation comprising a solid dispersion of 50% compound (1-1) and HPMCAS-M.
Figure 3:
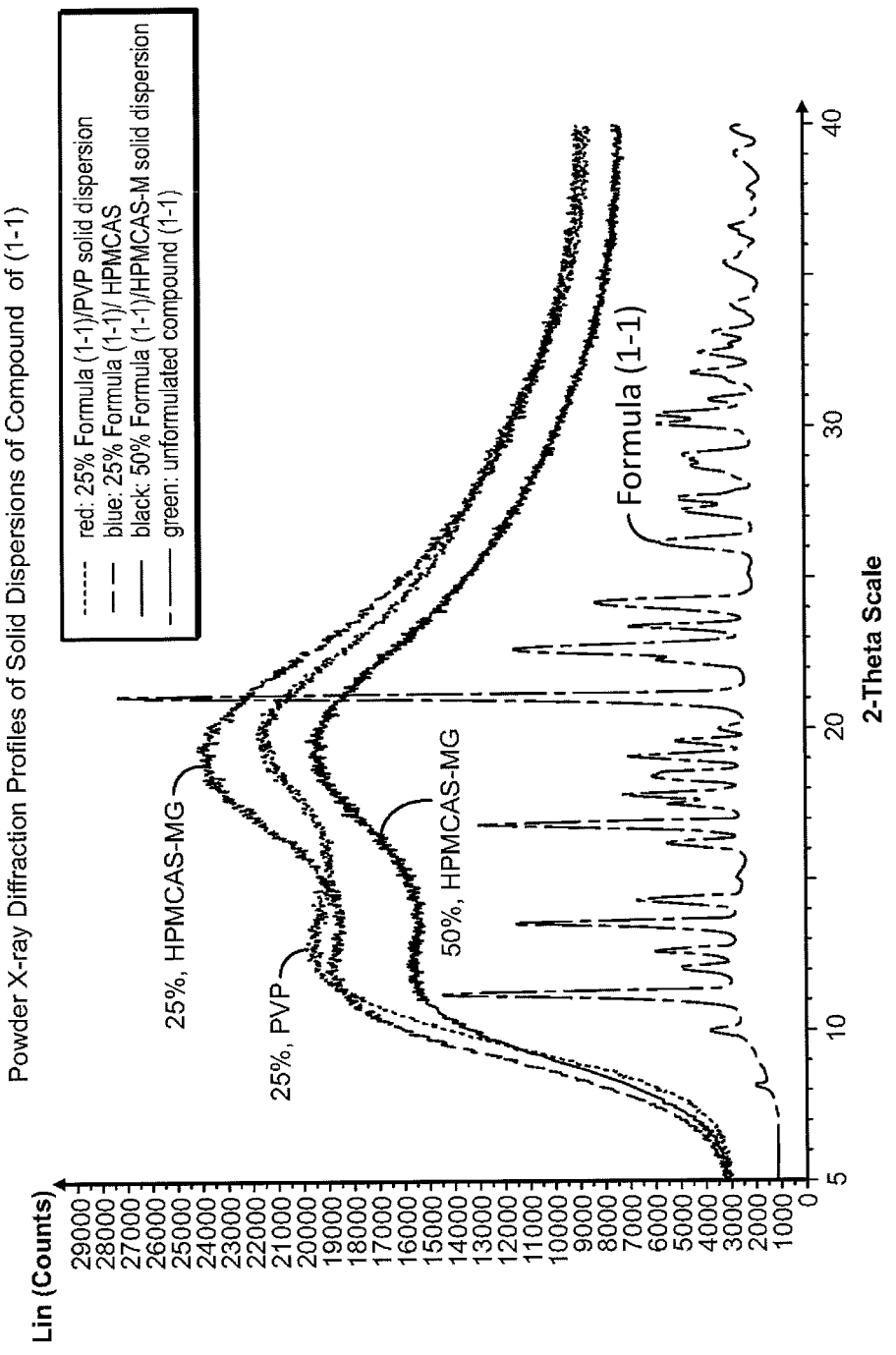
FIG. 3 illustrates powder X-ray diffraction profiles of solid dispersions of compound (1-1).
Figure 4A:
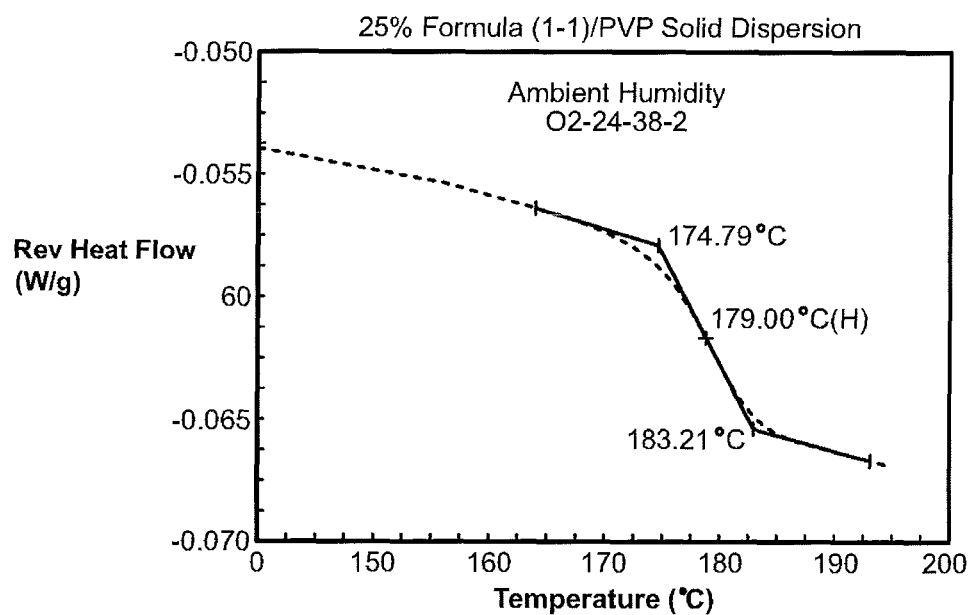
FIG. 4A illustrates modified differential scanning calorimetry trace for a solid dispersion of 25% compound (1-1) and PVP equilibrated under ambient conditions.
Figure 4B:
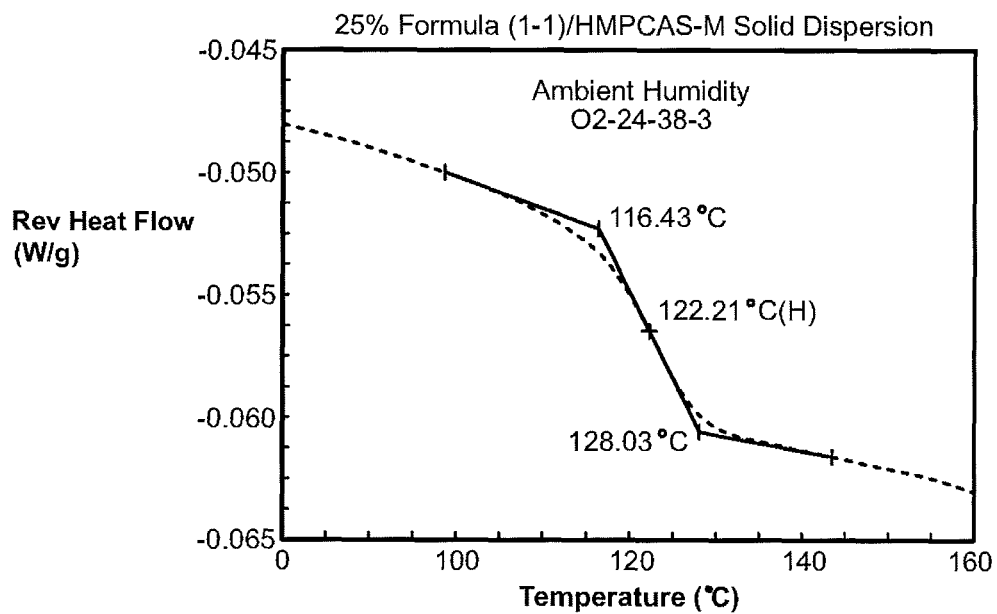
FIG. 4B illustrates modified differential scanning calorimetry trace for a solid dispersion of 25% compound (1-1) and HPMCAS-M equilibrated under ambient conditions.
Figure 4C:
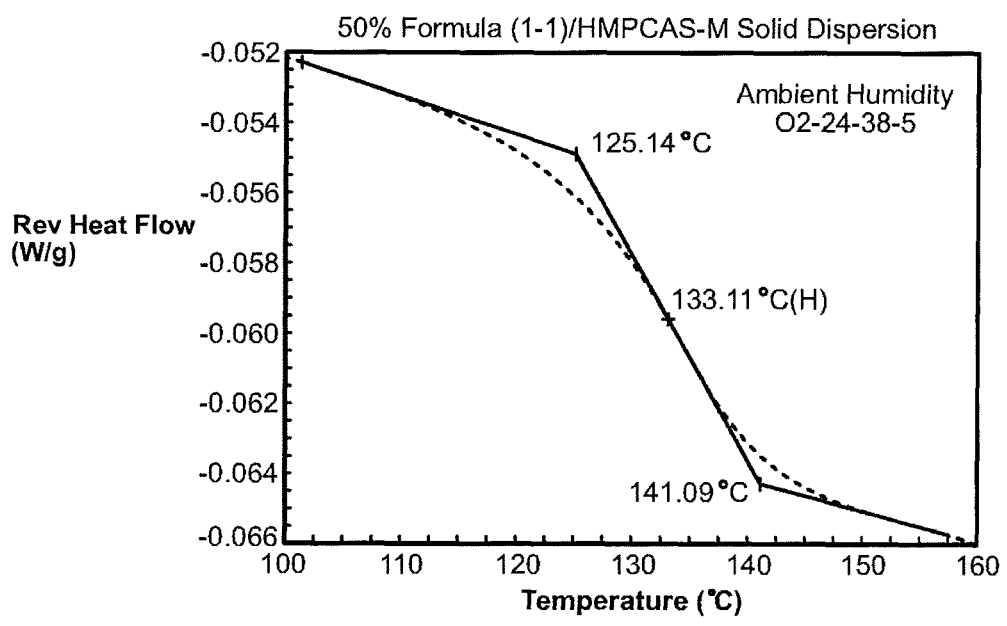
FIG. 4C illustrates modified differential scanning calorimetry trace for a solid dispersion of 50% compound (1-1) and HPMCAS-M equilibrated under ambient conditions.
Figure 5:
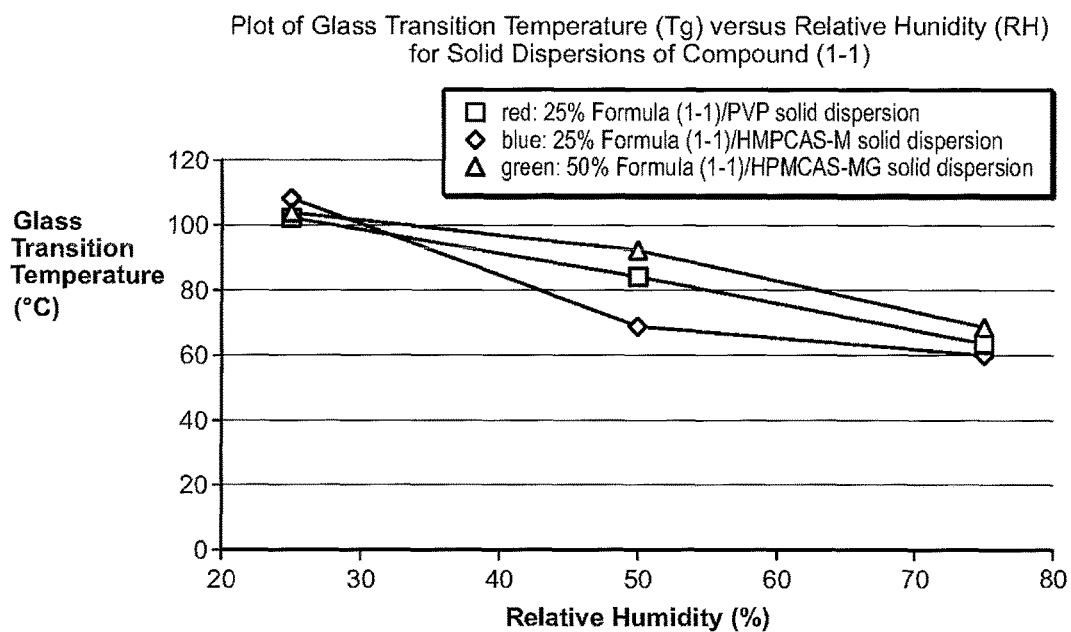
FIG. 5 illustrates plot of glass transition temperature (Tg) versus relative humidity (RH) for solid dispersions of 25% compound (1-1) and PVP or HMPCAS-M and 50% compound (1-1) and HPMCAS-MG.
Figure 6:
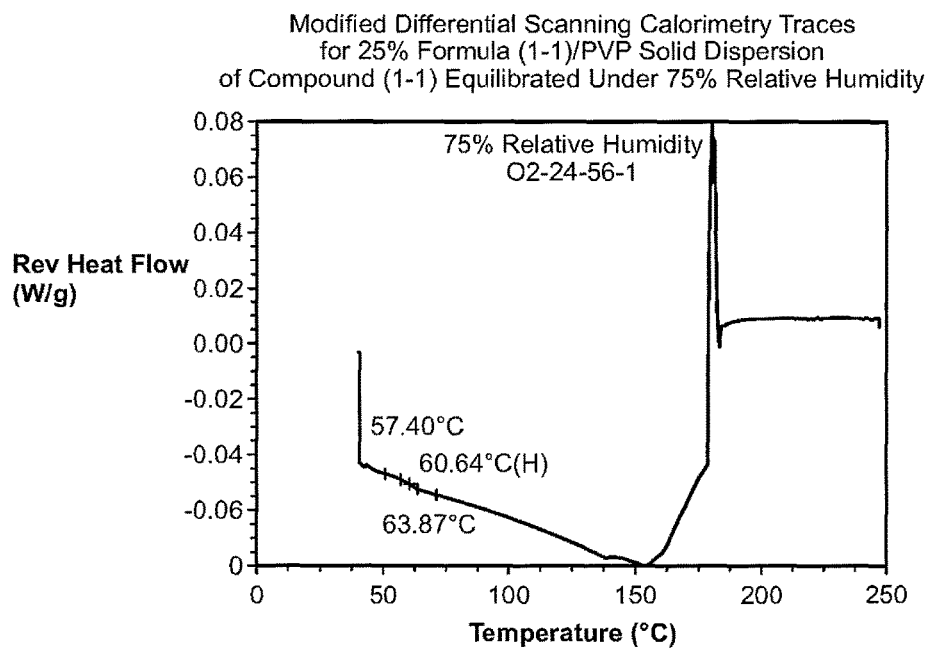
FIG. 6 illustrates modified differential scanning calorimetry trace for a solid dispersion of 25% compound (1-1) and PVP equilibrated under 75% relative humidity.

The non-sink dissolution results (FIGS. 2A-2C) were comparable to those found for the dispersions in Example 1. PXRD results (FIG. 3) showed no evidence of crystalline compound in any of the dispersions and mDSC results (FIGS. 4A-4C) showed a single glass transition temperature (Tg) for each dispersion, indicating that each dispersion was homogeneous. The x-ray diffractomer was a Bruker D-2 Phaser. An inverse relationship between Tg and relative humidity was observed for each (FIG. 5). Notably, for the 25% compound (1-1) in PVP solid dispersion equilibrated at 75% RH, there appeared to be two Tgs, indicating that phase separation was occurring, and this dispersion also showed a melt event at 75% RH, suggesting that crystallization occurred during the RH equilibration (FIG. 6). This finding suggests that the 25% compound (1-1) in PVP dispersion may be less stable than the HPMCAS-M dispersions.

To assess the bioavailability of the three dispersions, groups of male beagle dogs (three per group) were given a 3 mg/kg dose of an aqueous suspension of solid dispersion of compound (1-1) administered by oral gavage or a 1 mg/kg dose of compound (1-1) dissolved in water:ethanol:polyethylene glycol (PEG) 400 (60:20:20) and administered as an intravenous bolus into the cephalic vein. Blood samples were collected from the jugular vein of each animal at 0 (pre-dose), 5, 15, and 30 minutes and 1, 2, 4, 8, 12, and 24 hours following intravenous administration and at 0 (pre-dose), 15 and 30 minutes and 1, 2, 4, 8, 12, and 24 hours following oral gavage administration. The amount of compound (1-1) present in each sample was detected using a qualified LC-MS/MS method with a lower limit of quantification of 0.5 ng/mL. The area under the plasma concentration-time curve (AUC) was determined by use of the linear trapezoidal rule up to the last measurable concentration without extrapolation of the terminal elimination phase to infinity. The elimination half-life ($t_{1/2}$) was calculated by least-squares regression analysis of the terminal linear part of the log concentration-time curve. The maximum plasma concentration ($C_{max}$) and the time to $C_{max}$ ($t_{max}$) were derived directly from the plasma concentration data. The oral bioavailability (F) was calculated by dividing the dose normalized AUC after oral administration by the dose normalized AUC after intravenous administration and reported as percentages (%). Results, summarized in Table 1 below, gave mean oral bioavailabilities of the 25% compound (1-1) in PVP, 25% compound (1-1) in HPMCAS-M, and 50% compound (1-1) in HPMCAS-M solid dispersions of 58%, 49%, and 74%, respectively.

Crystalline compound (1-1) and the polymer hypromellose acetate succinate (HPMCAS-M) were dissolved in acetone and spray-dried to produce solid dispersion intermediate (SDI) granules containing a 50% compound (1-1) loading. The SDI was shown by PXRD analysis to be amorphous and by mDSC analysis to be homogeneous (i.e., single Tg under ambient conditions). The 50% compound (1-1) in HPMCAS-M solid dispersion (1000 g) and excipients, including microcrystalline cellulose filler-binder (4428 g), croscarmellose sodium disintegrant (636 g), colloidal silicon dioxide dispersant/lubricant 156 g), magnesium stearate dispersant/lubricant (156 g), and lactose monohydrate filler (5364 g) were blended in stages in a V-blender. The blend was them compacted and granulated to obtain a bulk density of approximately 0.6 g/mL. The blend was

TABLE 1 pharmacokinetic parameters of compound (1-1) after oral (po) and intravenous (iv) administrations to dogs (the values are averages from three dogs)

| Compound (1-1) formulation | Dose & Route | $C_{max}$ (ng/L) | $t_{max}$ (hr) | AUC (ng · min/mL) | $t_{1/2}$ (hr) | F (%) |
|---|---|---|---|---|---|---|
| Solution in water:ethanol:PEG400 (60:20:20) | 1 mg/kg IV | 769 | 0.083 | 53,312 | 1.5 | — |
| Aqueous suspension of 25% compound (1-1)/PVP solid dispersion | 3 mg/kg PO | 487 | 1.0 | 93,271 | 1.6 | 58 |
| Aqueous suspension of 25% compound (1-1)/HPMCAS-M solid dispersion | 3 mg/kg PO | 228 | 0.5 | 78,595 | 2.0 | 49 |
| Aqueous suspension of 50% compound (1-1)/HPMCAS-M solid dispersion | 3 mg/kg PO | 371 | 1.0 | 118,174 | 1.5 | 74 |

AUC: area under the plasma concentration-time curve;
$C_{max}$: maximum plasma concentration;
F: bioavailability;
HPMCAS: hypromellose acetate sodium;
IV: intravenous;
PEG: polyethylene glycon;
PO; per os, oral;
PVP: polyvinylpyrrolidone;
$t_{max}$: time of $C_{max}$;
$t_{1/2}$: plasma elimination half-life Example 3: Preparation and Clinical Use of Capsules Containing a Solid Dispersion of Compound (1-1)

A gelatin capsule of 10 mg strength was prepared for initial clinical studies in patients with hematologic malignancies. Based on results of in vitro and in vivo testing of solid dispersions of compound (1-1), as described in Examples 1 and 2, a 50% compound (1-1) in HPMCAS-M solid dispersion was selected for capsule development. Capsule development was initiated targeting a fill weight of 190 mg in a size 3 hard gelatin capsule, as this configuration would potentially allow increasing the capsule strength by filling a larger size capsule while maintaining the pharmaceutical composition. Based on experience, four capsule formulations were designed with different amounts of disintegrant and with and without wetting agent. Since all four formulations showed similar disintegration test and dissolution test results, the simplest formulation (without wetting agent and minimum disintegrant) was selected for manufacturing. Manufacturing process development and scale-up studies were performed to confirm the spray drying process and post-drying times for the solid dispersion; blending parameters; roller compaction and milling of the blend to achieve target bulk density of approximately 0.60 g/cc; and capsule filling conditions.

dispensed into size 3 hard gelatin capsules (target fill weight: 190 mg) using an automated filling machine and finished capsules were polished using a capsule polisher machine.

Pharmacokinetic assessments were performed following oral dosing of 10 mg capsules containing the 50% compound (1-1) in HPMCAS solid dispersion and results were compared with pharmacokinetic assessments performed following oral dosing of administration of 4×10 mg capsules containing the Eudragit solid dispersion of compound (1-1) to healthy volunteers A comparison of the two pharmaceutical compositions is provided in Tables 2A and 2B below. The Eudragit formulation previously was described in Example 5 in US Patent Application 2009/0012064 A1, published Jan. 8, 2009. That application noted that the Eudragit solid dispersion formulation was made by dissolving and/or dispersing the thienotriazolodiazepine of formula (A) and coating excipients, including ammonio methacrylate copolymer type B (Eudragit RS), methacrylic acid copolymer type C (Eudragit L100-55), talc, and magnesium aluminosilicate, in a mixture of water and ethanol. This heterogeneous mixture then was applied to microcrystalline cellulose spheres (Nonpareil 101, Freund) using a centrifugal fluidizing bed granulator to produce granules that were dispensed into size 2 hydroxypropyl methylcellulose capsules.

In both clinical studies, blood levels of compound (1-1) were determined using validated LC-MS/MS methods and pharmacokinetic analyses were performed based on plasma concentrations of compound (1-1) measured at various time points over 24 hours after capsule administration. Results, summarized in Table 3 below, showed that the HPMCAS-M solid dispersion formulation had over 3-fold higher bioavailability in humans than the Eudragit solid dispersion formulation based on AUCs (924*4/1140, adjusting for difference in doses administered). Additionally, based on the observed $T_{max}$, the HPMCAS formulation is more rapidly absorbed than the Eudragit formulation ($T_{max}$ of 1 h vs 4-6 h). The marked improvement in systemic exposure with the HPMCAS-M solid dispersion formulation is unexpected.

TABLE 2A solid dispersion capsules of compound (1-1) for clinical use
pharmaceutical composition containing 50% HPMCAS solid dispersion of compound (1-1): 10 mg strength, size 3 hard gelatin capsule

| Ingredient | Function | Capsule Content mg | Wt % |
|---|---|---|---|
| Compound of formula (II) | active agent | 10.0* | 5.56 |
| Hypromellose acetate succinate (HPMCAS-M) | carrier for solid dispersion | 10.0 | 5.56 |
| Lactose monohydrate | filler | 85.0 | 47.22 |
| Microcrystalline cellulose | filler-binder | 70.0 | 38.89 |
| Croscarmellose sodium | disintegrant | 10.0 | 5.56 |
| Collidal silicon dioxide | dispersant/lubricant | 2.5 | 1.39 |
| Magnesium stearate | dispersant/lubricant | | |
| Total | | 190.0 | 100.0 |

TABLE 2B pharmaceutical composition containing Eudragit L100-55 solid dispersion of compound (1-1): 10 mg strength, size 2 hard gelatin capsule

| Ingredient | Function | Capsule Content mg | Wt % |
|---|---|---|---|
| Compound (1-1) | active agent | 10.0* | 3.8 |
| Core: | | | |
| Microcrystalline cellulose spheres (Nonpareil 101, Freund, Inc) | vehicle | 100.0 | 38.5 |
| Compound/polymer layer: | | | |
| Ammonio methacrylate copolymer, type B (NF. PhEur) (Edragit RS, Evonik) | coating agent | 10.8 | 4.2 |
| Methacrylic acid copolymer, type C (NF)/Methacrylic acid-ethyl acrylate copolymer (1:1) type A (PhEur) (Eudragit L100-55, Evonik) | coating agent | 25.2 | 9.7 |
| Talc | coating agent | 88.2 | 33.9 |
| Magnesium aluminometasilicate (Neuslin, Fuji Chemical) | coating agent | 20.0 | 7.7 |
| Triethyl citrate | plasticizer | 5.0 | 1.9 |
| Silicon dioxide | fluidizing agent | 0.8 | 0.3 |
| | | 260.0 | 100.0 |

*as anhydrate

TABLE 3 pharmacokinetic parameters following oral administration of solid dispersions of compound (1-1) to humans

| Compound (1-1) formulation | # Patients | Dose and Route | $C_{max}$ (ng/mL) | $T_{max}$ (hr) | $AUC_{0-24\,h}$ (ng · h/mL) |
|---|---|---|---|---|---|
| Eudragit solid dispersion formulation | 7 | 40 mg PO | 83 | 4 to 6 | 1140 |
| 50% HMPCAS-M solid dispersion formulation | 7 | 10 mg PO | 286 | 1 | 925 |

$AUC_{0-24\,h}$: area under the OTX015 plasma concentration vs. time curve over 24 hours
$C_{max}$: maximum concentration in plasma
hr: hour
HPMCAS: hypromellose acetate succinate
mL: milliliter
ng: nanogram
PO: per os, oral
$T_{max}$: time of $C_{max}$ Example 4: Oral Exposure in the Rat The oral bioavailability of three formulations of solid dispersions of compound (1-1) was determined in rats. The three dispersions chosen were the 25% dispersion of compound (1-1) in PVP, the 25% dispersion of compound (1-1) in HPMCAS-MG, and the 50% dispersion of compound (1-1) in HPMCAS-MG. The animals used in the study were Specific Pathogen Free (SPF) Hsd:Sprague Dawley rats obtained from the Central Animal Laboratory at the University of Turku, Finland. The rats were originally purchased from Harlan, The Netherlands. The rats were female and were ten weeks of age, and 12 rats were used in the study. The animals were housed in polycarbonate Makrolon II cages (three animals per cage), the animal room temperature was 21+/−3° C., the animal room relative humidity was 55+/−15%, and the animal room lighting was artificial and was cycled for 12 hour light and dark periods (with the dark period between 18:00 and 06:00 hours). Aspen chips (Tapvei Oy, Estonia) were used for bedding, and bedding was changed at least once per week. Food and water was provided prior to dosing the animals but was removed during the first two hours after dosing.

The oral dosing solutions containing the 25% dispersion of compound (1-1) in PVP, the 25% dispersion of compound (1-1) in HPMCAS-MG, and the 50% dispersion of compound (1-1) in HPMCAS-MG were prepared by adding a pre-calculated amount of sterile water for injection to containers holding the dispersion using appropriate quantities to obtain a concentration of 0.75 mg/mL of compound (1-1). The oral dosing solutions were subjected to vortex mixing for 20 seconds prior to each dose. The dosing solution for intravenous administration contained 0.25 mg/mL of compound (1-1) and was prepared by dissolving 5 mg of compound (1-1) in a mixture containing 4 mL of polyethylene glycol with an average molecular weight of 400 Da (PEG400), 4 mL of ethanol (96% purity), and 12 mL of sterile water for injection. The dosing solution containing the 25% dispersion of compound (1-1) in PVP was used within 30 minutes after the addition of water. The dosing solutions containing the 25% dispersion of compound (1-1) in HPMCAS-MG and the 50% dispersion of compound (1-1) in HPMCAS-MG were used within 60 minutes of after the addition of water. A dosing volume of 4 mL/kg was used to give dose levels of compound (1-1) of 1 mg/kg for intravenous administration and 3 mg/kg for oral administration. The dosing scheme is given in Table 4.

TABLE 4

Dosing scheme for rat oral exposure study.

| Rat | Weight | Dose (mL) | Test Item | Route |
|---|---|---|---|---|
| 1 | 236.5 | 0.95 | Compound (1-1) | intravenous |
| 2 | 221 | 0.88 | Compound (1-1) | intravenous |
| 3 | 237.5 | 0.95 | Compound (1-1) | intravenous |
| 4 | 255.5 | 1.02 | 25% dispersion of compound (1-1) in PVP | oral |
| 5 | 224.2 | 0.90 | 25% dispersion of compound (1-1) in PVP | oral |
| 6 | 219.2 | 0.88 | 25% dispersion of compound (1-1) in PVP | oral |
| 7 | 251.6 | 1.01 | 25% dispersion of compound (1-1) in HPMCAS-MG | oral |
| 8 | 240.4 | 0.96 | 25% dispersion of compound (1-1) in HPMCAS-MG | oral |
| 9 | 238 | 0.95 | 25% dispersion of compound (1-1) in HPMCAS-MG | oral |
| 10 | 226.6 | 0.91 | 50% dispersion of compound (1-1) in HPMCAS-MG | oral |
| 11 | 228.4 | 0.91 | 50% dispersion of compound (1-1) in HPMCAS-MG | oral |
| 12 | 228.5 | 0.91 | 50% dispersion of compound (1-1) in HPMCAS-MG | oral |

Blood samples of approximately 50 µL were collected into Eppendorf tubes containing 5 µL of ethylenediaminetetraacetic acid (EDTA) solution at time points of 0.25, 0.5, 1, 2, 4, 8, 12, and 24 hours after dosing, with each sample collected within a window of 5 minutes from the prescribed time point. From each sample, 20 µL of plasma was obtained and stored at dry ice temperatures for analysis. Analysis of each sample for the concentration of compound (1-1) was performed using a validated liquid chromatography tandem mass spectrometry (LC-MS/MS) method with a lower limit of quantitation of 0.5 ng/mL.

Pharmacokinetic parameters were calculated with the Phoenix WinNonlin software package (version 6.2.1, Pharsight Corp., CA, USA) with standard noncompartmental methods. The elimination phase half-life ($t_{1/2}$) was calculated by least-squares regression analysis of the terminal linear part of the log concentration-time curve. The area under the plasma concentration-time curve (AUC) was determined by use of the linear trapezoidal rule up to the last measurable concentration and thereafter by extrapolation of the terminal elimination phase to infinity. The mean residence time (MRT), representing the average amount of time a compound remains in a compartment or system, was calculated by extrapolating the drug concentration profile to infinity. The maximum plasma concentration ($C_{max}$) and the time to $C_{max}$ ($t_{max}$) were derived directly from the plasma concentration data. The tentative oral bioavailability (F) was calculated by dividing the dose normalised AUC after oral administration by the dose normalised AUC after intravenous administration, i.e. F=(AUC(oral)/Dose(oral))/(AUC(intravenous)/Dose(intravenous))] and is reported as percentage (%).

Figure 7:
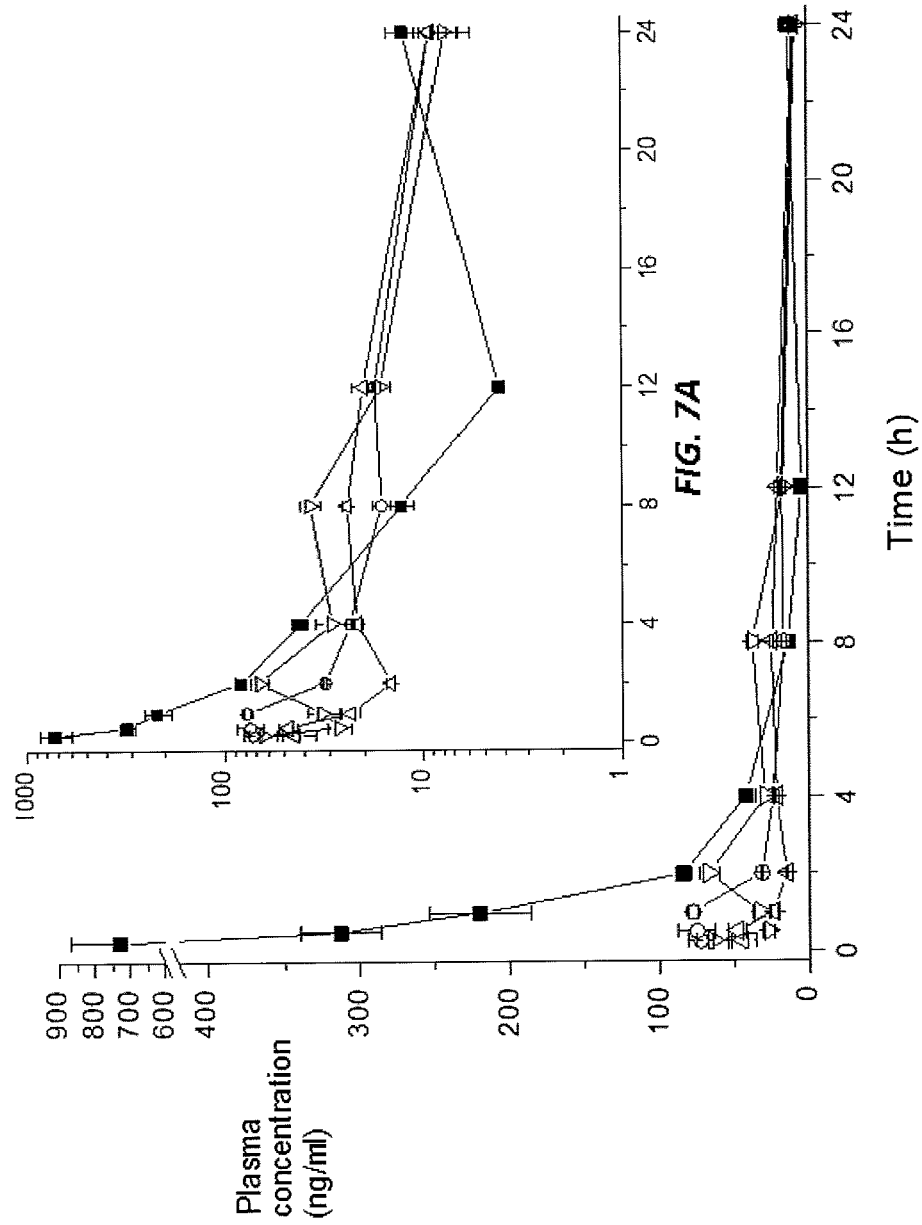
FIGS. 7A and 7B illustrate plasma concentration versus time curves for Compound (1-1) after 1 mg/kg intravenous dosing (solid rectangles) and 3 mg/kg oral dosing as 25% Compound (1-1):PVP (open circles), 25% Compound (1-1): HPMCAS-MG (open triangles), and 50% Compound (1-1): HPMCAS-MG (open inverted triangles). The inset depicts the same data plotted on a semilogarithmic scale.
Figure 8:
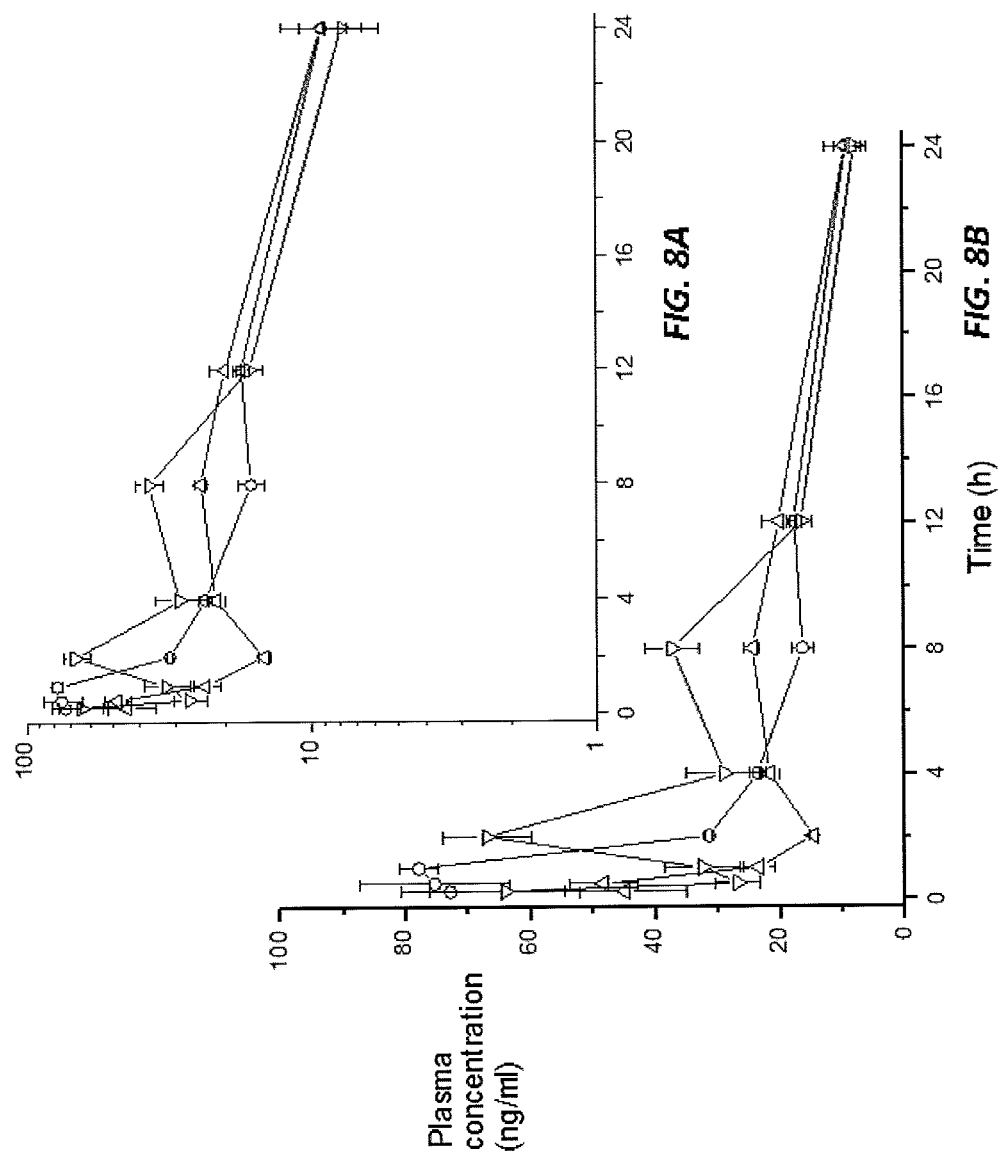
FIGS. 8A and 8B illustrate plasma concentration versus time curves for Compound (1-1) after 3 mg/kg oral dosing as 25% Compound (1-1):PVP (open circles), 25% Compound (1-1):HPMCAS-MG (open triangles), and 50% Compound (1-1):HPMCAS-MG (open inverted triangles). The inset depicts the same data plotted on a semi-logarithmic scale.

The pharmacokinetic parameters are given in Table 5, and the plasma concentration versus time plots are shown in FIGS. 7 and 8.

TABLE 5

Pharmacokinetic parameters of compound (1-1) after oral and intravenous administrations. The values are an average from three animals.

| Compound | Parameter | 1 mg/kg intravenous | 3 mg/kg oral | F (%) |
|---|---|---|---|---|
| Compound (1-1) water:ethanol:PEG 400 (60:20:20) | AUC (min*ng/ml) | 74698 | | |
| | $C_{max}$ (ng/ml) | 730 | | |
| | $T_{max}$ (hr) | 0.25 | | |
| | $t_{1/2}$ (hr) 8.5 | 8.5 | | |
| | Cl/F (ml/min/kg) | 13.4 | | |
| | MRT (hr) | 7.4 | | |
| 25% dispersion of compound (1-1) in PVP | AUC (min*ng/ml) | | 39920 | 18 |
| | $C_{max}$ (ng/ml) | | 77.9 | |
| | $T_{max}$ (hr) | | 1 | |
| | $t_{1/2}$ (hr) 8.5 | | 13.8 | |
| | Cl/F (ml/min/kg) | | 75.2 | |
| | MRT (hr) | | 18.0 | |
| 25% dispersion of compound (1-1) in HPMCAS-MG | AUC (min*ng/ml) | | 35306 | 16 |
| | $C_{max}$ (ng/ml) | | 48.3 | |
| | $T_{max}$ (hr) | | 0.5 | |
| | $t_{1/2}$ (hr) 8.5 | | 11.0 | |
| | Cl/F (ml/min/kg) | | 85.0 | |
| | MRT (hr) | | 17.1 | |
| 50% dispersion of compound (1-1) in HPMCAS-MG | AUC (min*ng/ml) | | 40238 | 18 |
| | $C_{max}$ (ng/ml) | | 67.0 | |
| | $T_{max}$ (hr) | | 2 | |
| | $t_{1/2}$ (hr) 8.5 | | 9.5 | |
| | Cl/F (ml/min/kg) | | 74.6 | |
| | MRT (hr) | | 12.8 | |

Example 5: Preparation of Spray Dried Dispersions

Spray dried dispersions of compound (1-1) were prepared using five selected polymers: HPMCAS-MG (Shin Etsu Chemical Co., Ltd.), HPMCP-HP55 (Shin Etsu Chemical Co., Ltd.), PVP (ISP, a division of Ashland, Inc.), PVP-VA (BASF Corp.), and Eudragit L100-55 (Evonik Industries AG). All spray dried solutions were prepared at 25% and 50% by weight with each polymer. All solutions were prepared in acetone, with the exception of the PVP solutions, which were prepared in ethanol. For each solution, 1.0 g of solids (polymer and compound (1-1)) were prepared in 10 g of solvent. The solutions were spray dried using a Büchi B-290, PE-024 spray dryer with a 1.5 mm nozzle and a Büchi B-295, P-002 condenser. The spray dryer nozzle pressure was set to 80 psi, the target outlet temperature was set to 40° C., the chiller temperature was set to −20° C., the pump speed was set to 100%, and the aspirator setting was 100%. After spray drying, the solid dispersions were collected and dried overnight in a low temperature convection oven to remove residual solvents.

Example 6: Stability with Humidity and Temperature

TABLE 6

| Test | Procedure | Acceptance Criteria | T = O (Initial) | T-1 month (storage at 40° C./75% RH) |
|---|---|---|---|---|
| Appearance | AM-0002 | White to off-white powder | Test Date/Ref: 6 Aug. 2012/02-41-2 | Test Date/Ref: 24 Sep. 2012/02-41-59 |
| | | | White Powder | White Powder |
| Potency (HPLC) | AM-0028 | 45.0-55.0 wt % | Test Date/Ref: 25 Jul. 2012/02-37-21 | Test Date/Ref: 25 Sep. 2012/02-4HI0 |
| | | | 50.0 | 49.4 |

TABLE 6-continued

Figure 9:
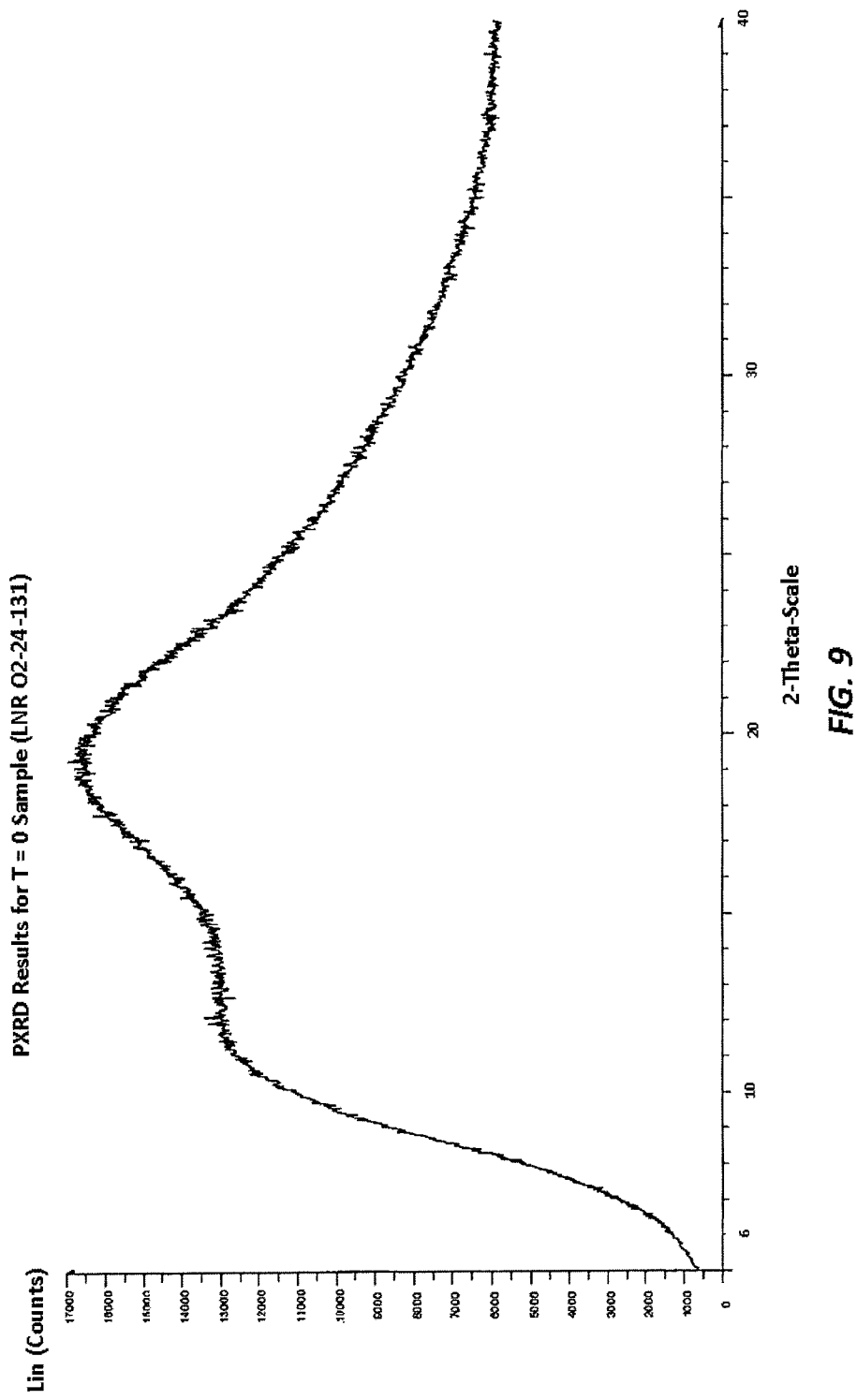
FIG. 9 illustrates a powder X-ray diffraction profile of solid dispersions of compound (1-1) in HPMCAS-MG at time zero of a stability test.
Figure 10:
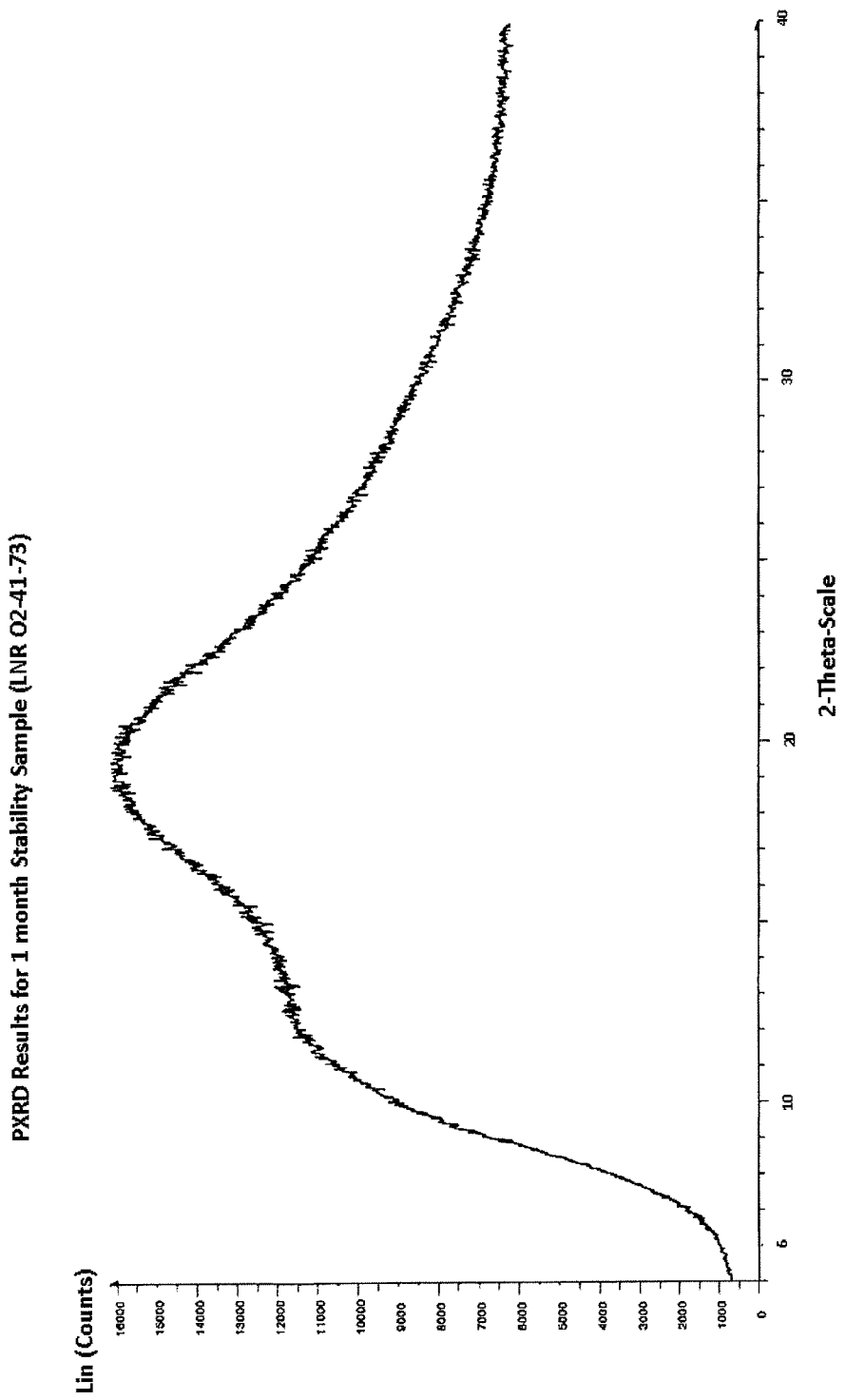
FIG. 10 illustrates a powder X-ray diffraction profile of solid dispersions of compound (1-1) in HPMCAS-MG after 1 month at 40° C. and 75% relative humidity.

| | | | Test Date/Ref: 25 Jul. 2012/02-34-49 | Test Date/Ref: 26 Sep. 2012/02-41-64 |
|---|---|---|---|---|
| Individual Related Substances (HPLC) | AM-0029 | Report results | RRT    % Area<br>No reportable related substances | RRT    % Area<br>No reportable related substances |
| Total Related Substances (HPLC) | AM · 0029 | Report results | Test Date/Ref: 25 Jul. 2012/02-34-49<br>No reportable related substances | Test Date/Ref: 26 Sep. 2012/02-41-64<br>No reportable related substances |
| Water Content (KF) | AM-0030 USP <921> | Report results (wt %) | Test Date/Ref: 2 Aug. 2012/02-41-1<br>1.52 | Test Date/Ref: 27 Sep. 2012/02-37-99<br>2.53 |
| X-Ray Powder Diffraction (XRPD) | USP <941> | Consistent with an amorphous form | Test Date/Ref: 24 Jul. 2012/02-24-131<br>Consistent with an amorphous form<br>See FIG. 9 | Test Date/Ref: 1 Oct. 2012/02-41-73<br>Consistent with an amorphous form<br>See FIG. 10 |
| Modulated Differential Scanning Calorimetry (mDSC) | USP <891> (n = 2 replicates) | Report individual and average glass transition temperatures ($T_g$, ° C.) | Test Date/Ref: 24 Jul. 2012/02-24-130<br>Replicate 1 = 134.30° C., Replicate 2 = 134.23° C., Replicate 3 = 135.28° C., Average =134.60° C. | Test Date/Ref: 26 Sep. 2012/02-37-98<br>Replicate 1 = 134.65° C., Replicate 2 = 134.43° C., Average = 134.54° C. |

Figure 11:
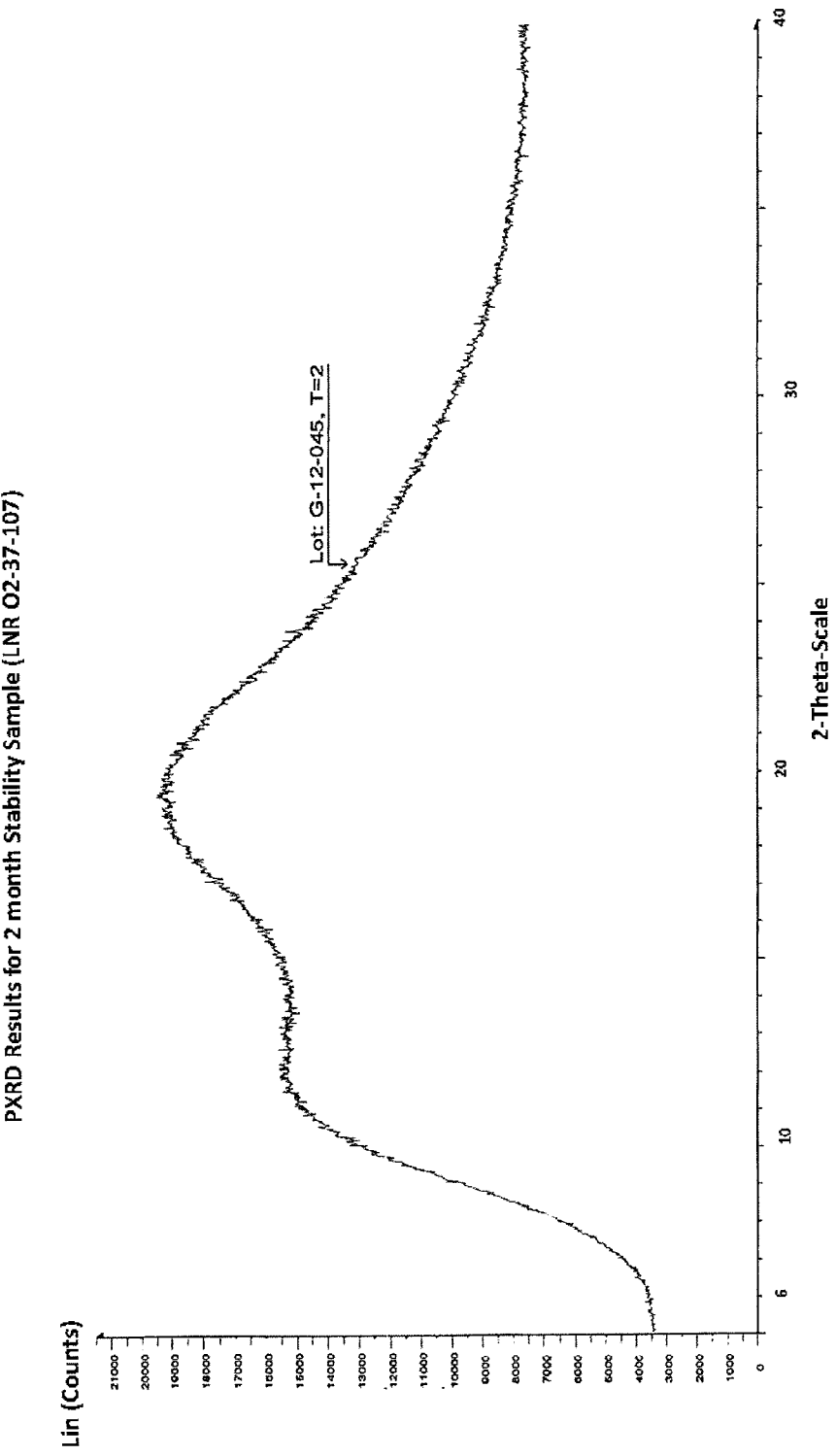
FIG. 11 illustrates a powder X-ray diffraction profile of solid dispersions of compound (1-1) in HPMCAS-MG after 2 months at 40° C. and 75% relative humidity.
Figure 12:
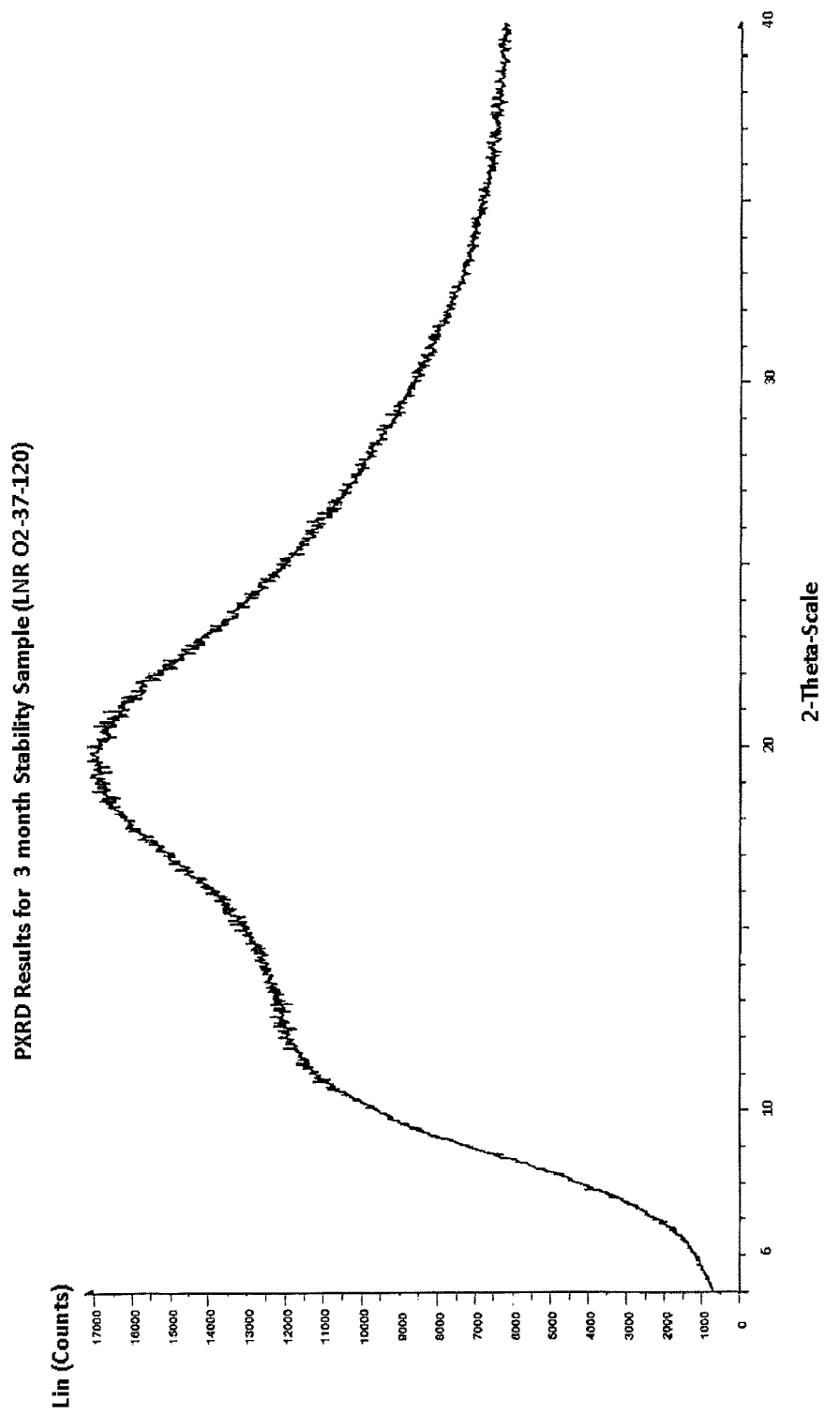
FIG. 12 illustrates a powder X-ray diffraction profile of solid dispersions of compound (1-1) in HPMCAS-MG after 3 month at 40° C. and 75% relative humidity.
Figure 13A:
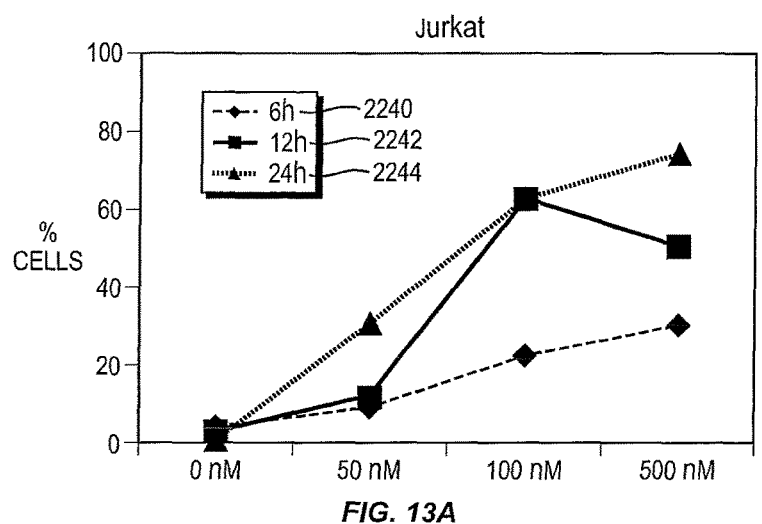
FIGS. 13A-13C illustrate kinetics of apoptosis induced by compound (1-1) in ALL cell lines: Jurkat, RS 4-11 and TOM-1 cells, which were harvested at different time points after treatment. Apoptotic cells were defined as annexin V+ with or without PI uptake. X-axis indicates doses of compound (1-1) and Y-axis indicates percentage of apoptotic cells. One representative experiment of three is shown.
Figure 13B:
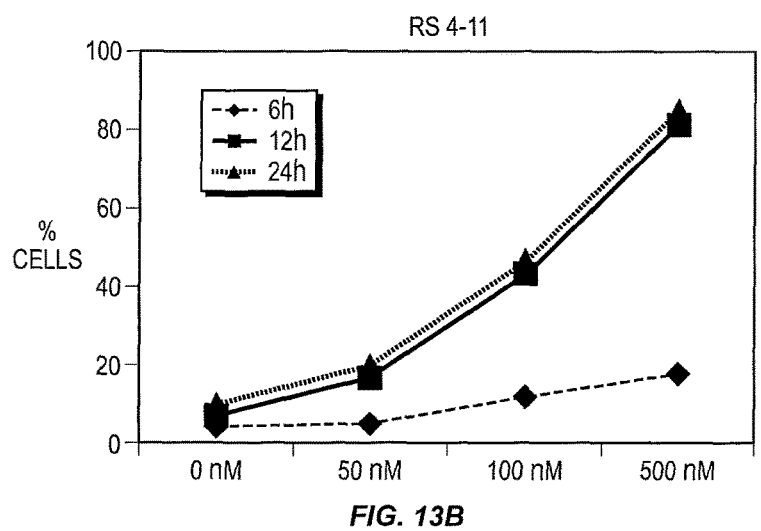
Figure 13C:
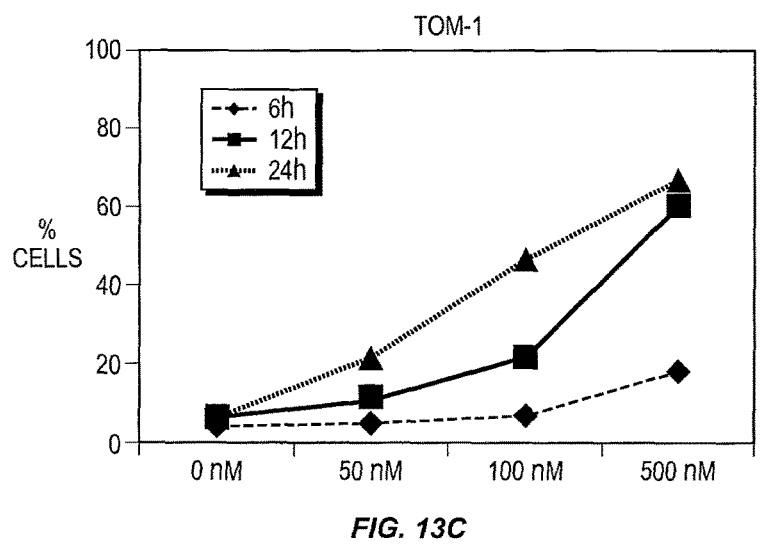

| Test | Procedure | T-2 month (storage at 40° C./75% RH) | T = 3 month (storage at 40° C./75% RH) |
|---|---|---|---|
| Appearance | AM-0002 | Test Date/Ref: 24 Oct. 2012/02-37-106<br>White Powder | Test Date/Ref: 17 Dec. 2012/02-37-119<br>White Powder |
| Potency (HPLC) | AM-0028 | Test Date/Ref: 24 Oct. 2012/02-37-105<br>49.8 | Test Date/Ref: 29 Nov. 2012/02-34-107<br>49.2 |
| Individual Related Substances (HPLC) | AM-0029 | Test Date/Ref: 24 Oct. 2012/02-37-105<br>RRT    % Area<br>0.68    0.06<br>0.77    0.06 | Test Date/Ref: 29 Nov. 2012/02-34-107<br>RRT    % Area<br>0.68    0.07<br>0.77    0.09 |
| Total Related Substances (HPLC) | AM · 0029 | Test Date/Ref: 24 Oct. 2012/02-37-105<br>0.12% | Test Date/Ref: 29 Nov. 2012/02-34-107<br>0.16% |
| Water Content (KF) | AM-0030 USP <921> | Test Date/Ref: 25 Oct. 2012102-37-110<br>2.70 | Test Date/Ref: 29 Nov. 2012/02-37-116<br>3.43 |
| X-Ray Powder Diffraction (XRPD) | USP <941> | Test Date/Ref: 24 Oct. 2012/02-37-107<br>Consistent with an amorphous form<br>See FIG. 11 | Test Date/Ref: 17 Dec. 2012/02-37-120<br>Consistent with an amorphous form<br>See FIG. 12 |
| Modulated Differential Scanning Calorimetry (mDSC) | USP <891> (n = 2 replicates) | Test Date/Ref: 24 Oct. 2012/02-37-108<br>Replicate 1 = 135.35° C., Replicate 2 = 134.93° C., Average = 135.14° C. | Test Date/Ref: 17 Dec. 2012/02-37-121<br>Replicate 1 = 134.36° C. Replicate 2 = 137.16° C. Average = 135.76° C. |

Spray dried dispersions of compound (1-1) in HPMCAS-MG were assessed for stability by exposure to moisture at elevated temperature. The glass transition temperature (Tg) as a function of relative humidity was determined at 75% relative humidity, 40° C. for 1, 2 and 3 months. The spray dried dispersion was stored in an LDPE bag inside a HDPE bottle to simulate bulk product packaging. The data is summarized in Table 6. At time zero, the Tg was 134° C., at 1 month the Tg was 134° C., at 2 months the Tg was 135° C. and at 3 months the Tg was 134° C. and only a single inflection point was observed for each measurement. X-ray diffraction patterns were also obtained for each sample. FIG. 9 illustrates a powder X-ray diffraction profile of solid dispersions of compound (1-1) in HPMCAS-MG at time zero of a stability test. FIGS. 10, 11 and 12 illustrate powder X-ray diffraction profiles of solid dispersions of compound (1-1) in HPMCAS-MG after 1 month, 2 months and 3 months, respectively, after exposure at 40° C. and 75% relative humidity.

The patterns did not show any diffraction lines associated with compound (1-1).

Example 7: Cell Lines and Selection of Primary Cells

Different representative cell lines for ALL including Jurkat cells (T-ALL), RS 4-11 (MLL-AF4 B-precursor ALL), TO'M-1, BV173 (both Ph+ ALL) and AML including K562 (Ph+CML in blast crisis), HL-60 (NRAS driven AML2), NOMO1 (MLL-AF9 driven AML), KG1 (BMP-FGRF+ AML6) and its more immature subtype KG1a were cultured in RPMI 1640 (Gibco Invitrogen, Basel, Switzerland) supplemented with 10% or 20% heat-inactivated fetal calf serum respectively, 2 mM L-glutamine, 100 IU/mL penicillin, and 100 g/mL streptomycin.

Mononuclear cells (MNC) from the bone marrow (BM) were isolated by Ficoll-Paque PLUS density gradient (Amersham Biosciences, Sunnyvale, USA). Patient cells were maintained in IMDM (Gibco) supplemented with 10% heat-inactivated fetal calf serum, 2 mM L-glutamine, 100 IU/mL penicillin, and 100 g/mL streptomycin without growth factors.

Example 8: MTT-Assay, Apoptosis Assessment and Cell Cycle Analysis

MTT-assay: cells were seeded first into 24-well plates at the density of 106 per well to avoid variations of concentrations in smaller volumes and treated with different doses of OTX015 prepared freshly from 1 mM stock solution in DMSO. Cells were transferred to 96-well plates for MTT-assay. Untreated cells and cells treated with equal amounts of DMSO (0.2-1%) used for dilution of OTX015 were used as controls. The 3-(4,5-dimethylthiazol-2-yl)-2,5-diphenyltetrazolium bromide (MTT) (Molecular Probes, Eugene, USA) was prepared as a stock of 5 mg/ml in PBS. 0.5 mg/mL of MTT solution was then added per well and incubated in the dark at 37° C. for 4 h. Cells were then lysed with 25% SDS lysis buffer and absorbance was read at 570 nm. Two independent experiments were run for each cell line. GI50 values were calculated with Prism v5 software (GraphPad Inc., La Jolla, USA).

Apoptosis Assessment:

a total of $1\times10^6$ cells derived from patients or cell lines were resuspended in 1 mL culture medium and incubated with the indicated dosages of OTX015 prepared freshly from 1 mM stock solution in DMSO. Control cells were incubated with the corresponding amount of dimethyl sulfoxide (DMSO 0.2-1%) to exclude toxicity of the excipient. Apoptotic cells were detected by cytofluorometric analysis using a FACScan (Becton Dickinson, Mountain View, USA). Cells were stained with propidium iodide (PI; 5 µg/mL; Becton Dickinson) and concomitantly for 15 minutes at RT with annexin-V-FITC (Becton Dickinson) according to the manufacturer's instructions to determine outer membrane phosphatidyl serine exposure. Data were analyzed with the Flowjo (Tree Star Inc., Ashland, USA) flow cytometry software.

Cell Cycle Analysis:

For conventional cell-cycle analysis, $1\times10^6$ cells were harvested, washed in PBS, and fixed in 70% ice cold ethanol. Cells were incubated with 100 µg/mL RNAse (Sigma, Saint-Quentin Fallavier, France) and stained with PI (25 µg/mL, Becton Dickinson) followed by an incubation period of 30 minutes at 37° C. Subsequently, cell-cycle distribution was determined by cytofluorometric analysis. Data were analyzed with the Flowjo (Tree Star Inc., Ashland, USA) flow cytometry software.

Compound (1-1) induced apoptosis in three ALL cell lines (Jurkat, RS 4-11, TOM-1) and four AML cell lines (HL60, K562, KG1 and KG1a) that were treated with different doses of the drug as detected by outer membrane phosphatidylserine exposure and propidium iodide incorporation at different time points (FIGS. 13A-13C and FIGS. 14A-14D). Compound (1-1) induced apoptosis in all cell lines tested but to a lesser extent in K562 and KG1a cells (FIG. 14B, D). In all other cell lines, 50% of cells became apoptotic within 12 to 24 hours after treatment with 100 nM of Compound (1-1).

Figure 15B:
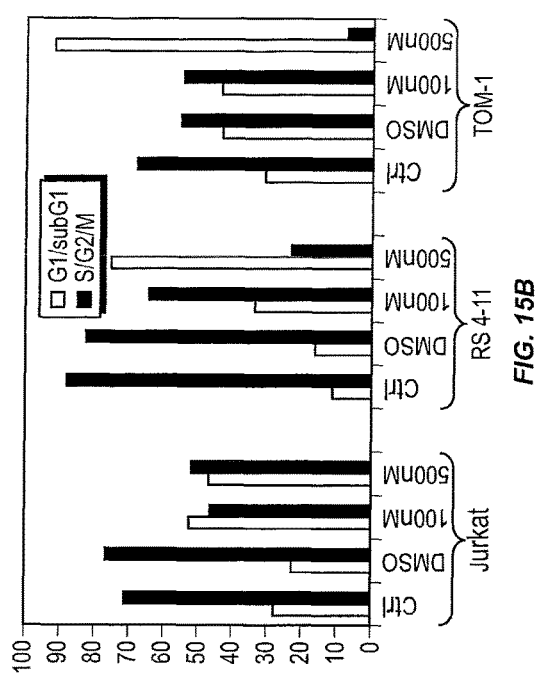
FIGS. 15A-15C illustrate cell cycle alterations induced by Compound (1-1) in ALL and AML cell lines. Representative histograms of flow cytometry profiles of untreated HL60 and cells treated for 24 h with 100 nM of Compound (1-1) (A). Cells were incubated with PI prior to cell cycle analysis. Cell cycle alterations for ALL (FIG. 15B) and AML (FIG. 15C) cell lines. X-axis indicates cell lines and Y-axis indicates percentage of cells in cell cycle phase.
Figure 15C:
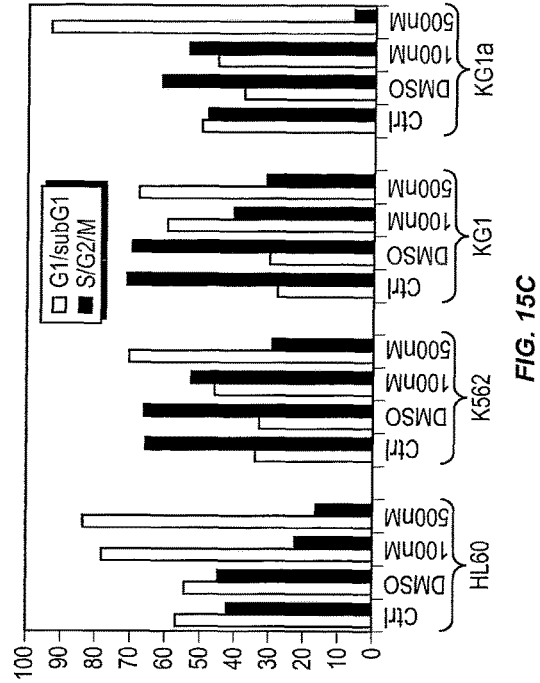
Figure 15A:
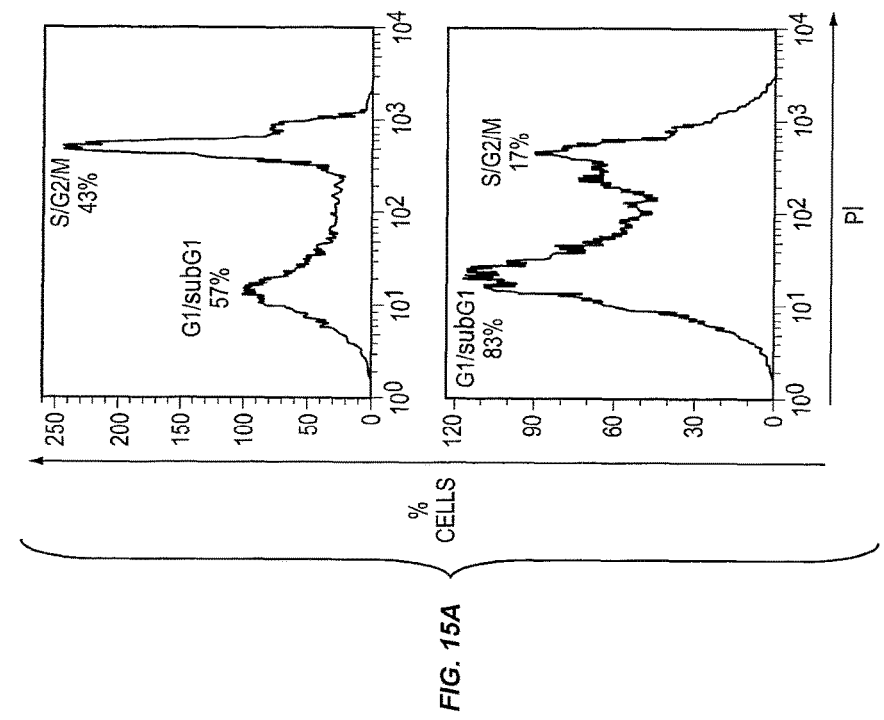
Figure 16:
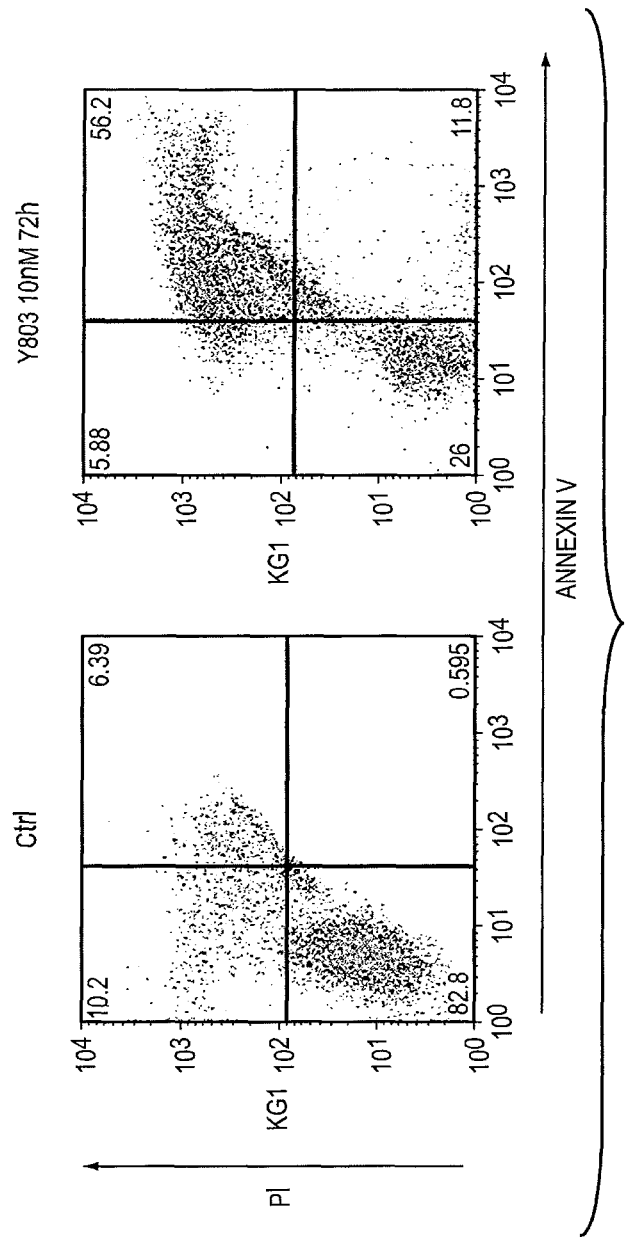
FIG. 16 illustrates apoptosis induced by lower doses of Compound (1-1). KG1 cells were incubated with 10 nM of Compound (1-1). Apoptotic cells were defined as Snnexin V+ with or without PI uptake. Representative dot plots are shown (PI: FL2, Annexin V: FL1).

Furthermore, Compound (1-1) induced cell cycle arrest in all cell lines (FIGS. 15A-15C). The apoptosis data showed that K562, KG1a and TOM-1 were less sensitive to cell cycle degradation after exposure to Compound (1-1). Of note, lower doses of Formula 2 (10 nM) induced apoptosis after prolonged incubation, i.e. 72 hours (as tested in KG1 cells and shown in FIG. 16).

TABLE 7

MTT assay at 72 h and GI50 values.

| Cell Line | GI50/nM | Range/nM |
|---|---|---|
| K562 | 11342.5 | 8352-14333 |
| HL60 | 1306.7 | 543-2298 |
| KG1 | 198.3 | 168.5-213.6 |
| KG1a | 1342.9 | 453.7-2214 |
| NOMO1 | 229.1 | 96.94-332.7 |
| Jurkat | 249.7 | 161.5-346.6 |
| RS4-11 | 34.2 | 29.24-38.84 |
| BV-173 | 161 | 105.5-207.6 |
| TOM-1 | 133.1 | 30.7-200.8 |

AML and ALL cell lines were exposed to increasing concentrations of compound (1-1), (0.1 nM-10 µM). Percent of proliferating cells were determined by MTT assay at 72 h and GI50 values were calculated by Prism software from means±SD from quintuplicates. GI50 values were expressed as means from 3 independent experiments.

Figures 39A, 39B, 39C:
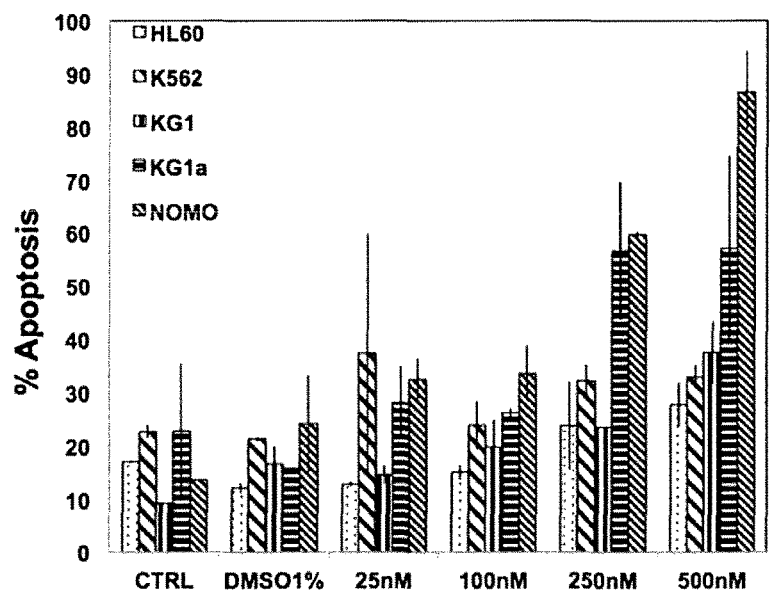
FIGS. 39A-39C illustrate kinetics of apoptosis induced by different doses of Compound (1-1) in AML and ALL cell lines. Myeloid and lymphoid cell lines were harvested at 72 h after treatment with increasing doses of Compound (1-1). Apoptotic cells were defined as annexin V+ with or without PI uptake. X-axis indicates doses of Compound (1-1) and Y-axis indicates percentage of apoptotic cells. Results are shown with mean±SD from duplicates of three independent experiments in AML and ALL cell lines upon treatment with Compound (1-1).
Figures 40A, 40B, 40C, 40D, 40E, 40F, 40G:
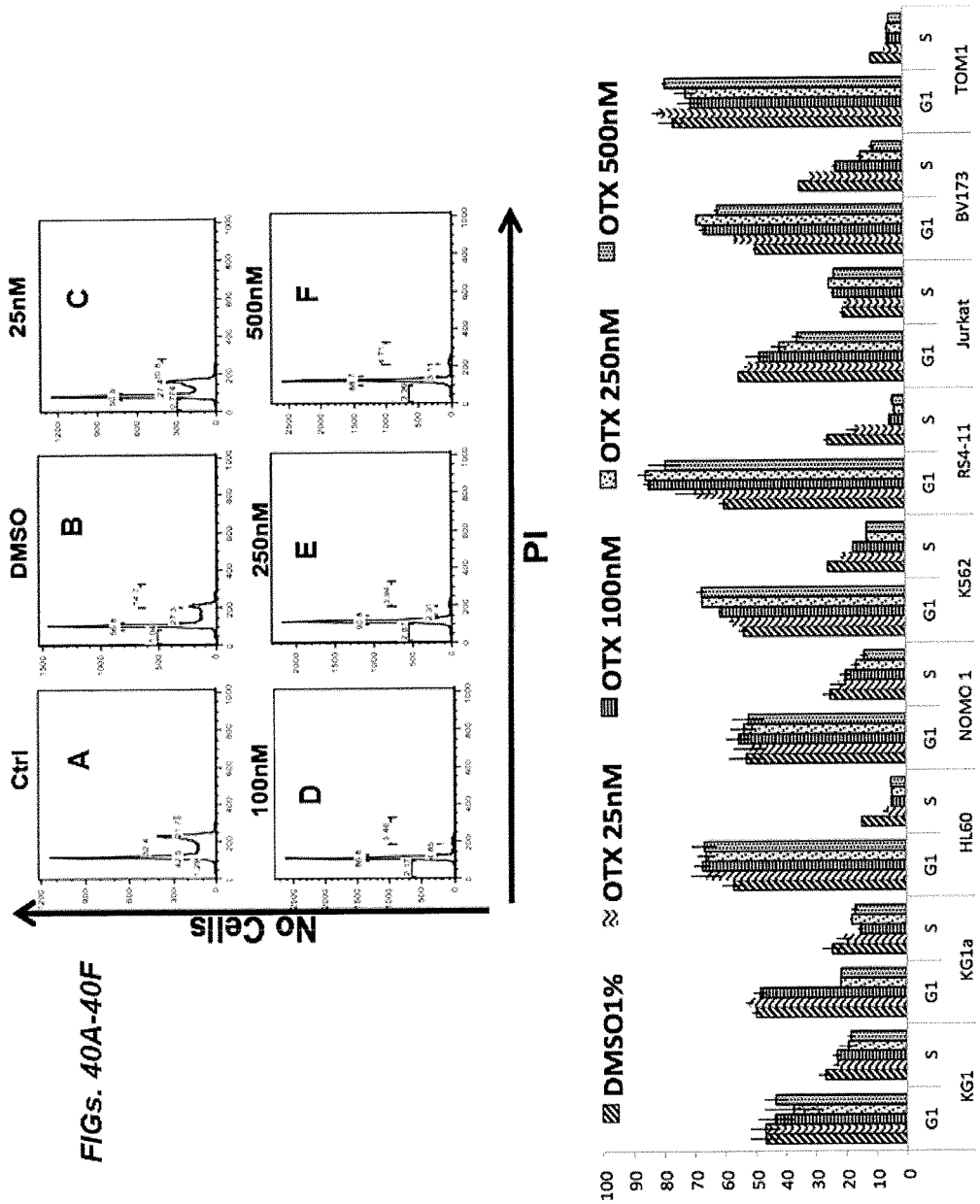

As shown in Table 7, compound (1-1) induced apoptosis in AML cell lines (see KG1a and NOMO1) and in ALL cell lines (see RS4-11, BV-173, Jurkat and TOM-1) in a dose-dependent manner increased when these cells were treated with different doses of compound (1-1) as detected by outer membrane phosphatidylserine exposure and propidium iodide incorporation at 72 h as illustrated in FIGS. 39A-39C. Among AML cell lines, 2 appeared sensitive (KG1 and NOMO1) with GI50 values of 198.3 and 229.1 nM respectively. Two cell lines were less sensitive (HL60 and KG1a) with GI values of 1.3 µM each while K562 were considered resistant with an GI50 value of 11.3 µM. OTX015 caused a dose-dependent decrease in cell viability in all ALL cell lines, with GI50 between 34.2-249.7 nM Generally, the half maximal inhibitory concentration (IC-50 value) of a compound is a measure of the effectiveness of the compound in inhibiting a biological or a biochemical function. IC-50 value, therefore, can be considered a quantitative measure indicating how much of a particular drug or any chemical substance is required to inhibit a given biological process by half (50%). Sometimes, however, GI-50 is used to symbolize the value for the concentration that causes 50% growth inhibition. The use of GI-50 indicates that a correction for the cell count at time zero has been made. An example of one formula for calculating GI-50 value defines GI-50 as the concentration of test compound where $100\times(T-T_0)/(C-T_0)=50$, wherein T is the optical density of the test well after a 48 h period of exposure to test drug is T, for example; $T_0$ is the optical density the test well at time zero.

Furthermore, compound (1-1) decreased S phase fraction in almost all cell lines (FIGS. 40A-40H). This effect was more pronounced in the ALL cell lines RS4-11 and BV-173 with accumulation in G1 in those cell lines.

Example 9: Expression of Bromodomains

Expression of bromodomains was studied in different cell lines and patient samples using quantitative-real time polymerase chain reaction (QT-PCR) analysis. The total RNA obtained after extraction with a reagent solution of phenol and guanidine isothiocyanate (TRIzol® brand reagent, Invitrogen, Grand Island, N.Y.) was titrated to 1 µg/µL and stored at −80° C. The complementary DNA (cDNA) was synthesized from 1 µg RNA. The QT-PCR reactions were performed in a volume of 25 µL, from a tenth of the cDNA (equivalent to 100 ng of RNA) on a thermocycler ABI 7900HT in standard mode (1 cycle of 2 minutes at 50° C.-10 minutes at 95° C. followed by 50 cycles of 15 seconds at 95° C.-1 minute at 6° C.).

The different cell lines expressed BRD2, BRD3 and BRD4 at different levels as detected by QT-PCR (FIG. 17A-17C). Three different forms of BRD4 were studied: the consensus form (BRD4c), an intermediate form, and a short form (BRD4s). There was no difference for the expression of the different forms among cell lines. There was no obvious correlation between apoptosis and BRD expression. The AML cell line K562 had the lowest expression level and had lower sensitivity to Compound (1-1) treatment. There was no difference between BRD expression levels compared to the breast cancer cell line MCF-7. Very high levels of BRD were observed in selected CD34+ cells from cord blood. Expression of BRD2, BRD3 and BRD4 was studied in patient samples. Patient characteristics are summarized in Table 8. Among ALL patients, Ph+ ALL showed lower BRD expression levels while BRD expression levels among AML patients was more heterogeneous (FIG. 17A-17C).

TABLE 8

ALL and AML patient characteristics

| Patient | Leukemia | Cytogenetics | Genetics | Blast percentage |
|---|---|---|---|---|
| 1 | B-ALL | normal | unk | 79 |
| 2 | B-ALL | normal | unk | 25 |
| 3 | B-ALL | Ph1+ | BCR/ABL | na |
| 4 | B-ALL | Ph1+ | BCR/ABL | 90 |
| 5 | B-ALL | Ph1+ | BCR/ABL | 27 |
| 6 | B-ALL | Ph1+ | BCR/ABL | 74 |
| 7 | T-ALL | unk | unk | na |
| 8 | T-ALL | unk | unk | 96 |
| 9 | T-ALL | unk | unk | 46 |
| 10 | T-ALL | normal | CALM/AF10 | na |
| 11 | AML | normal | CEBPA+ | 52 |
| 12 | AML | normal | MLL-PTD | 75 |
| 13 | AML | normal | MLL-PTD | 88 |
| 14 | AML | normal | FLT3-TTD | 90 |
| 15 | AML | normal | FLT3-ITD | 19 |
| 16 | AML | normal | FLT3-ITD | 92 |
| 17 | AML | normal | FLT3-ITD and MLL-PTD | 47 |
| 18 | AML | inv(16) | CBFB/MYH11 | 40 |
| 19 | AML | inv(16) | CBFB/MYH11 | na |
| 20 | AML | complex | unk | 93 |
| 21 | AML | complex | unk | 22 |
| 22 | AML | normal | NPM1+ | 49 |
| 23 | AML | normal | NPM1+ | 13 |
| 24 | AML | normal | NPM1+ | 20 |
| 25 | AML | normal | NPM1+ | 90 |
| 26 | AML | normal | NPM1+ | 24 |
| 27 | AML | normal | NPM1+ and FLT3-ITD | 94 |
| 28 | AML | t(8; 21) | AML1/ETO | 89 |
| 29 | AML | t(8; 21) | AML1/ETO | 49 |

Figure 18A:
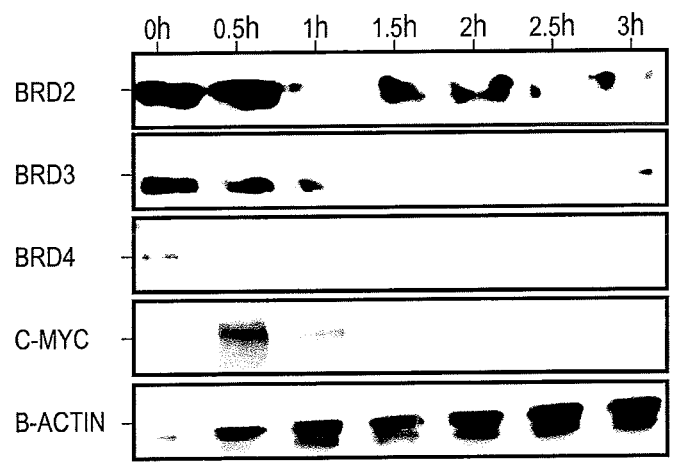
FIGS. 18A and 18B illustrate down regulation of BRD proteins and c-MYC upon Compound (1-1) treatment. Cell lysates and cDNA extractions were obtained from different ALL and AML cell lines. Protein and cDNA levels were studied by immunoblot (FIG. 18A) and QT-PCR (FIG. 17B).
Figure 18B:
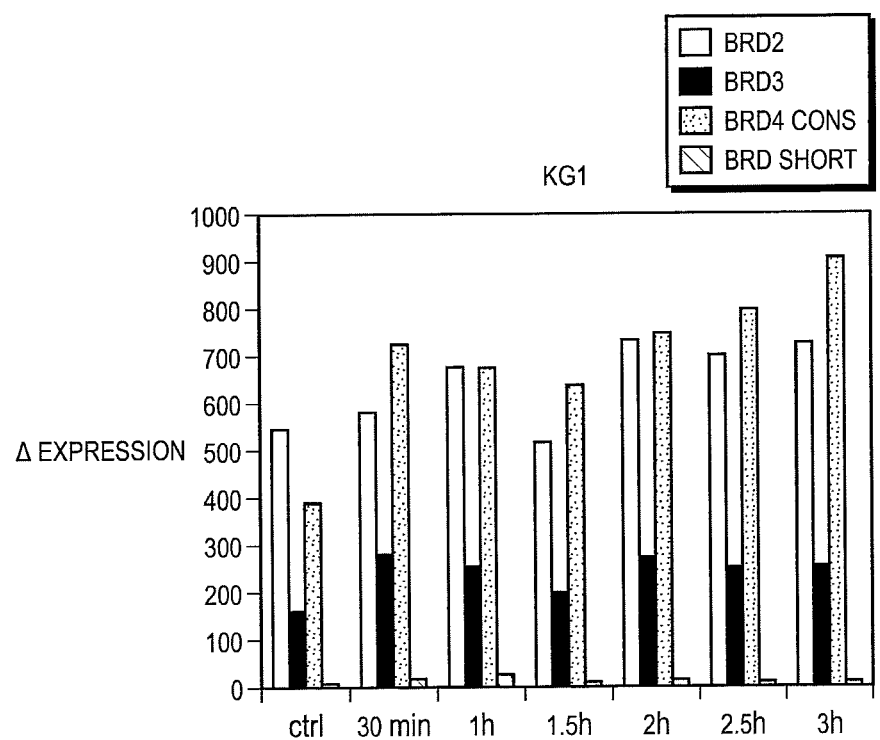

Treatment with Compound (1-1) was studied to determine if it induces down-regulation of BRD2, BRD3, BRD4 and c-MYC. The oncogene c-MYC is a downstream partner of BRD4 for leukemia maintenance (Delmore, J. E, et al. Cell. 2011; 146:904-917). Other small inhibitors such as JQ1 induce BRD4 down-regulation and subsequently c-MYC down-regulation. Different leukemia cell lines were treated with 100 nM Formula 2 and observed rapid down-regulation of BRD2, BRD3 and BRD4 associated with c-MYC down-regulation within 3 hours at the protein level (FIGS. 18A and 18B). In KG1 and KG1a protein down-regulation was not associated with cDNA decrease (FIGS. 18A and 18B) compared to TOM-1 cells (FIGS. 19A-19D) within 3 hours. In Jurkat and RS 4-11 cells, cDNA for BRD 2-4 was initially down-regulated but increased before 3 hours (FIG. 19A-19D). The results show that Formula 2 induces rapid down-regulation of BRD2, BRD3, BRD4 and c-MYC.

Figures 41A, 41B:
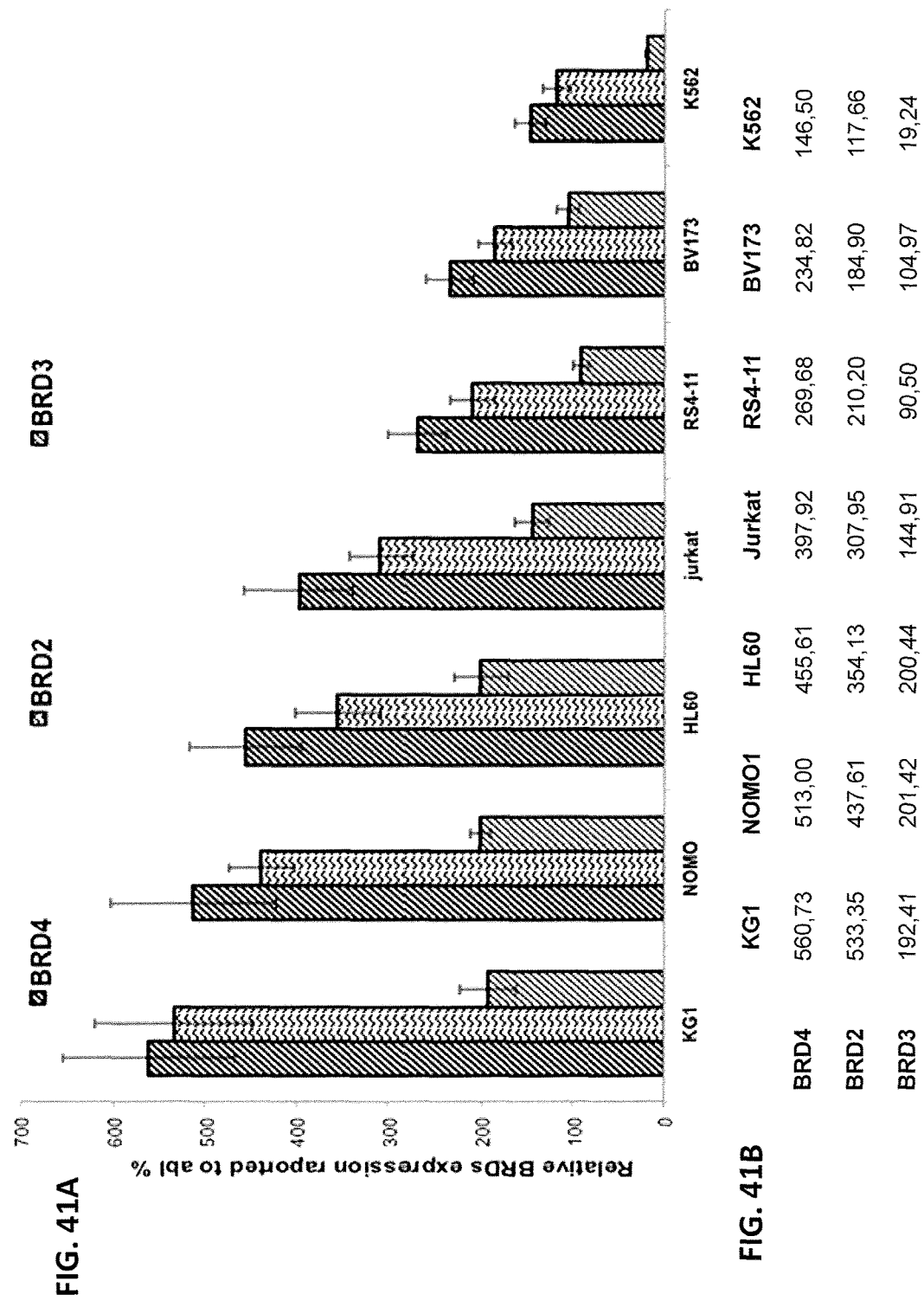
FIGS. 41A and 41B illustrate gene expression of bromodomains in leukemia cell lines and modulation by Compound (1-1) (OTX015). The different cell lines expressed BRD2, BRD3 and BRD4 at heterogeneous levels as detected by RQ-PCR with bcr-abl driven cell lines BV-173 and K562 having the lowest gene expression levels (FIG. 41A).
Figures 41E, 41F:
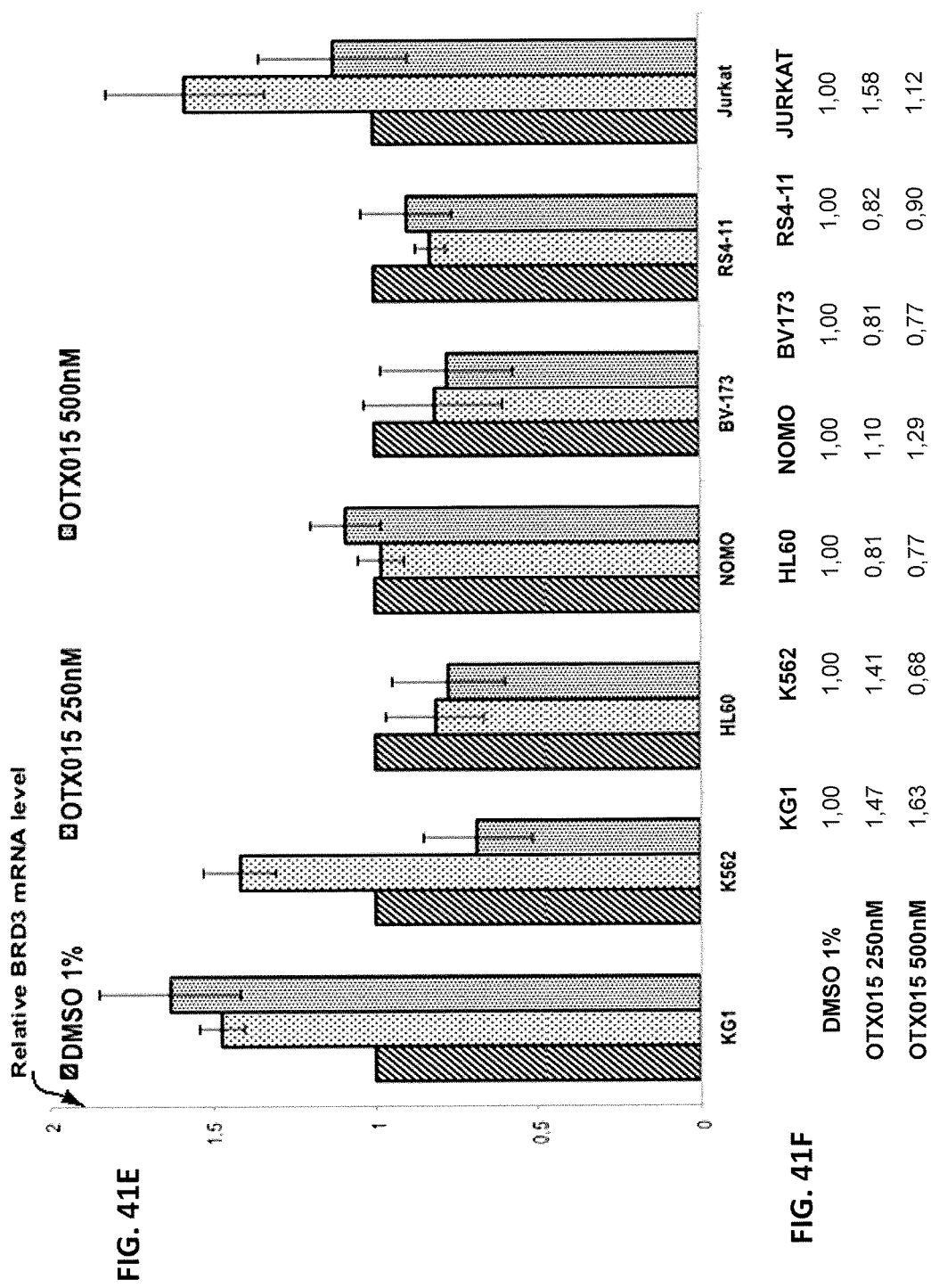

Further as illustrated in FIGS. 41A-41H, the different cell lines expressed BRD2, BRD3 and BRD4 at heterogenous levels as detected by RQ-PCR with bcr-abl driven cell lines BV-173 and K562 having the lowest gene expression levels (FIGS. 41A-41B). There was no obvious correlation between biologic effects including MTT, apoptosis or cell cycle arrest and BRD gene expression. We investigated modulation of BRD4, BRD2 and BRD3 at the cDNA level by OTX015 treatment with 250 nM and 500 nM respectively at 48 h. We were not able to detect a consistent down regulation of BRD4, BRD2 or BRD3 (FIG. 41C-41H) by Compound (1-1) treatment while a significant upregulation of BRD3 and BRD2 in KG1, K562 and Jurkat and increase of BRD2 in KG1 and HL60 are detected.

Example 10: Efficacy of Compound (1-1) to Induce Apoptosis in CD34$^+$ and CD34$^-$ Cells The efficacy of Compound (1-1) to induce apoptosis in primary cells was investigated. CD34+ and CD34− cells were obtained by positive selection with CD34+ microbeads from cord blood (healthy controls) and one AML patient. Routine immunophenotyping showed that 30% of blast cells were positive for CD34+. Treatment of CD34+ and CD34− cord blood cells demonstrated toxicity for immature CD34+ cells at the 500 nM dose level while the mature compartment remained unaffected (FIG. 20). Treatment of CD34$^+$ and CD34$^-$ AML cells showed in vitro induction of apoptosis in a dose dependent manner.

Apoptosis patterns for CD34$^-$ at 24 hours at different concentrations of Compound (1-1) are illustrated in FIGS. 32A-32C.

Example 11: Apoptosis after Short Exposure to Compound (1-1)

Figures 21A, 21T:
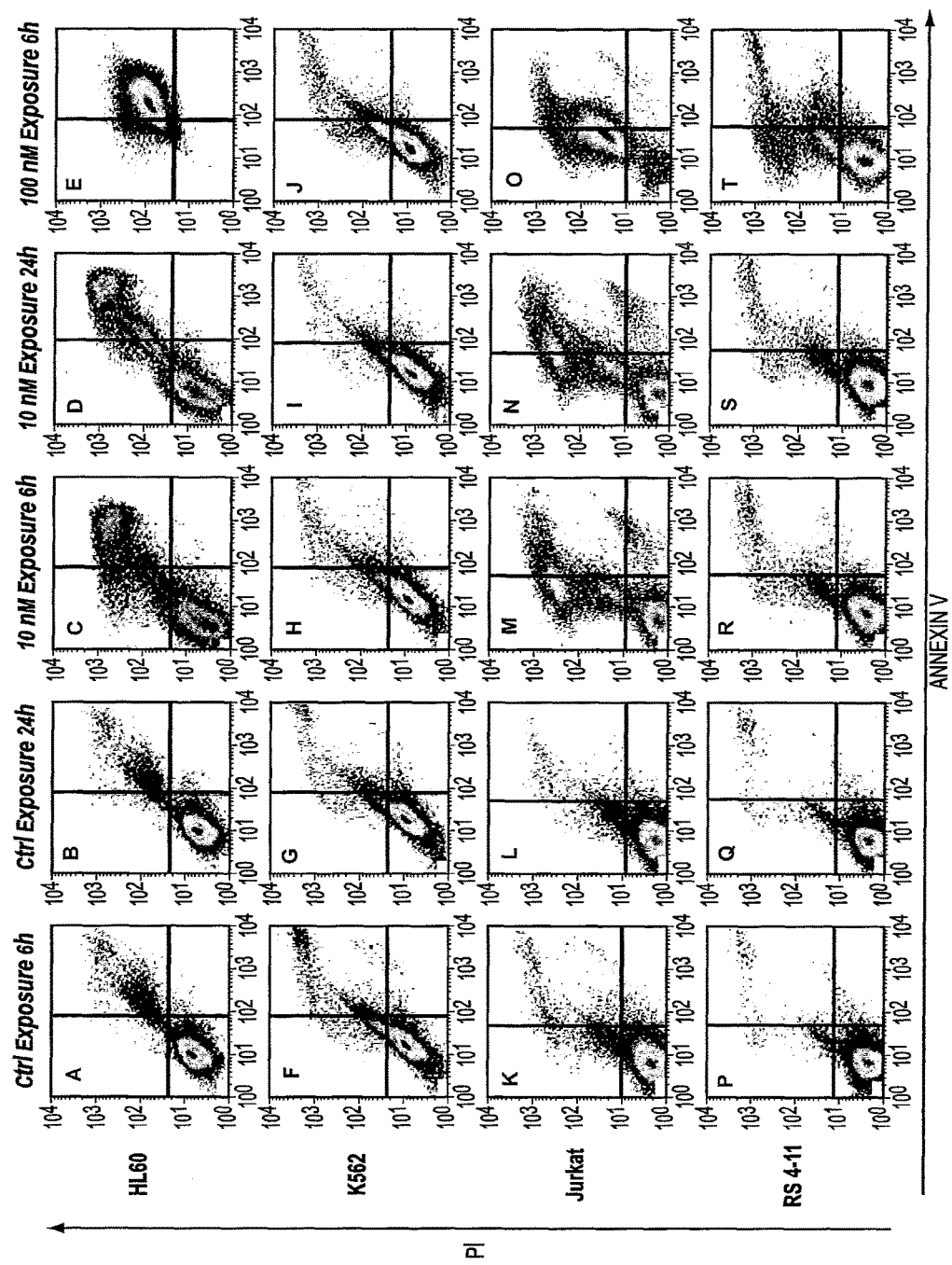
FIGS. 21A-21T illustrate flow cytometric analysis of apoptosis in ALL cell lines (Jurkat, and RS 4-11) and AML cell lines (HL60 and K562) at 96 hours after short exposure to Compound (1-1) at concentrations of 10 nM and 100 nM.
Figure 22A:
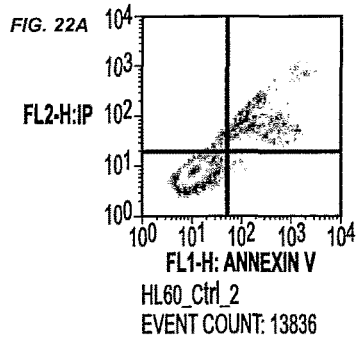
FIGS. 22A-22L illustrate flow cytometric analysis of apoptosis in AML cell line HL60 after short exposure to Compound (1-1) at concentrations of 0 nM, 1 nM, and 10 nM.
Figure 22B:
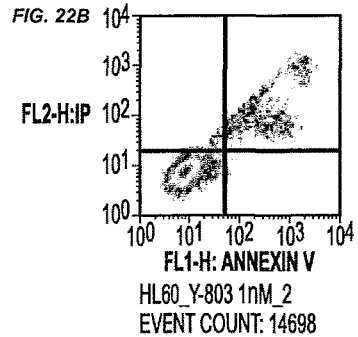
Figure 22C:
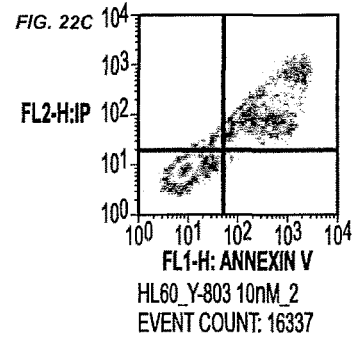
Figure 22D:
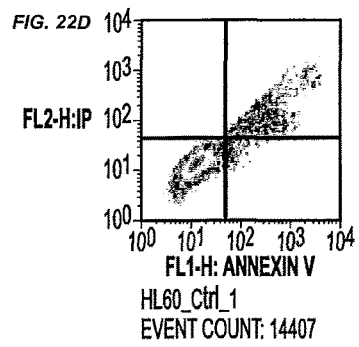
Figure 22E:
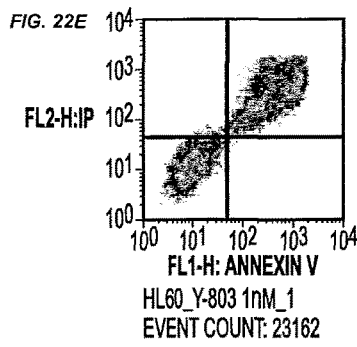
Figure 22F:
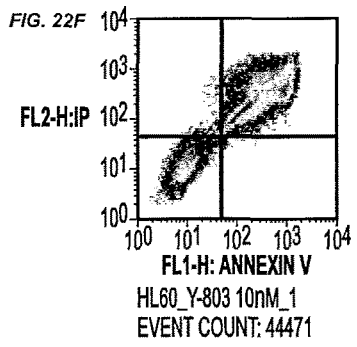
Figure 22G:
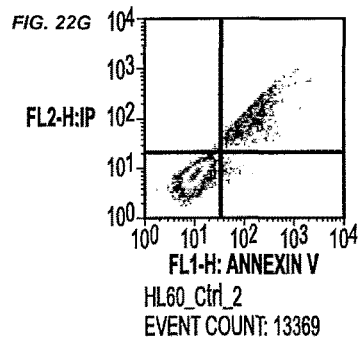
Figure 22H:
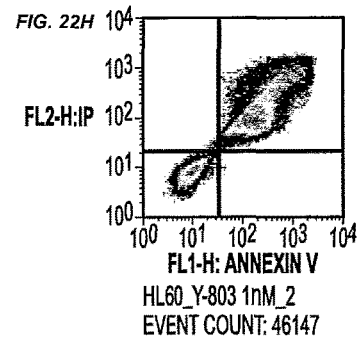
Figure 22I:
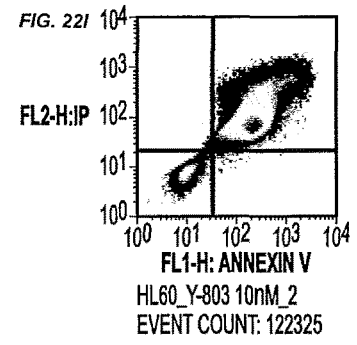
Figure 22J:
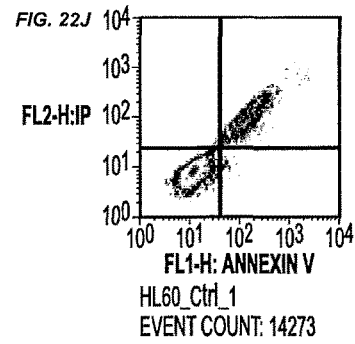
Figure 22K:
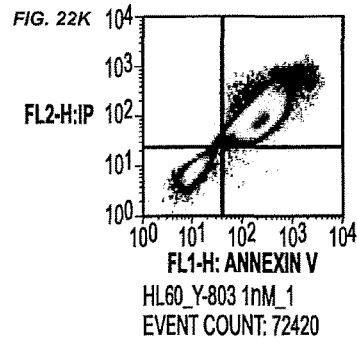
Figure 22L:
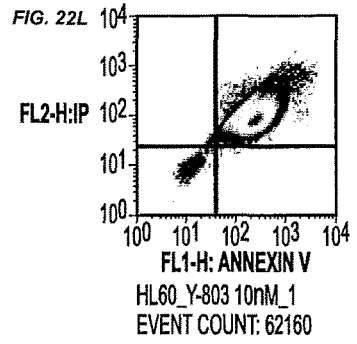

FIGS. 21A-21T show apoptosis at 96 hours after short exposure to Compound (1-1). HL60, KS62, Jurkat, and RS4-11 cells were treated with 10 nM and 100 nM of Compound (1-1), respectively. Cells were washed at 6 hours (10 nM and 100 nM) and 24 hours (10 nM), supernatant was discarded and cells seeded again in fresh medium. Apoptotic cells were assessed by FACS analysis at 96 hours (24 to 72 hours not shown) and defined as Annexin V+ with or without PI uptake. One representative experiment of two is shown in FIGS. 21A-21T.

Example 12: Apoptosis after Exposure to Various Concentrations of Compound (1-1)

Figure 23A:
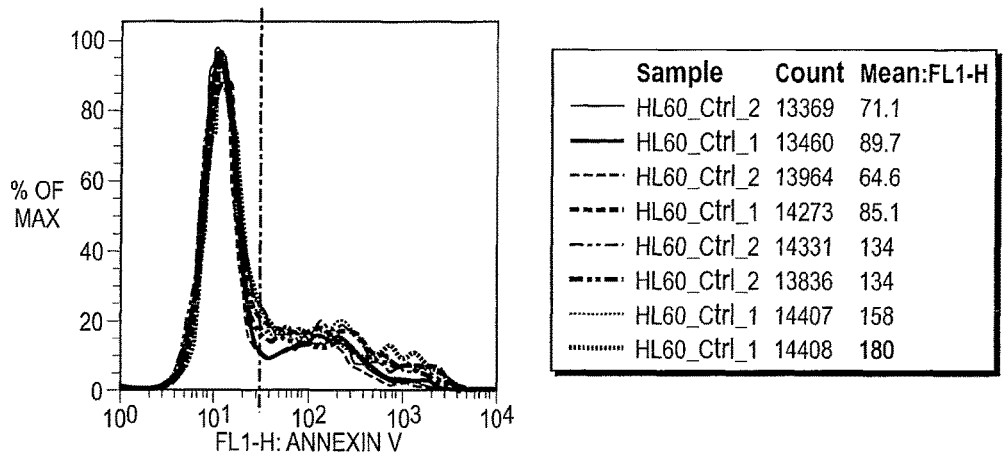
FIGS. 23A, 23B and 23C illustrate apoptosis for HL60 cell line of FIGS. 22A-22L.
Figure 23B:
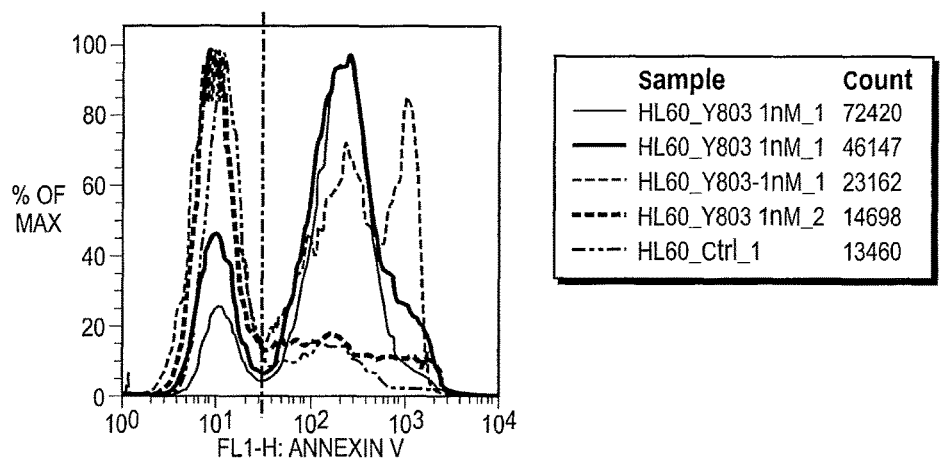
Figure 23C:
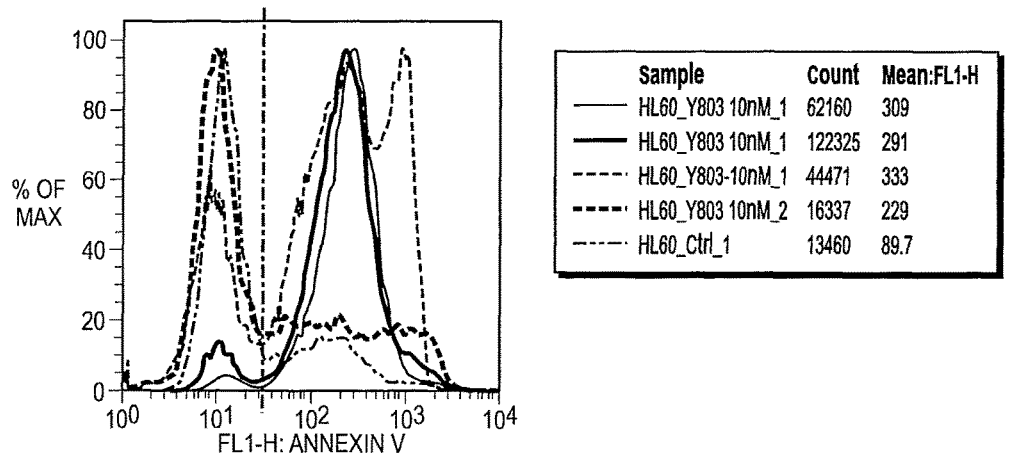

FIGS. 22A-22L illustrate flow cytometric analysis of apoptosis data in the AML cell line HL60 when exposed to 0 nM, 1 nM and 10 nM of Compound (1-1). FIGS. 23A, 23B and 23C illustrate apoptosis for HL60 cell lines of FIGS. 22A-22L.

Figures 24A, 24B:
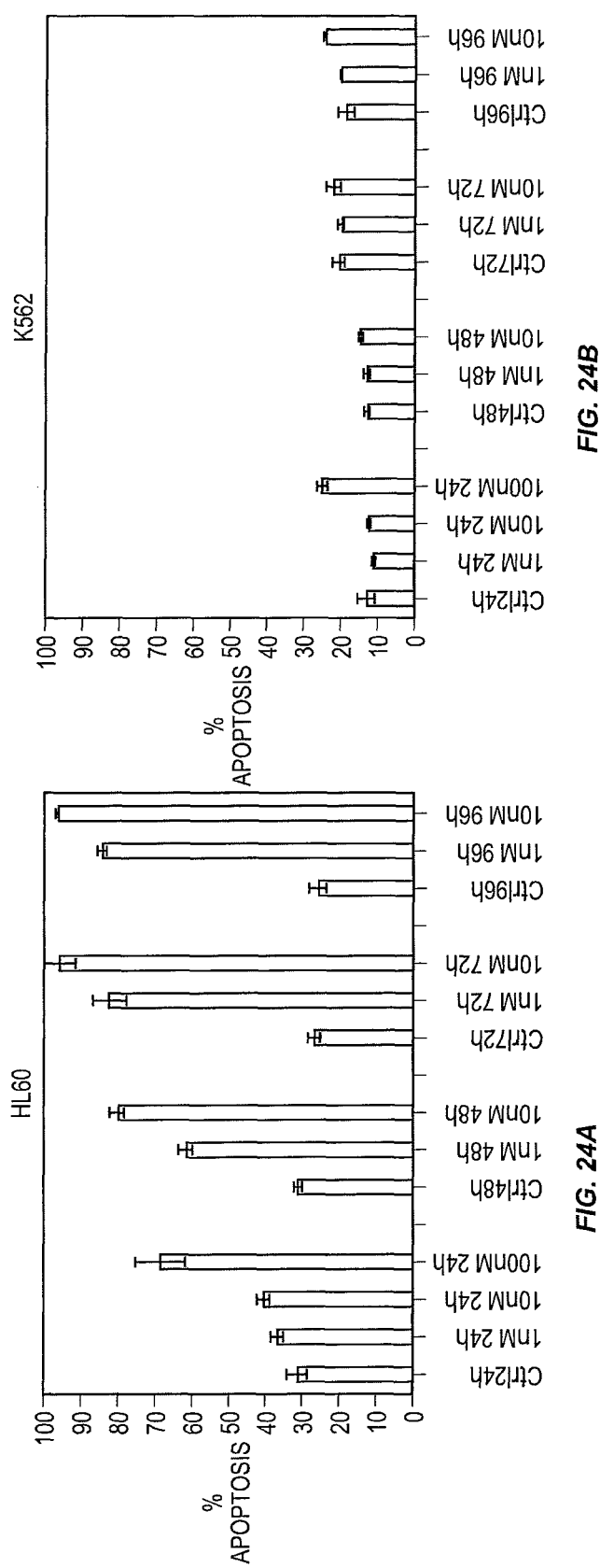
FIGS. 24A and 24B illustrate apoptosis for HL60 and K562 cell lines.
Figures 25A, 25B:
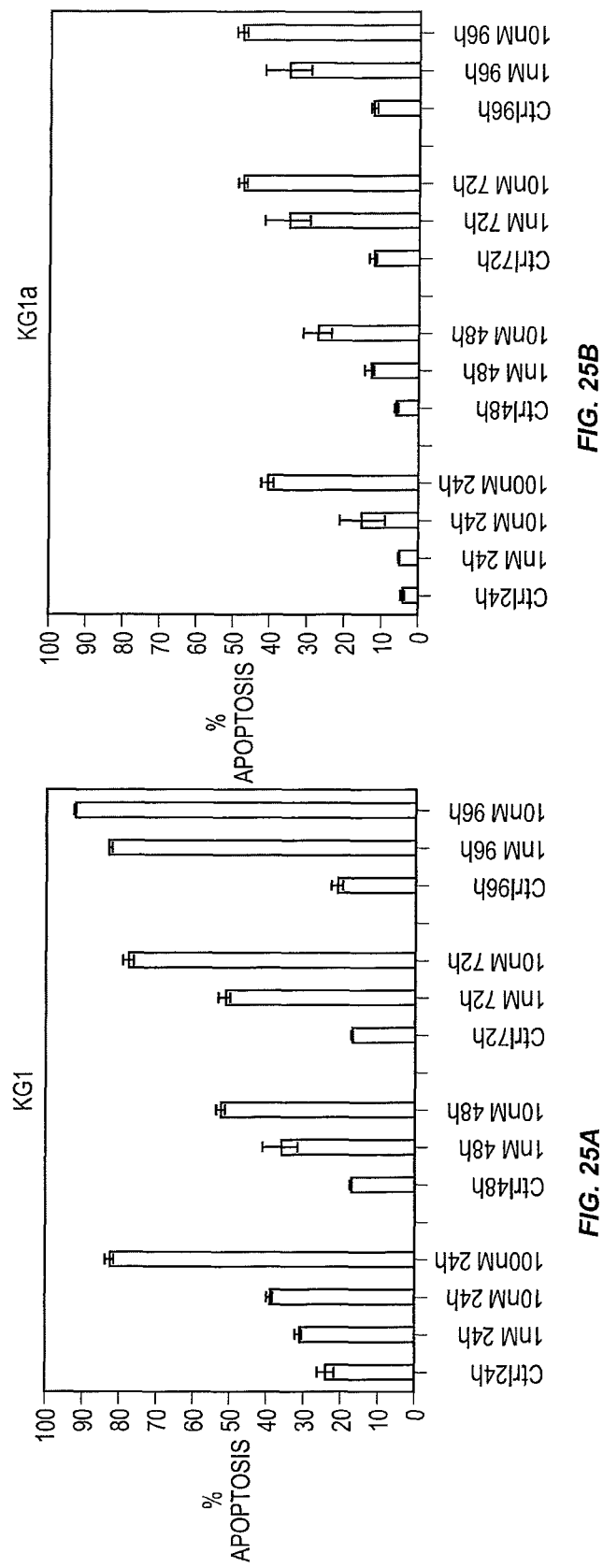
FIGS. 25A and 25B illustrate apoptosis for KG1 and KG1a cell lines
Figures 26A, 26B:
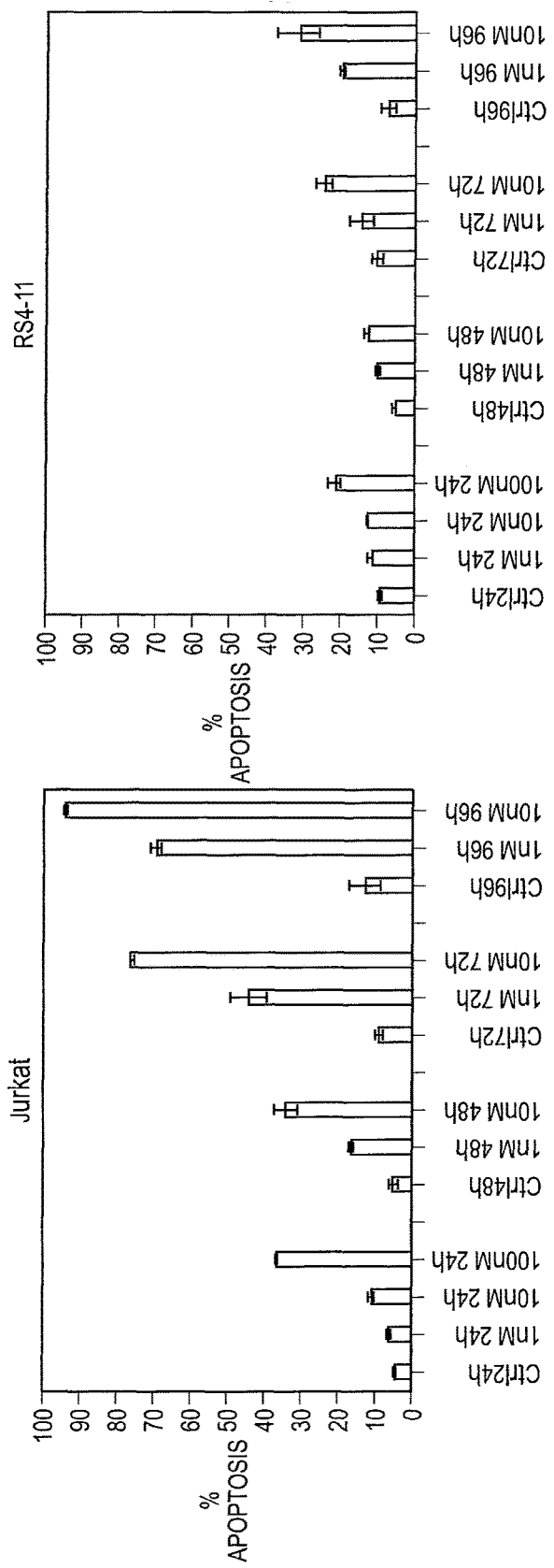
FIGS. 26A and 26B illustrate apoptosis for Jurkat and RS4-11 cell lines.
Figure 27:
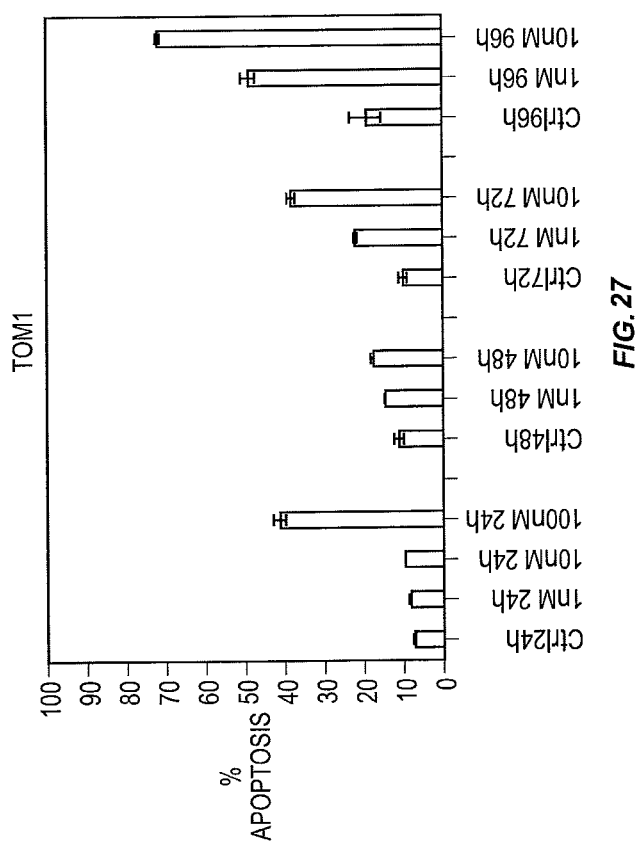
FIG. 27 illustrates apoptosis for the TOM1 cell line.

Treatment with Compound (1-1) induced significant apoptosis in HL60 and K562 cells (FIGS. 24A and 24B, respectively). Significant apoptosis was also observed in KG1 and KG1a cells (FIGS. 25A and 25B), Jurkat and RS4-11 cells (FIGS. 26A and 26B), and TOM1 cells (FIG. 27). K562 was less sensitive to treatment with Compound (1-1), with 20% apoptopic cells observed at 24 hours. Prolonged exposure at 1 and 10 nM concentrations yielded different response patterns: after an exposure of 96 hours at 10 nM only, HL60, KG1 and Jurkat cells displayed >90% and TOM-1 70% apoptosis; in contrast, KG1a, MLL-fusion RS4-11 and K562 cells displayed lower apoptosis (45%, 30% and 20%, respectively), while apoptosis was observed at levels of 15% to 20% in controls.

Example 13: Apoptosis Following Drug Washout

Figure 28:
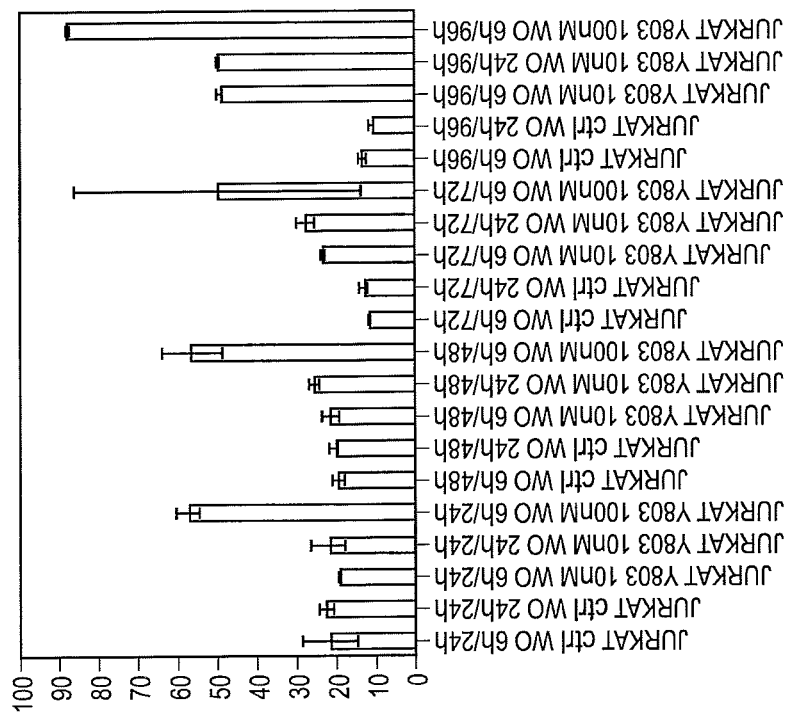
FIG. 28 is a plot of apoptosis after drug washout from Jurkat cell line.
Figures 29A, 29B:
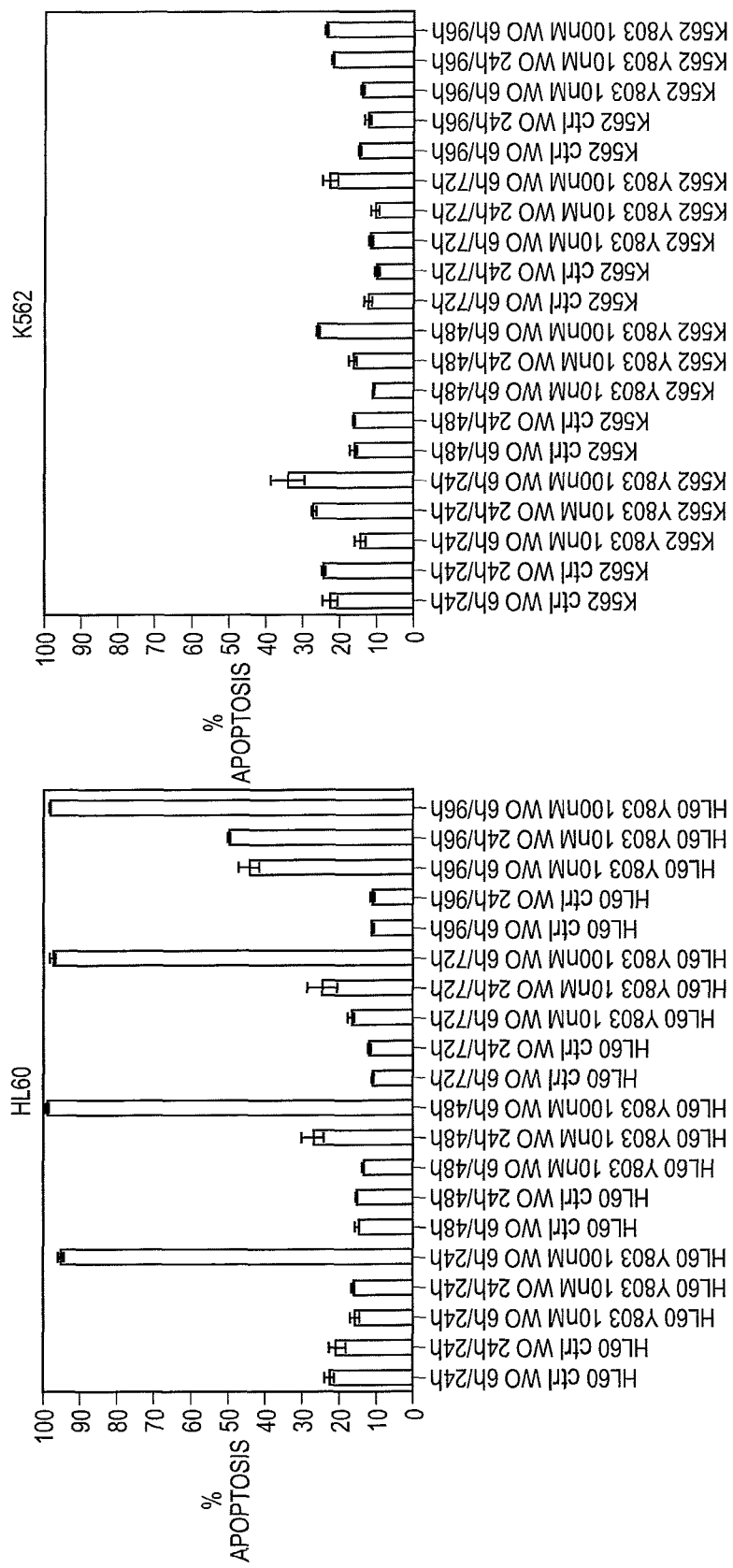
FIGS. 29A and 29B are plots of apoptosis after drug washout from HL60 and K562 cells.
Figures 30A, 30B:
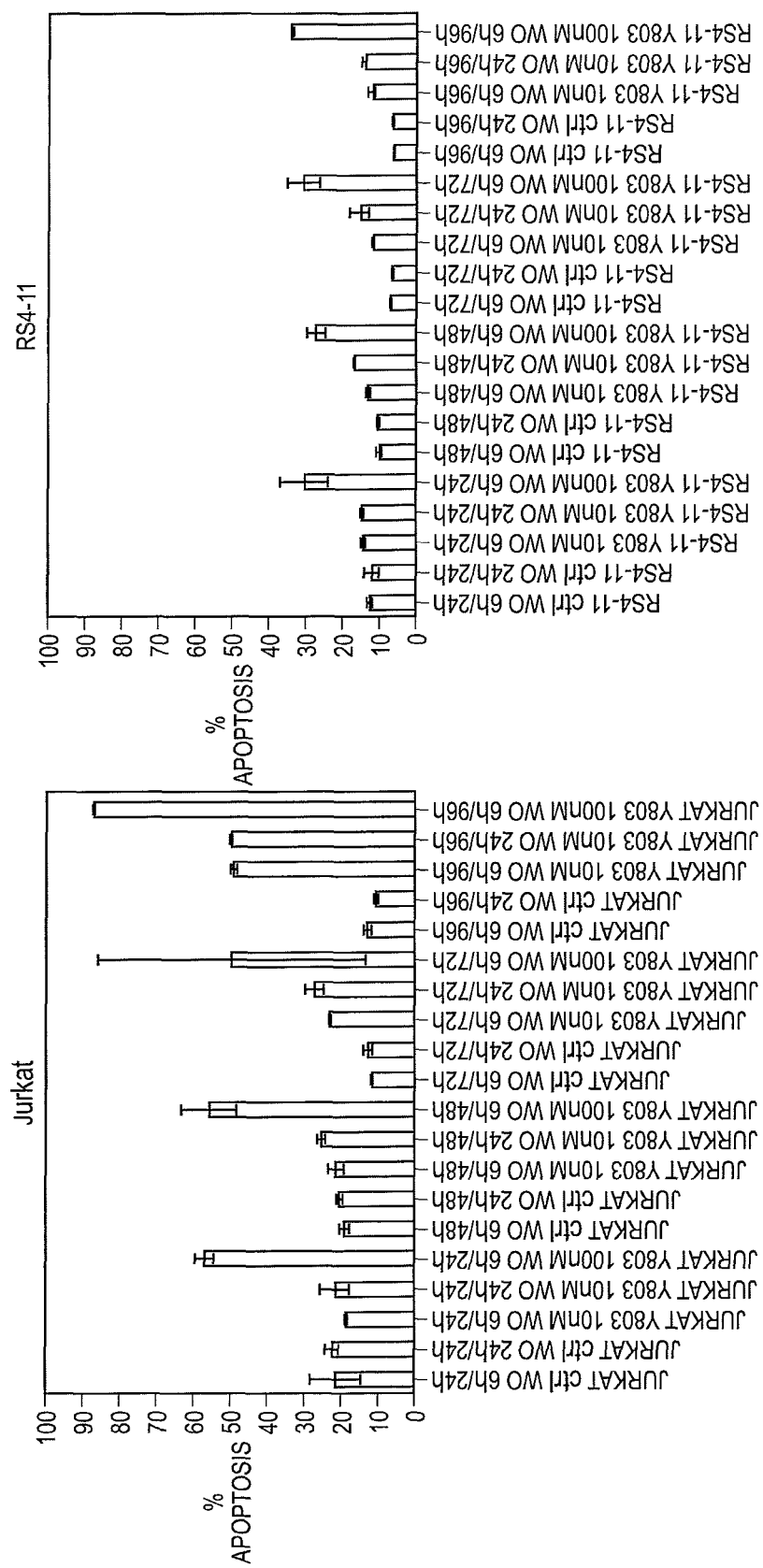
FIGS. 30A and 30B are plots of apoptosis after drug washout from Jurkat and RS4-11 cells.

Drug washout after a shorter exposure of 6 hours was also associated with significant delayed apoptosis at 96 hours in the sensitive HL60 and Jurkat lines (FIGS. 28 and 29A, 29B, respectively), but not in the less sensitive K562 and RS4-11 cell lines (FIGS. 30A and 30B).

Figure 31A:
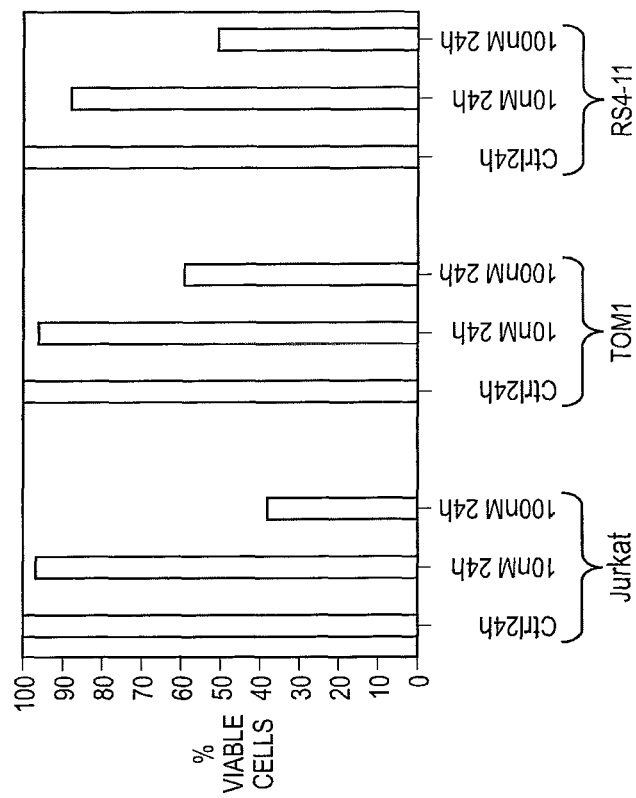
FIGS. 31A and 31B illustrate an MTT assay in three ALL cell lines (Jurkat, RS 4-11, TOM-1) and four AML cell lines (HL60, K562, KG1 and KG1a).
Figure 31B:
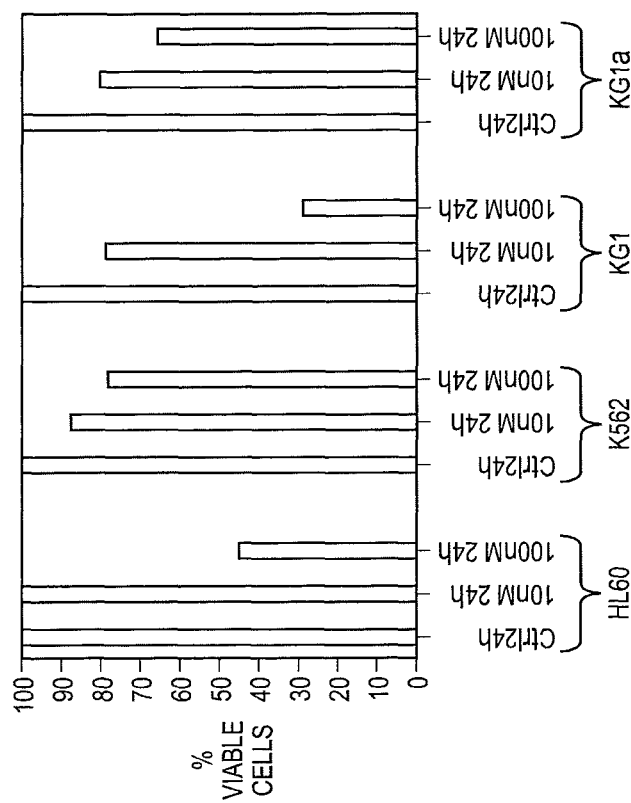
Figure 34A:
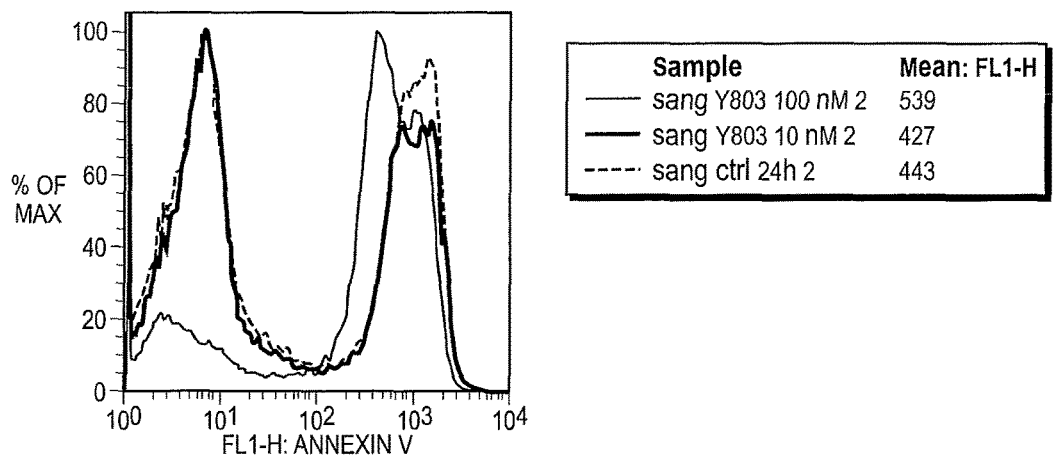
FIGS. 34A and 34B show apoptosis patterns in AML patients.
Figure 34B:
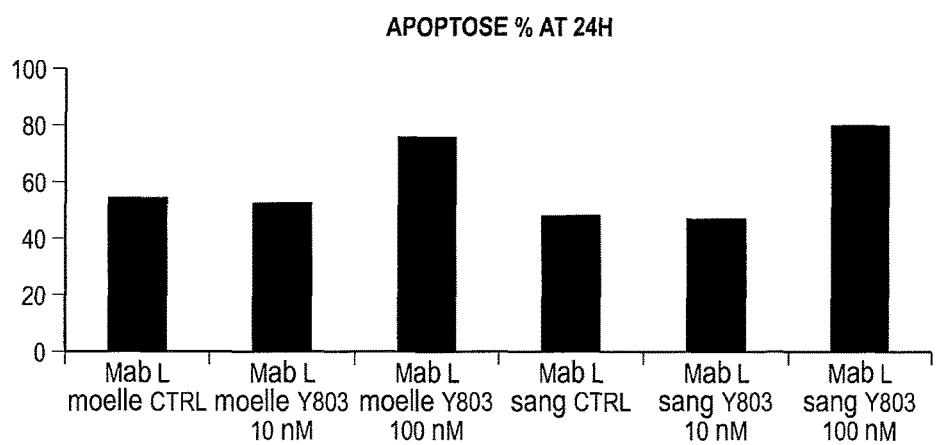

MTT assay data in three ALL cell lines are shown in FIGS. 31A and 31B.

Example 14: Apoptosis in Blood and Marrow

FIGS. 33A-33G and 34A-34B illustrate the apoptosis for various concentrations of Compound (1-1) for blood and marrow cells.

Figure 35:
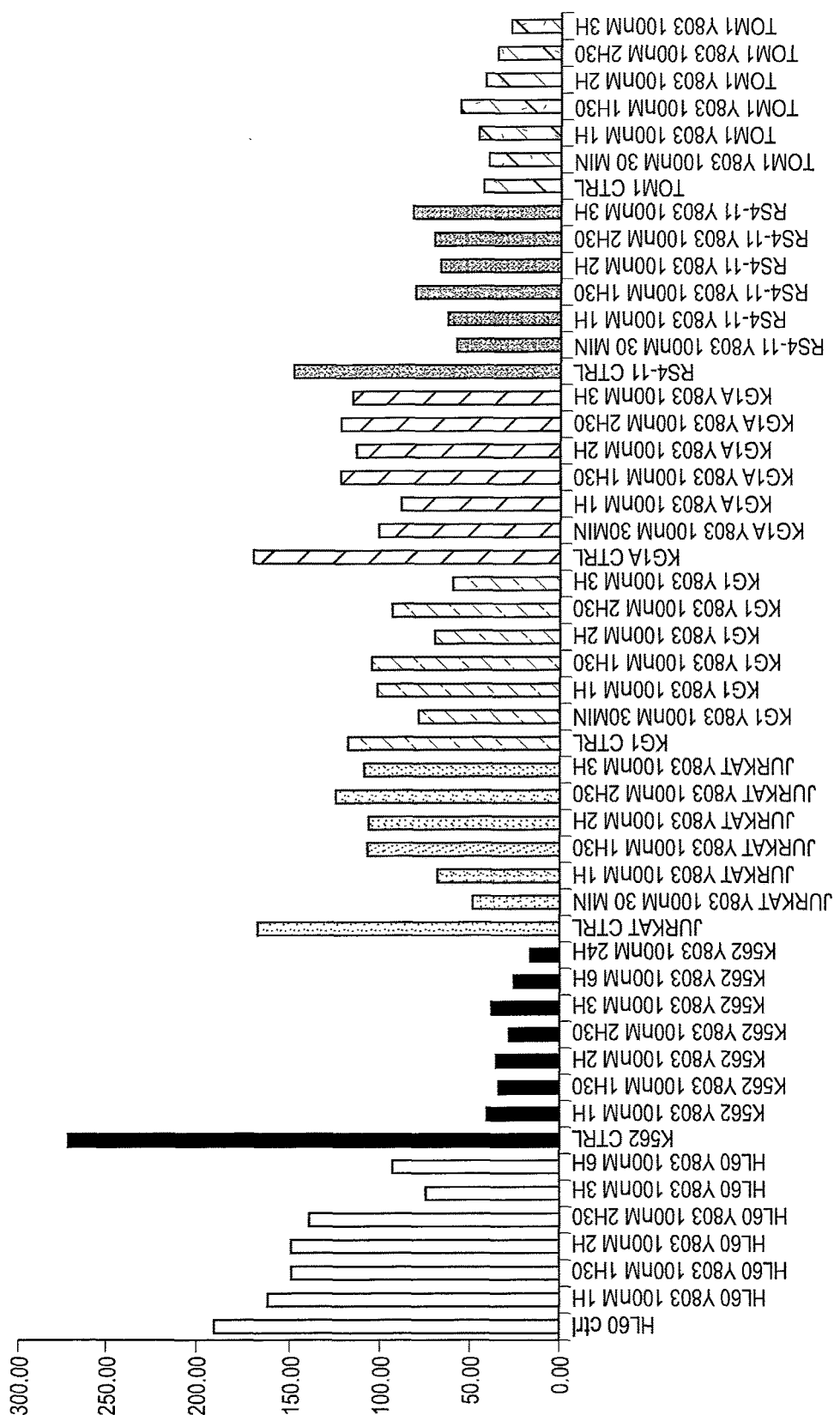
FIG. 35 illustrates c-MYC kinetics in AML and ALL cell lines upon treatment with Compound (1-1).
Figure 36:
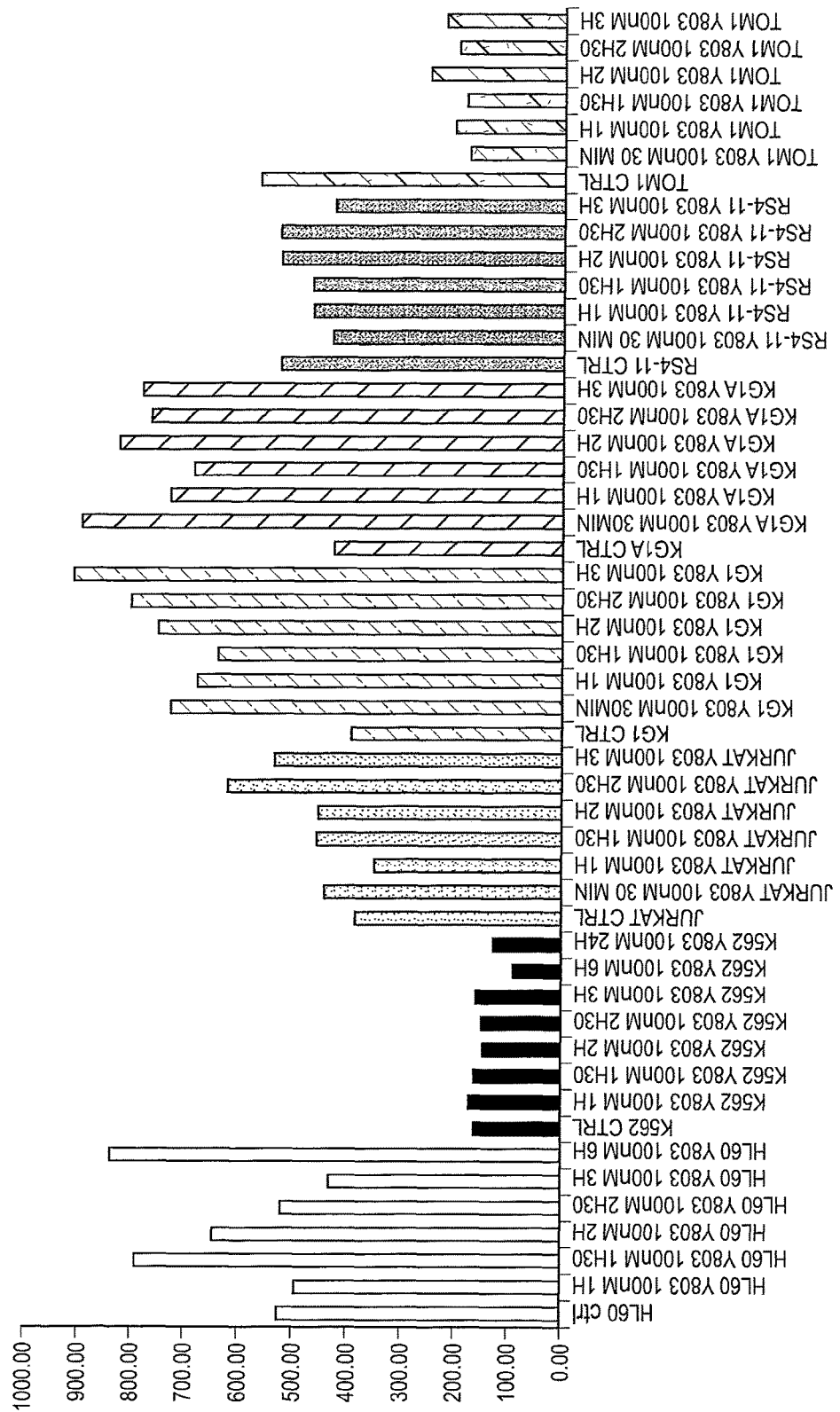
FIG. 36 illustrates BRD4 kinetics in AML and ALL cell lines upon treatment with Compound (1-1).
Figure 37:
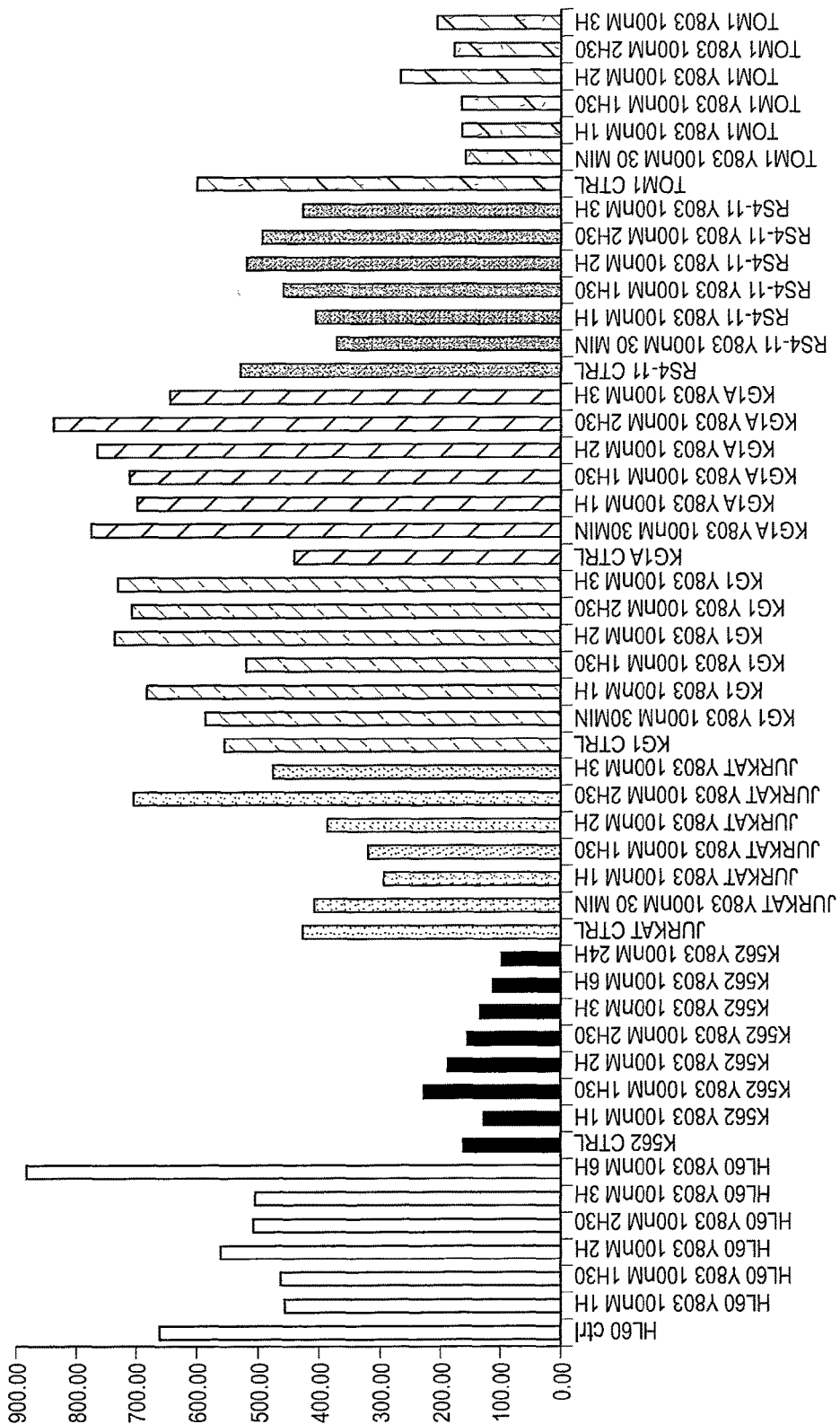
FIG. 37 illustrates BRD2 kinetics in AML and ALL cell lines upon treatment with Compound (1-1).
Figure 38:
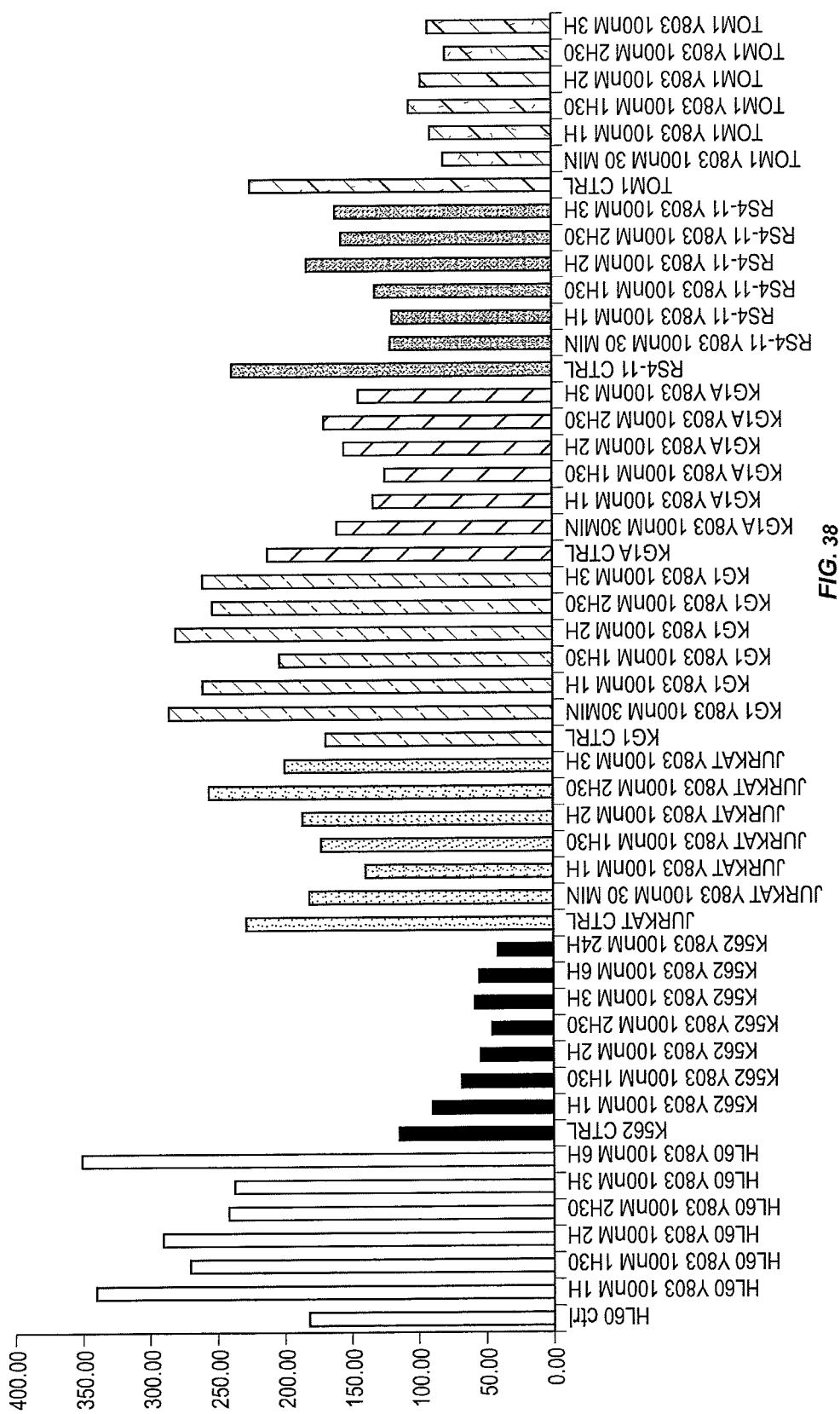
FIG. 38 illustrates BRD3 kinetics in AML and ALL cell lines upon treatment with Compound (1-1).

Example 15: c-MYC Kinetics c-MYC kinetics in AML and ALL cell lines were measured upon treatment with Compound (1-1) and are shown in FIG. 35. BRD4 kinetics in AML and ALL cell lines were also measured upon treatment with Compound (1-1) and are shown in FIG. 36. FIG. 37 illustrates BRD2 kinetics in AML and ALL cell lines upon treatment with Compound (1-1). FIG. 38 illustrates BRD3 kinetics in AML and ALL cell lines upon treatment with Compound (1-1).

Figures 42A, 42B:
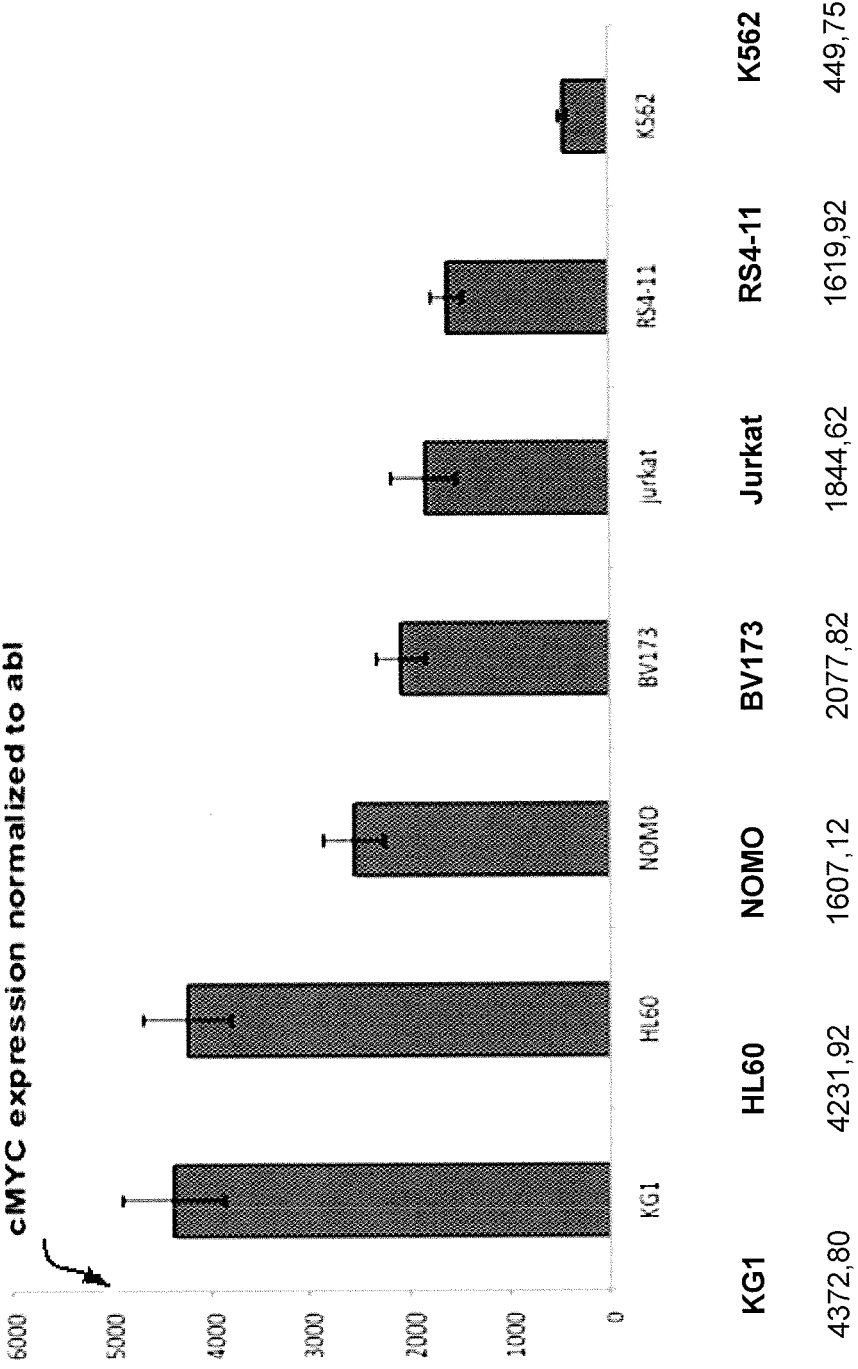
FIGS. 42A-42D illustrates OTX015 inducing downregulation of c-MYC in all cell lines. Basal gene expression levels of c-MYC in different leukemia cell lines are shown FIGS. 42A and 42B). Different leukemia cell lines treated with 250 nM and 500 nM of OTX015 and c-MYC downregulation detected by QT-PCR at 48 h are shown in FIGS. 42C and 42D.
Figures 42C, 42D:
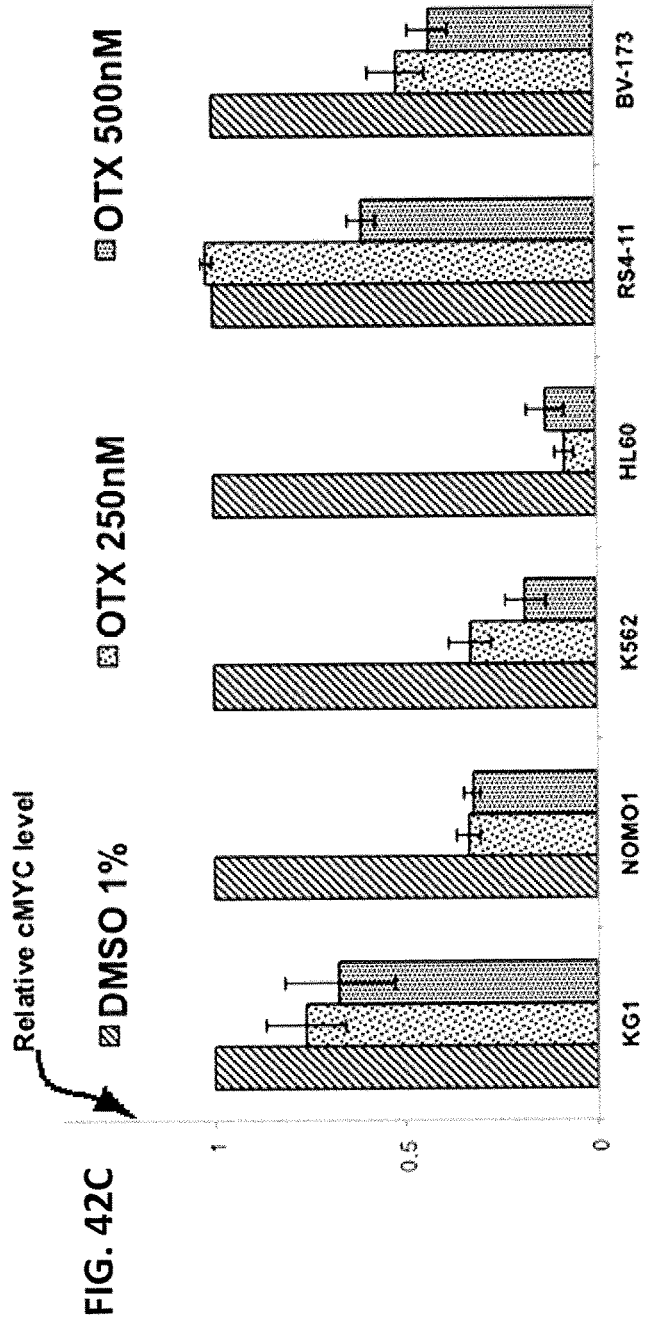

The oncogene c-MYC is thought to be activated by BRD4 and is crucial for leukemia maintenance. Other small BRD inhibitors (i.e. JQ1) induced BRD4 downregulation and subsequently c-MYC downregulation in different settings. We determined basal gene expression levels of c-MYC in different leukemia cell lines showing heterogeneous results without clear correlation to biologic effects of Compound (1-1) in regard to MTT, apoptosis or cell cycle effects (FIGS. 42A and 42B). Those cell lines were treated with 250 nM and 500 nM of Compound (1-1) and c-MYC downregulation was observed in all cell lines as detected by QT-PCR at 48 h (FIGS. 42C and 42D).

Due to the absence of clear correlations of BRDs and c-MYC basal gene expression and modulation by Compound (1-1) detected by RQ-PCR we next investigated potential effects of Compound (1-1) at the protein level for BRD 4, BRD2 and BRD 3 as well as c-MYC.

Figure 43H:
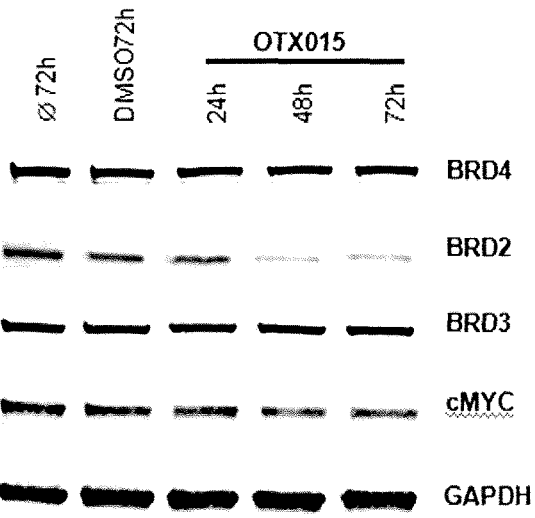
Figure 43I:
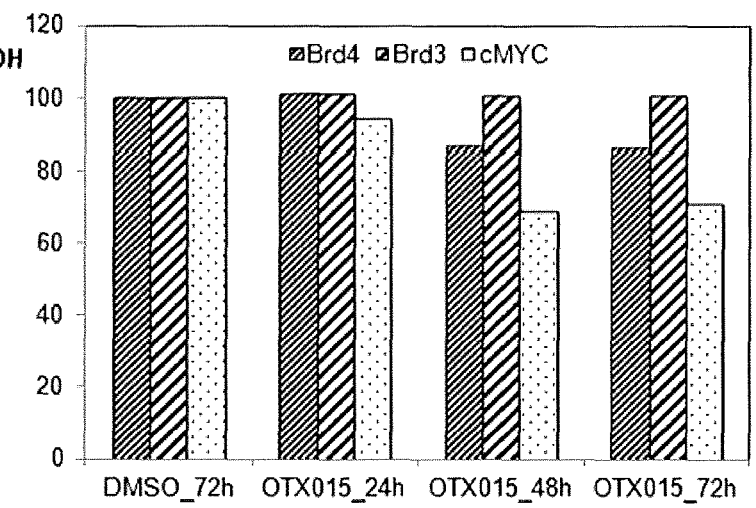

In the selected AML cell line HL60 BRD4 and BRD3 remained unaffected after 72 h Compound (1-1) exposure at 500 nM with a transient downregulation of c-MYC observed after 24 h-treatment (FIG. 43A-43C) while the almost resistant AML cell line K562 displayed downregulation of BRD4, BRD3 and c-MYC starting after 24 h exposure (FIG. 43D-43F). For the sensitive ALL cell lines, Jurkat displayed c-MYC downregulation at 48 h and 72 h (FIG. 43G-43I) while BRD4, BRD3 and c-MYC remained unaffected in RS4-11 (FIG. 43J-43L).

Example 16: Immunoblots

Protein extracts were prepared from $7 \times 10^6$ cells; 30 µg were separated on sodium dodecyl sulfate (SDS)-polyacrylamide gels using 4-15% gradient gels (Bio-Rad, Marnes-la-Coquette, France) and transferred to nitrocellulose membranes using Mini Trans-Blot Electrophoretic Transfer cell (Bio-Rad). The membranes were blocked with LiCor blocking buffer (LiCor, Lincoln, Nebr., USA) and incubated with the respective primary antibody: anti-BRD4 (Epitomics 5716-1, Burlingame, USA), anti-BRD3 (ab56342, AbCam, UK), anti-BRD2 (ab37633, AbCam, UK), anti c-MYC (sc-764 (N262), Santa Cruz, USA) and anti-GAPDH (Invitrogen 398600, Grand Island, USA). Blots were stained with either goat anti-rabbit InfraRedDye 680RD or goat anti-mouse InfraRedDye 800CWsecondary antibody (LiCor). Membranes were imaged using a LiCor Odyssey scanner. Boxes were manually placed around each band of interest, which returned near-infrared fluorescent values of raw intensity with intra-lane background subtracted using Odyssey 3.0 analytical software (LiCor).

Blots for BRD2 were stained with either goat (BRD2) anti-rabbit peroxidase-labeled or goat anti-mouse (GAPDH) peroxidase-labeled secondary antibody (Biorad, Hercules, USA) and were revealed using an enhanced chemiluminescence detection system (ECL and ECL plus, GE Healthcare, Buckinghamshire, UK).

Example 17: Quantitative-Real Time Polymerase Chain Reaction (RQ-PCR)

The total RNA obtained after extraction with TRIZOL (Invitrogen, Grand Island, USA) were titrated to 1 µg/uL and stored at −80° C. The complementary DNA (cDNA) was synthesized from 1 µg RNA. The RQ-PCR reactions (BRD2, BRD3, BRD4, c-MYC and ABL) were performed in a volume of 25 µl from a tenth of the cDNA (equivalent to 100 ng of RNA) on a thermocycler ABI7900HT in standard mode (1 cycle of 2 minutes at 50° C.-10 minutes at 95° C. followed by 50 cycles of 15 seconds at 95° C.-1 minute at 60° C.). The primers used are summarized in Table 9.

TABLE 9

Primers used for PCR.

| | | | |
|---|---|---|---|
| c-MYC | Forward primer | 5'-GGATTTTTTTCGGGTAGTGGAA-3' | SEQ ID NO: 1 |
| | Reverse primer | 5'-TTCCTGTTGGTGAAGCTAACGTT-3' | SEQ ID NO: 2 |
| | Probe | 5'FAM-CTCCCGCGACGATGCCCCT-TAMRA 3' | SEQ ID NO: 3 |
| BRD4 | Forward primer | 5' CCCTGAAGCCGTCCACACT3 ' | SEQ ID NO: 4 |
| | Reverse primer | 5'TTCTCAGCTTGAGGTTTCCTTTTC3' | SEQ ID NO: 5 |
| | Probe | 5'FAM CGCTATGTCACCTCCTGTTTGCGGA TAMRA3' | SEQ ID NO: 6 |
| BRD3 | Forward primer | 5'ACATGCAGAATGTGGTGGTGAA3 ' | SEQ ID NO: 7 |

TABLE 9-continued

Primers used for PCR.

|  |  |  |  |
|---|---|---|---|
|  | Reverse primer | 5'CGTCCACGGGCTGGTAGA3' | SEQ ID NO: 8 |
|  | Probe | 5'FAM ACGCTCTGGAAACACCAGTTCGCCT TAMRA3' | SEQ ID NO: 9 |
| BRD2 | Forward primer | 5' CCCGACGAGATTGAAATCGA3' | SEQ ID NO: 10 |
|  | Reverse primer | 5'CCGCAAACAGGAGGTGACATA3' | SEQ ID NO: 11 |
|  | Probe | 5'FAM TTGAGACCCTGAAGCCGTCCACACTG TAMRA3' | SEQ ID NO: 12 |
| ABL | Forward primer | 5'-TGGAGATAACACTCTAAGCATAACTAAAGGT-3' | SEQ ID NO: 13 |
|  | Reverse primer | 5'-GATGTAGTTGCTTGGGACCCA-3' | SEQ ID NO: 14 |
|  | Probe | 5'FAM CCATTTTTGGTTTGGGCTTCACACCATT TAMRA3' | SEQ ID NO: 15 |

Example 18: Effects of Compound (1-1) in Primary Cells

Figure 44A:
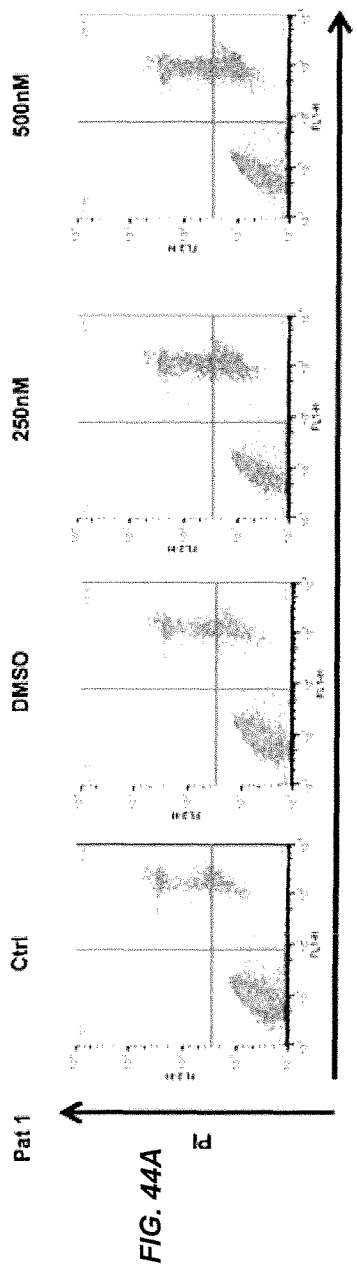
Figure 44B:
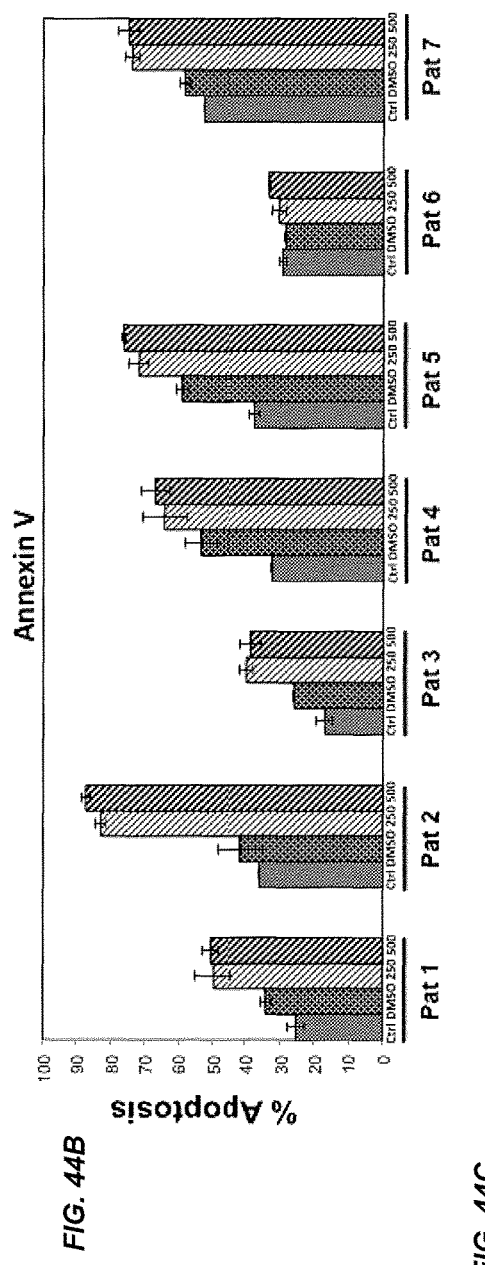
Figure 44C:
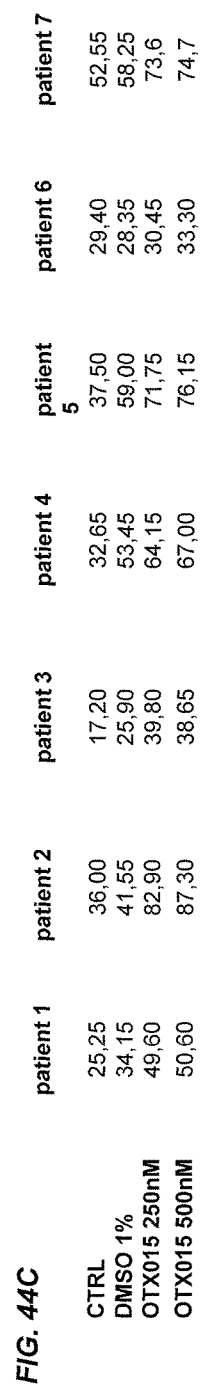
Figures 45D, 45E:
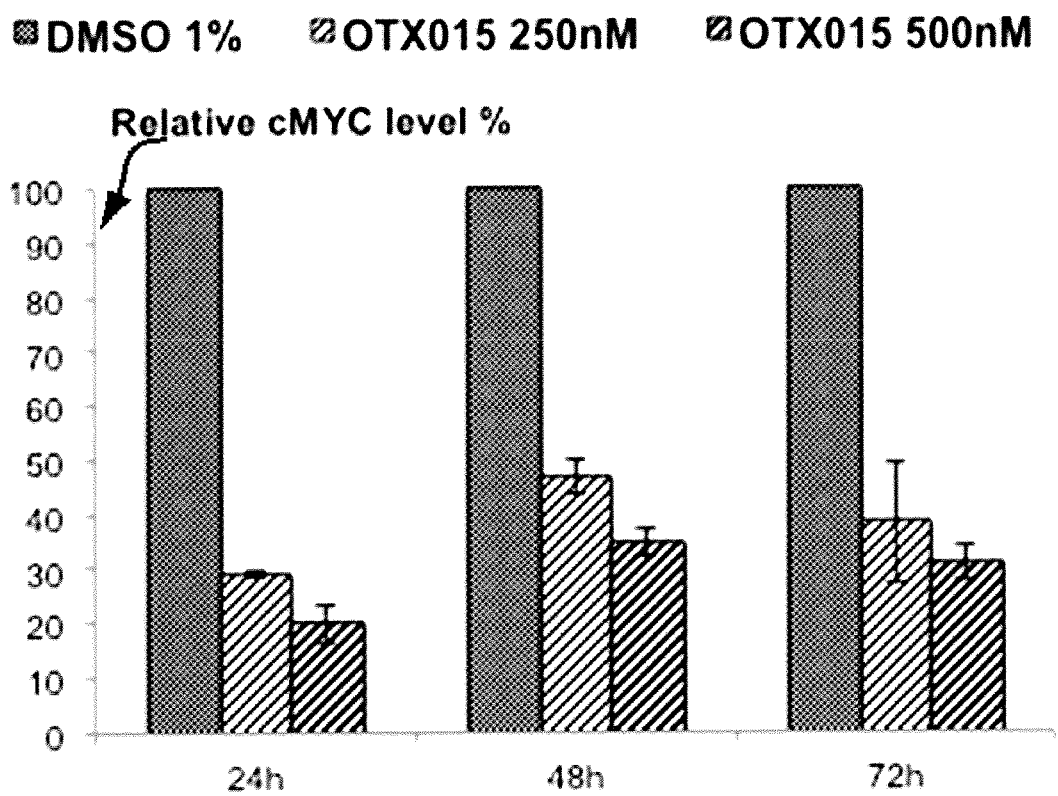

We further studied effects of Compound (1-1) on primary patient cells. We treated ex vivo 5 samples from AML patients and 2 ALL including 1 ALL Ph+ patient. Patient characteristics are shown in FIG. 44D. Compound (1-1) induced apoptosis in primary AML patient samples at various degrees ranging from 35-85% (FIGS. 44A-44C). The Ph+ ALL patient appeared to be resistant.

Basal gene expression of BRD2, BRD3 and BRD4 in patient samples was assessed by RQ-PCR analysis. Patient characteristics are summarized in Table 10. Among ALL patients, Ph+ ALL showed lower BRD expression levels (FIGS. 47A and 47B; Patients 3 to 6) while BRD expression levels among AML patients were more heterogeneous (FIGS. 47C and 47D).

TABLE 10

Characteristics of different ALL and AML patients studied for BRD expression.

| No | Gender | Disease | Karyotype | Molecular Biology |
|---|---|---|---|---|
| 1 | M | B-ALL | Normal | — |
| 2 | F | B-ALL | Normal | — |
| 3 | M | B-ALL | PH1+ | bcr/abl |
| 4 | F | B-ALL | PH1+ | bcr/abl |
| 5 | M | B-ALL | PH1+ | bcr/abl |
| 6 | M | B-ALL | PH1+ | bcr/abl |
| 7 | M | T-ALL | UK | — |
| 8 | F | T-ALL | UK | — |
| 9 | M | T-ALL | UK | — |
| 10 | M | T-ALL | Normal | CalmAf10 |
| 1 | M | AML | Normal | CEBP alpha |
| 2 | M | AML | Normal | dup MLL |
| 3 | F | AML | Normal | dup MLL |
| 4 | F | AML | Normal | FLT3 ITD |
| 5 | M | AML | Normal | FLT3 ITD |
| 6 | F | AML | Normal | FLT3 ITD |
| 7 | M | AML | Normal | FLT3 ITD + Dup MLL |
| 8 | M | AML | inv 16 | CBF MYH |
| 9 | M | AML | inv 16 | CBF MYH |
| 10 | F | AML | Complex | — |
| 11 | M | AML | Complex | — |
| 12 | F | AML | Normal | NPM1 |
| 13 | M | AML | Normal | NPM1 |
| 14 | F | AML | Normal | NPM1 |

TABLE 10-continued

Characteristics of different ALL and AML patients studied for BRD expression.

| No | Gender | Disease | Karyotype | Molecular Biology |
|---|---|---|---|---|
| 15 | M | AML | Normal | NPM1 |
| 16 | M | AML | Normal | NPM1 |
| 17 | F | AML | Normal | NPM1 + FLT3 ITD |
| 18 | M | AML | t(8; 21) | AML ETO |
| 19 | M | AML | t(8; 21) | AML ETO |

Protein extracts could be obtained from BM cells of patient 5 (Table 10; FIG. 44) upon ex vivo treatment with 250 and 500 nM of OTX015 respectively. Those cells displayed downregulation of c-MYC after 72 h exposure to OTX015 (45A-45C).

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

I claim:

1. A method of treating an acute lymphoblastic leukemia comprising administering to a patient a pharmaceutically acceptable amount of a composition comprising a thienotriazolodiazepine compound which is (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, wherein the thienotriazolodiazepine compound is formed as a solid dispersion comprising an amorphous thienotriazolodiazepine compound wherein the solid dispersion exhibits an X-ray powder diffraction pattern substantially free of diffraction lines associated with crystalline thienotriazolodiazepine compound, and a pharmaceutically acceptable polymer which is hydroxypropylmethylcellulose acetate succinate having a thienotriazolodiazepine compound to hydroxypropylmethylcellulose acetate succinate weight ratio of 1:3 to 1:1.

2. The method of claim 1, wherein the thienotriazolodiazepine compound is (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl)acetamide dihydrate.

3. The method according to claim 1, wherein the solid dispersion exhibits a single glass transition temperature (Tg) inflection point ranging from about 130° C. to about 140° C.

4. A method of treating an acute myeloid leukemia comprising administering to a patient a pharmaceutically acceptable amount of a composition comprising a thienotriazolodiazepine compound which is (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof, wherein the thienotriazolodiazepine compound is formed as a solid dispersion comprising an amorphous thienotriazolodiazepine compound wherein the solid dispersion exhibits an X-ray powder diffraction pattern substantially free of diffraction lines associated with crystalline thienotriazolodiazepine compound and a pharmaceutically acceptable polymer which is hydroxypropylmethylcellulose acetate succinate having a thienotriazolodiazepine compound to hydroxypropylmethylcellulose acetate succinate weight ratio of 1:3 to 1:1.

5. The method of claim 4, wherein the thienotriazolodiazepine compound is (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl)acetamide dihydrate.

6. The method according to claim 4, wherein the solid dispersion exhibits a single glass transition temperature (Tg) inflection point ranging from about 130° C. to about 140° C.

7. A method of treating a BCR-ABL positive acute lymphoblastic leukemia comprising administering to a patient a pharmaceutically acceptable amount of a composition comprising a thienotriazolodiazepine compound which is (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof.

8. The method of claim 7, wherein the thienotriazolodiazepine compound is (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl)acetamide dihydrate.

9. The method according to claim 8, wherein the thienotriazolodiazepine compound is formed as a solid dispersion comprising an amorphous thienotriazolodiazepine compound and a pharmaceutically acceptable polymer which is hydroxypropylmethylcellulose acetate succinate having a thienotriazolodiazepine compound to hydroxypropylmethylcellulose acetate succinate weight ratio of 1:3 to 1:1.

10. The method according to claim 9, wherein the solid dispersion exhibits an X-ray powder diffraction pattern substantially free of diffraction lines associated with crystalline thienotriazolodiazepine compound.

11. The method according to claim 10, wherein the solid dispersion exhibits a single glass transition temperature (Tg) inflection point ranging from about 130° C. to about 140° C.

12. A method of treating a CD34 positive acute myeloid leukemia comprising administering to a patient a pharmaceutically acceptable amount of a composition comprising a thienotriazolodiazepine compound which is (S)-2-[4-(4-chlorophenyl)-2,3,9-trimethyl-6H-thieno[3,2-f][1,2,4]triazolo-[4,3-a][1,4]diazepin-6-yl]-N-(4-hydroxyphenyl)acetamide or a dihydrate thereof.

13. The method of claim 12, wherein the thienotriazolodiazepine compound is (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl)acetamide dihydrate.

14. The method according to claim 13, wherein the thienotriazolodiazepine compound is formed as a solid dispersion comprising an amorphous thienotriazolodiazepine compound and a pharmaceutically acceptable polymer which is hydroxypropylmethylcellulose acetate succinate having a thienotriazolodiazepine compound to hydroxypropylmethylcellulose acetate succinate weight ratio of 1:3 to 1:1.

15. The method according to claim 14, wherein the solid dispersion exhibits an X-ray powder diffraction pattern substantially free of diffraction lines associated with crystalline thienotriazolodiazepine compound.

16. The method according to claim 14, wherein the solid dispersion exhibits a single glass transition temperature (Tg) inflection point ranging from about 130° C. to about 140° C.

* * * * *